US012590066B2

(12) United States Patent
Pae et al.

(10) Patent No.: US 12,590,066 B2
(45) **Date of Patent: *Mar. 31, 2026**

(54) FUSED-HETEROCYCLYL-CARBONOHYDRAZONOYL DICYANIDE COMPOUNDS AND USE THEREOF

(71) Applicant: KOREA INSTITUTE OF SCIENCE AND TECHNOLOGY, Seoul (KR)

(72) Inventors: Ae Nim Pae, Seoul (KR); Yun Kyung Kim, Seoul (KR); Sang Min Lim, Seoul (KR); Sungsu Lim, Seoul (KR); Haeun Lee, Seoul (KR); Woo Seung Son, Seoul (KR); Hye Yeon Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 602 days.

This patent is subject to a terminal disclaimer.

(21) Appl. No.: 18/011,459

(22) PCT Filed: Jun. 18, 2021

(86) PCT No.: PCT/KR2021/007691

§ 371 (c)(1),
(2) Date: Dec. 19, 2022

(87) PCT Pub. No.: WO2021/256899

PCT Pub. Date: Dec. 23, 2021

(65) Prior Publication Data

US 2023/0295095 A1 Sep. 21, 2023

(30) Foreign Application Priority Data

Jun. 19, 2020 (KR) ........................ 10-2020-0075041

(51) Int. Cl.

| | |
|---|---|
| ***C07D 217/24*** | (2006.01) |
| ***C07D 215/227*** | (2006.01) |
| ***C07D 235/26*** | (2006.01) |
| ***C07D 263/58*** | (2006.01) |
| ***C07D 277/68*** | (2006.01) |
| ***C07D 471/04*** | (2006.01) |

(52) U.S. Cl.

CPC ....... *C07D 217/24* (2013.01); *C07D 215/227* (2013.01); *C07D 235/26* (2013.01); *C07D 263/58* (2013.01); *C07D 277/68* (2013.01); *C07D 471/04* (2013.01)

(58) Field of Classification Search

CPC .............. C07D 217/24; C07D 215/227; C07D 235/26; C07D 263/58; C07D 277/68; C07D 471/04

See application file for complete search history.

(56) References Cited

U.S. PATENT DOCUMENTS

| | | | | |
|---|---|---|---|---|
| 8,809,302 B2 | 8/2014 | Cohen et al. | | |
| 9,962,384 B1 | 5/2018 | Kim et al. | | |
| 2022/0396553 A1* | 12/2022 | Pae | ...................... | C07D 471/04 |
| 2023/0278963 A1* | 9/2023 | Pae | ...................... | C07D 237/04 514/247 |
| 2023/0278965 A1* | 9/2023 | Pae | ...................... | C07D 413/12 514/255.05 |

FOREIGN PATENT DOCUMENTS

| | | | |
|---|---|---|---|
| EP | 3 424 908 A1 | 1/2019 | |
| KR | 10-2018-0050130 A | 5/2018 | |
| KR | 10-2020-0076808 A | 6/2020 | |
| WO | WO 03/045379 A1 | 6/2003 | |
| WO | WO 2006/024858 A1 | 3/2006 | |
| WO | WO-2020130214 A1 * | 6/2020 | ........... C07D 417/12 |

OTHER PUBLICATIONS

National Center for Biotechnology Information. PubChem Substance Record for SID 289193799, SID 289193799, Source: Aurora Fine Chemicals LLC. https://pubchem.ncbi.nlm.nih.gov/substance/289193799. Available Jan. 18, 2016. (Year: 2016).*

Alzheimer's Association "Can Alzheimer's Disease Be Prevented?" Downloaded Jun. 11, 2025 from https://www.alz.org/alzheimers-dementia/research-and-progress/prevention (Year: 2025).*

Crowe, Alex, et al. "Compound screening in cell-based models of tau inclusion formation: Comparison of primary neuron and HEK293 cell assays." *Journal of Biological Chemistry* vol. 295. Issue 12 (2020). pp. 4001-4013.

Somei, Masanori, et al. "The Chemistry of Indoles. XII. A Facile Route To 5-Nitroisocoumarins and Methyl Indole-4-carboxylate." Chemical and Pharmaceutical Bulletin 29.1 (1981): 249-253.

Korean Office Action issued on Oct. 16, 2023, in counterpart Korean Patent Application No. 10-2021-0079536 (9 pages in Korean).

Korean Office Action issued on Jan. 23, 2024, in counterpart Korean Patent Application No. 10-2021-0079536 (5 pages in Korean).

Mulwad, et al., "Synthesis and antimicrobial screening of 5-(4, 7-dimethyl-2-oxo-2H-benzopyran-6-ylazo)-2-methyl-6-morpholin-4-yl-2, 3-dihydro-3H-pyrimidin-4-one and 5-(4, 7-dimethyl-2-oxo-2H-benzopyran-6-ylazo)-2-methyl-6-piperidin-1-yl-2, 3-dihydro-3H-pyrimidin-4-one." Indian Journal of Chemistry, vol. 46B, Nov. 2007, pp. 1873-1878.

Australian Office Action issued on May 31, 2023, in counterpart Australian Patent Application No. 2021291666 (8 pages in English).

D3: CAS Registry No. 663922-38-1; STN Entry Date Mar. 17, 2004, https://www.cas.org/cas-data/cas-registry, (1 Page in English).

Australian Office Action Issued on May 16, 2024, in Counterpart Australian Patent Application No. 2021291666 (4 Pages in English).

* cited by examiner

*Primary Examiner* — Daniel R Carcanague
(74) *Attorney, Agent, or Firm* — NSIP Law

(57) ABSTRACT

Provided are novel fused-heterocyclyl-carbonohydrazonoyl dicyanide compounds and uses thereof.

20 Claims, No Drawings

FUSED-HETEROCYCLYL-CARBONOHYDRAZONOYL DICYANIDE COMPOUNDS AND USE THEREOF

CROSS-REFERENCE TO RELATED APPLICATIONS

This application is a U.S. National Stage Application of International Application No. PCT/KR2021/007691, filed on Jun. 18, 2021, which claims the benefit under 35 USC 119 (a) and 365 (b) of Korean Patent Application No. 10-2020-0075041, filed on Jun. 19, 2020, in the Korean Intellectual Property Office, the entire disclosures of which are incorporated herein by reference for all purposes.

TECHNICAL FIELD

The present invention relates to novel fused-heterocyclyl-carbonohydrazonoyl dicyanide compounds and uses thereof.

BACKGROUND ART

Tau protein (tau (T) protein), which is a microtubule-associated protein (MAP) mainly expressed in axons of nerve cells with a molecular weight of 50,000 to 70,000, serves to stabilize microtubules, and represents molecular diversity through phosphorylation. In humans, tau protein is formed into six isoforms by the insertion of 29 or 58 amino acid residues at the N-terminus and the alternative splicing of mRNA of 3 or 4 repeating structures (referred to as microtubule binding domain) at the C-terminus.

In healthy nerves, tau protein stabilizes microtubules by promoting growth from axons and nerve cell polarization. When pathological hyperphosphorylation occurs, tau protein separates from microtubules, resulting in insoluble aggregation. Further, a structural skeleton inducing the aggregation of tau protein has been proposed, and evidence has been provided that insoluble filaments are formed from 10 soluble monomers, and that these filaments are bound into high-dimensional structures called neurofibrillary tangles (NFTs). Human full-length tau protein includes a microtubule binding domain consisting of four repetitive conserved sequences. Among these repetitive sequences, positively charged residues have an important function in binding to highly negatively charged microtubules (20 to 30 electrons per αβ-tubulin dimer). The binding affinity to tau microtubules is also actively regulated by the phosphorylation of tau protein, and this phosphorylation causes dynamic rearrangement of microtubule networks. When tau protein is phosphorylated abnormally excessively, the balance of this dynamic rearrangement is disrupted, and the affinity to microtubules is rapidly decreased.

The hyperphosphorylation and/or aggregation of tau proteins cause abnormal accumulation of these tau proteins in nerve cells, which is pointed to as a cause of various neurodegenerative diseases and the like. Tau protein aggregates are mainly found in the cell bodies and dendrites of nerve cells, and these tau protein aggregates are called neurofibrillary tangles (NFTs) and neuropil threads. Examination of the microstructures of neurofibrillary tangles (NFTs) reveals that such microstructures thereof consist of paired helical filaments (PHFs) in which tau proteins are entangled like fine threads and are aggregated and hyperphosphorylated, unlike normal tau protein. An abnormal tau protein aggregation phenomenon appears also in tauopathy. In this case, although it is not known exactly what role the aggregation of tau protein plays in the progress of tauopathy, this tau protein aggregation phenomenon appears similar to an aggregation phenomenon that is common in general neurodegenerative diseases.

As such, although it is known that hyperphosphorylation and/or aggregation of tau protein causes various neurodegenerative diseases comprising Alzheimer's disease and tauopathy, the specific mechanism how these abnormal tau species cause changes in the signaling pathway and elicit neurotoxicity has not yet been verified, and there are no effective treatment methods or therapeutic agents yet available to treat these diseases.

DISCLOSURE

Technical Problem

As a result of intensive efforts to develop novel small-molecule compounds capable of inhibiting aggregation and/or hyperphosphorylation of tau protein, the present inventors have found that a series of novel fused-heterocyclyl-carbonohydrazonoyl dicyanide compounds effectively inhibit aggregation of tau protein without exhibiting cytotoxicity at effective concentrations, thereby completing the present invention.

Technical Solution

An object of the present invention is to provide a compound represented by Formula 1 below or a pharmaceutically acceptable salt thereof:

[Formula 1]

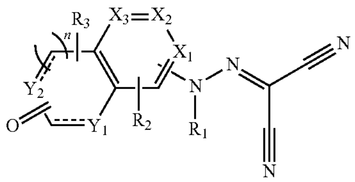

in Formula 1 above, $X_1$ to $X_3$ are each independently N or C(H);

$Y_1$ and $Y_2$ are each independently $N(R_4)$, C(H), O, or S;

n is 0 or 1;

is 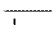 or  forming an aromatic or non-aromatic fused-heterocyclic ring;

$R_1$ is hydrogen, $C_{1-6}$ alkyl, or $C_{1-6}$ alkylcarbonyl;

$R_2$ and $R_3$ are each independently hydrogen, $C_{1-6}$ alkyl, halogen, cyano, $C_{1-6}$ haloalkyl, $C_{1-6}$ alkoxy, $C_{1-6}$ haloalkoxy, $C_{1-6}$ alkylamino, di($C_{1-6}$ alkyl)amino, $C_{1-6}$ alkylaminocarbonyl, or di($C_{1-6}$ alkyl)aminocarbonyl; and $R_4$ is hydrogen, $C_{1-6}$ alkyl, $C_{1-6}$ alkoxy, $C_{1-6}$ alkoxy-$C_{0-6}$ alkyl, $C_{1-6}$ haloalkyl, $C_{3-6}$ cycloalkyl-$C_{0-6}$ alkyl, 5- or 6-membered heterocycle-$C_{0-6}$ alkyl, $C_{6-10}$ aryl, or 5- to 10-membered heteroaryl, wherein the 5- or 6-membered heterocycle, $C_{6-10}$ aryl, and 5- to 10-membered heteroaryl are unsubstituted or substituted with $C_{1-6}$ alkoxy or $C_{1-6}$ alkoxycarbonyl.

Another object of the present invention is to provide a method of preparing the compound of the compound described above.

Still another object of the present invention is to provide a composition for inhibiting aggregation of tau protein including the compound described above as an active ingredient.

Still another object of the present invention is to provide a composition for inhibiting hyperphosphorylation of tau protein including the compound described above as an active ingredient.

Still another object of the present invention is to provide a pharmaceutical composition for preventing or treating a disease caused by aggregation or hyperphosphorylation of tau protein including the compound described above as an active ingredient.

Still another object of the present invention is to provide a method of preventing or treating a disease caused by aggregation or hyperphosphorylation of tau protein, the method including administering the pharmaceutical composition described above to a subject in need thereof.

Advantageous Effects

The novel fused-heterocyclyl-carbonohydrazonoyl dicyanide compounds of the present invention may effectively inhibit aggregation and/or hyperphosphorylation of tau protein, and thus may be effectively used in prevention or treatment of diseases caused thereby such as Alzheimer's disease and various tauopathies.

BEST MODE

A first aspect of the present invention provides a compound represented by Formula 1 below or a pharmaceutically acceptable salt thereof:

[Formula 1]

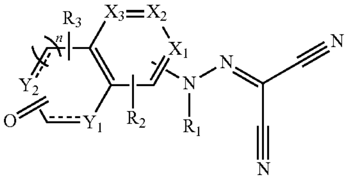

in Formula 1 above, $X_1$ to $X_3$ are each independently N or C(H);

$Y_1$ and $Y_2$ are each independently $N(R_4)$, C(H), O, or S;

n is 0 or 1;

is or forming an aromatic or non-aromatic fused-heterocyclic ring;

$R_1$ is hydrogen, $C_{1-6}$ alkyl, or $C_{1-6}$ alkylcarbonyl;

$R_2$ and $R_3$ are each independently hydrogen, $C_{1-6}$ alkyl, halogen, cyano, $C_{1-6}$ haloalkyl, $C_{1-6}$ alkoxy, $C_{1-6}$ haloalkoxy, $C_{1-6}$ alkylamino, di($C_{1-6}$ alkyl)amino, $C_{1-6}$ alkylaminocarbonyl, or di($C_{1-6}$ alkyl)aminocarbonyl; and $R_4$ is hydrogen, $C_{1-6}$ alkyl, $C_{1-6}$ alkoxy, $C_{1-6}$ alkoxy-$C_{0-6}$ alkyl, $C_{1-6}$ haloalkyl, $C_{3-6}$ cycloalkyl-$C_{0-6}$ alkyl, 5- or 6-membered heterocycle-$C_{0-6}$ alkyl, $C_{6-10}$ aryl, or 5- to 10-membered heteroaryl, wherein the 5- or 6-membered heterocycle, $C_{6-10}$ aryl, and 5- to 10-membered heteroaryl are unsubstituted or substituted with $C_{1-6}$ alkoxy or $C_{1-6}$ alkoxycarbonyl.

For example, in the compound of the present invention, $R_1$ is hydrogen, $C_{1-6}$ alkyl, or $C_{1-6}$ alkylcarbonyl;

$R_2$ is hydrogen, halogen, $C_{1-6}$ alkyl, or $C_{1-6}$ alkoxy;

$R_3$ is hydrogen or $C_{1-6}$ alkyl; and $R_4$ is hydrogen, $C_{1-6}$ alkyl, $C_{1-6}$ haloalkyl, $C_{3-6}$ cycloalkyl-$C_{0-4}$ alkyl, or $C_{6-10}$ aryl, without being limited thereto.

Specifically, in the compound of the present invention, $R_1$ is hydrogen, methyl, or acetyl;

$R_2$ is hydrogen, chloro, fluoro, methyl, or methoxy;

$R_3$ is hydrogen or methyl; and $R_4$ is hydrogen, methyl, ethyl, isopropyl, difluoromethyl, cyclopropyl, or phenyl, without being limited thereto.

For example, the compound of the present invention may be a compound represented by Formula 2 below:

[Formula 2]

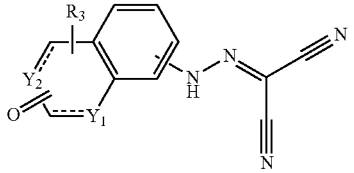

in Formula 2 above, one of $Y_1$ and $Y_2$ is CH, and the other is $NR_4$;

in contact with CH is , and in contact with $NR_4$ is ;

$R_3$ is hydrogen or methyl; and $R_4$ is hydrogen, methyl, or isopropyl.

Alternatively, the compound of the present invention may be a compound represented by Formula 3 below:

[Formula 3]

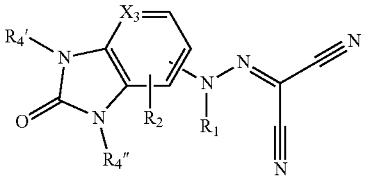

in Formula 3 above, $X_3$ is C(H), or N;

$R_1$ is hydrogen, methyl, or acetyl;

$R_2$ is hydrogen, chloro, fluoro, methyl, or methoxy; and $R_{4'}$ and $R_{4''}$ are each independently hydrogen, methyl, ethyl, isopropyl, difluoromethyl, cyclopropyl, or phenyl.

Furthermore, the compound of the present invention may be a compound represented by Formula 4 below:

[Formula 4]

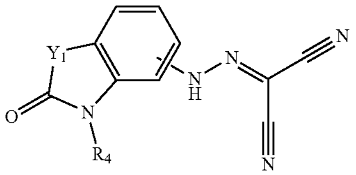

in Formula 4 above, $Y_1$ is S or O; and $R_4$ is hydrogen, methyl, isopropyl, or difluoromethyl.

More specifically, the compound represented by Formula 1 may be 1. (1-oxo-1,2-dihydroisoquinolin-7-yl)carbonohydrazonoyl dicyanide,
2. (2-methyl-1-oxo-1,2-dihydroisoquinolin-7-yl)carbonohydrazonoyl dicyanide,
3. (2-isopropyl-1-oxo-1,2-dihydroisoquinolin-7-yl)carbonohydrazonoyl dicyanide, 4. (1-oxo-1,2-dihydroisoquinolin-5-yl)carbonohydrazonoyl dicyanide,
5. (2-methyl-1-oxo-1,2-dihydroisoquinolin-5-yl)carbonohydrazonoyl dicyanide,
6. (2-isopropyl-1-oxo-1,2-dihydroisoquinolin-5-yl)carbonohydrazonoyl dicyanide,
7. (2,3-dimethyl-1-oxo-1,2-dihydroisoquinolin-5-yl)carbonohydrazonoyl dicyanide,
8. (2-oxo-1,2-dihydroquinolin-6-yl)carbonohydrazonoyl dicyanide,
9. (6-fluoro-1,3-dimethyl-2-oxo-2,3-dihydro-1H-benzo[d]imidazol-5-yl)carbonohydrazonoyl dicyanide,
10. (6-chloro-1,3-dimethyl-2-oxo-2,3-dihydro-1H-benzo[d]imidazol-5-yl)carbonohydrazonoyl dicyanide,
11. (7-chloro-1,3-dimethyl-2-oxo-2,3-dihydro-1H-benzo[d]imidazol-5-yl)carbonohydrazonoyl dicyanide,
12. (1,3-dimethyl-2-oxo-2,3-dihydro-1H-imidazo[4,5-b]pyridin-6-yl)carbonohydrazonoyl dicyanide,
13. (2-oxo-2,3-dihydrobenzo[d]thiazol-6-yl)carbonohydrazonoyl dicyanide,
14. (3-methyl-2-oxo-2,3-dihydrobenzo[d]thiazol-6-yl)carbonohydrazonoyl dicyanide,
15. (2-oxo-2,3-dihydrobenzo[d]oxazol-6-yl)carbonohydrazonoyl dicyanide,
16. (3-methyl-2-oxo-2,3-dihydrobenzo[d]oxazol-6-yl)carbonohydrazonoyl dicyanide,
17. (1-methyl-2-oxo-2,3-dihydro-1H-benzo[d]imidazol-5-yl)carbonohydrazonoyl dicyanide,
18. (3-isopropyl-2-oxo-2,3-dihydrobenzo[d]thiazol-6-yl)carbonohydrazonoyl dicyanide,
19. (3-(difluoromethyl)-2-oxo-2,3-dihydrobenzo[d]thiazol-6-yl)carbonohydrazonoyl dicyanide,
20. (3-isopropyl-2-oxo-2,3-dihydrobenzo[d]oxazol-6-yl)carbonohydrazonoyl dicyanide,
21. (3-(difluoromethyl)-2-oxo-2,3-dihydrobenzo[d]oxazol-6-yl)carbonohydrazonoyl dicyanide,
22. (1,3-dimethyl-2-oxo-2,3-dihydro-1H-benzo[d]imidazol-5-yl)carbonohydrazonoyl dicyanide,
23. (1,3-diisopropyl-2-oxo-2,3-dihydro-1H-benzo[d]imidazol-5-yl)carbonohydrazonoyl dicyanide,
24. (1,3-bis(difluoromethyl)-2-oxo-2,3-dihydro-1H-benzo[d]imidazol-5-yl)carbonohydrazonoyl dicyanide,
25. (1-methyl-2-oxo-1,2-dihydroquinolin-6-yl)carbonohydrazonoyl dicyanide,
26. (4-methyl-2-oxo-1,2-dihydroquinolin-6-yl)carbonohydrazonoyl dicyanide,
27. (1,4-dimethyl-2-oxo-1,2-dihydroquinolin-6-yl)carbonohydrazonoyl dicyanide,
28. (3-methyl-2-oxo-2,3-dihydrobenzo[d]oxazol-5-yl)carbonohydrazonoyl dicyanide,
29. (3-isopropyl-2-oxo-2,3-dihydrobenzo[d]oxazol-5-yl)carbonohydrazonoyl dicyanide,
30. (3-(difluoromethyl)-2-oxo-2,3-dihydrobenzo[d]oxazol-5-yl)carbonohydrazonoyl dicyanide,
31. (1,3,6-trimethyl-2-oxo-2,3-dihydro-1H-benzo[d]imidazol-5-yl)carbonohydrazonoyl dicyanide,
32. (6-methoxy-1,3-dimethyl-2-oxo-2,3-dihydro-1H-benzo[d]imidazol-5-yl)carbonohydrazonoyl dicyanide,
33. (7-methoxy-1,3-dimethyl-2-oxo-2,3-dihydro-1H-benzo[d]imidazol-5-yl)carbonohydrazonoyl dicyanide,
34. (1,3-diisopropyl-2-oxo-2,3-dihydro-1H-imidazo[4,5-b]pyridin-6-yl)carbonohydrazonoyl dicyanide,
35. (3-ethyl-1-methyl-2-oxo-2,3-dihydro-1H-benzo[d]imidazol-5-yl)carbonohydrazonoyl dicyanide,
36. (3-isopropyl-1-methyl-2-oxo-2,3-dihydro-1H-benzo[d]imidazol-5-yl)carbonohydrazonoyl dicyanide,
37. (3-(difluoromethyl)-1-methyl-2-oxo-2,3-dihydro-1H-benzo[d]imidazol-5-yl)carbonohydrazonoyl dicyanide,
38. (1-ethyl-3-methyl-2-oxo-2,3-dihydro-1H-benzo[d]imidazol-5-yl)carbonohydrazonoyl dicyanide,
39. (3-(difluoromethyl)-1-ethyl-2-oxo-2,3-dihydro-1H-benzo[d]imidazol-5-yl)carbonohydrazonoyl dicyanide,
40. (1-cyclopropyl-3-methyl-2-oxo-2,3-dihydro-1H-benzo[d]imidazol-5-yl)carbonohydrazonoyl dicyanide,
41. (1-cyclopropyl-3-ethyl-2-oxo-2,3-dihydro-1H-benzo[d]imidazol-5-yl)carbonohydrazonoyl dicyanide,
42. (1-cyclopropyl-3-isopropyl-2-oxo-2,3-dihydro-1H-benzo[d]imidazol-5-yl)carbonohydrazonoyl dicyanide,
43. (3-(difluoromethyl)-1-isopropyl-2-oxo-2,3-dihydro-1H-benzo[d]imidazol-5-yl)carbonohydrazonoyl dicyanide,
44. (1-ethyl-3-methyl-2-oxo-2,3-dihydro-1H-imidazo[4,5-b]pyridin-6-yl)carbonohydrazonoyl dicyanide,
45. (1-isopropyl-3-methyl-2-oxo-2,3-dihydro-1H-imidazo[4,5-b]pyridin-6-yl)carbonohydrazonoyl dicyanide,
46. (1-(difluoromethyl)-3-methyl-2-oxo-2,3-dihydro-1H-imidazo[4,5-b]pyridin-6-yl)carbonohydrazonoyl dicyanide,
47. (3-methyl-2-oxo-1-phenyl-2,3-dihydro-1H-imidazo[4,5-b]pyridin-6-yl)carbonohydrazonoyl dicyanide,
48. (3-ethyl-1-methyl-2-oxo-2,3-dihydro-1H-imidazo[4,5-b]pyridin-6-yl)carbonohydrazonoyl dicyanide,
49. (3-ethyl-1-isopropyl-2-oxo-2,3-dihydro-1H-imidazo[4,5-b]pyridin-6-yl)carbonohydrazonoyl dicyanide,
50. (1-(difluoromethyl)-3-ethyl-2-oxo-2,3-dihydro-1H-imidazo[4,5-b]pyridin-6-yl)carbonohydrazonoyl dicyanide,
51. (3-cyclopropyl-1-methyl-2-oxo-2,3-dihydro-1H-imidazo[4,5-b]pyridin-6-yl)carbonohydrazonoyl dicyanide,
52. (3-cyclopropyl-1-ethyl-2-oxo-2,3-dihydro-1H-imidazo[4,5-b]pyridin-6-yl)carbonohydrazonoyl dicyanide,
53. (3-cyclopropyl-1-isopropyl-2-oxo-2,3-dihydro-1H-imidazo[4,5-b]pyridin-6-yl)carbonohydrazonoyl dicyanide,
54. (3-isopropyl-1-methyl-2-oxo-2,3-dihydro-1H-imidazo[4,5-b]pyridin-6-yl)carbonohydrazonoyl dicyanide,
55. (1-ethyl-3-isopropyl-2-oxo-2,3-dihydro-1H-imidazo[4,5-b]pyridin-6-yl)carbonohydrazonoyl dicyanide,
56. (1,3-dimethyl-2-oxo-2,3-dihydro-1H-benzo[d]imidazol-5-yl)(methyl)carbonohydrazonoyl dicyanide, or
57. acetyl(1,3-dimethyl-2-oxo-2,3-dihydro-1H-benzo[d]imidazol-5-yl)carbonohydrazonoyl dicyanide, without being limited thereto.

Furthermore, these compounds may be compounds represented by formulae shown in Table 1 below.

TABLE 1

| | |
|---|---|
| 1 | 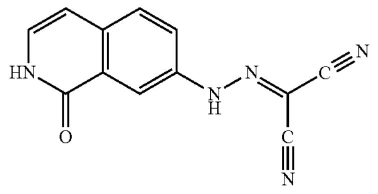 [SMILES: N#CC(C#N)=NNc1ccc2cc[nH]c(=O)c2c1] |
| 2 | 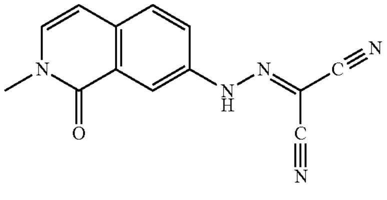 [SMILES: Cn1ccc2ccc(NN=C(C#N)C#N)cc2c1=O] |

TABLE 1-continued
3
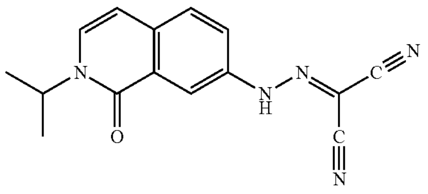 [SMILES: CC(C)n1ccc2ccc(NN=C(C#N)C#N)cc2c1=O]
4
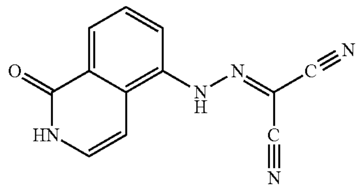 [SMILES: N#CC(C#N)=NNc1cccc2c(=O)[nH]ccc12]
5
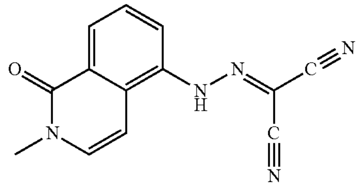 [SMILES: Cn1ccc2c(NN=C(C#N)C#N)cccc2c1=O]
6
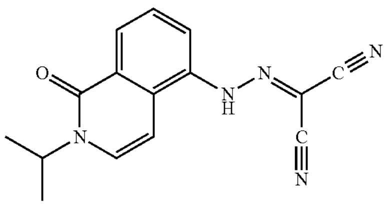 [SMILES: CC(C)n1ccc2c(NN=C(C#N)C#N)cccc2c1=O]
7
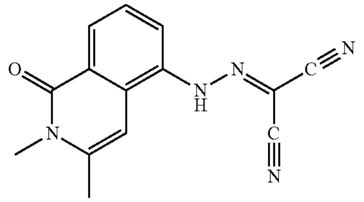 [SMILES: Cc1cc2c(NN=C(C#N)C#N)cccc2c(=O)n1C]
8
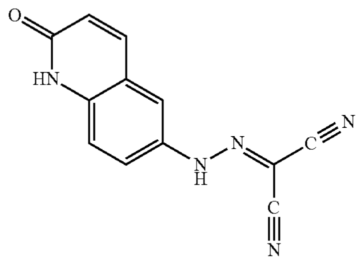 [SMILES: N#CC(C#N)=NNc1ccc2[nH]c(=O)ccc2c1]
9
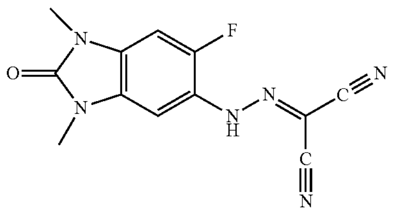 [SMILES: Cn1c(=O)n(C)c2cc(NN=C(C#N)C#N)c(F)cc21]
TABLE 1-continued
10
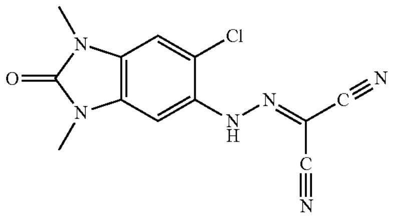 [SMILES: Cn1c(=O)n(C)c2cc(NN=C(C#N)C#N)c(Cl)cc21]
11
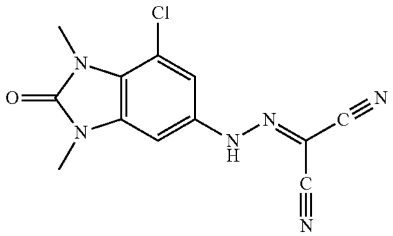 [SMILES: Cn1c(=O)n(C)c2c(Cl)cc(NN=C(C#N)C#N)cc21]
12
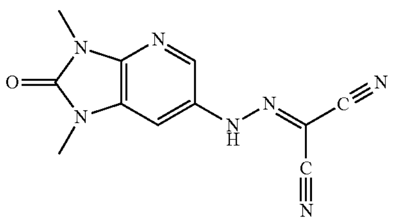 [SMILES: Cn1c(=O)n(C)c2ncc(NN=C(C#N)C#N)cc21]
13
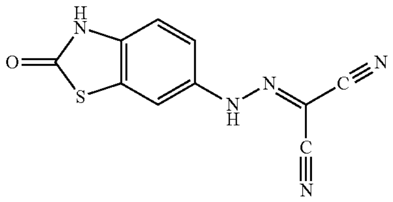 [SMILES: N#CC(C#N)=NNc1ccc2[nH]c(=O)sc2c1]
14
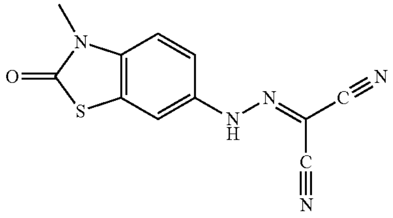 [SMILES: Cn1c(=O)sc2cc(NN=C(C#N)C#N)ccc21]
15
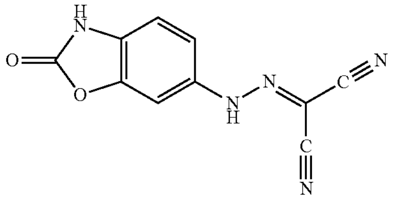 [SMILES: N#CC(C#N)=NNc1ccc2[nH]c(=O)oc2c1]
16
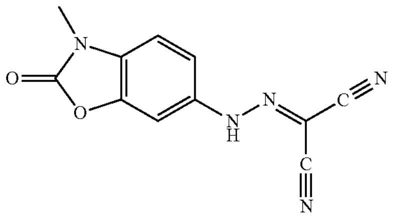 [SMILES: Cn1c(=O)oc2cc(NN=C(C#N)C#N)ccc21]

TABLE 1-continued
17
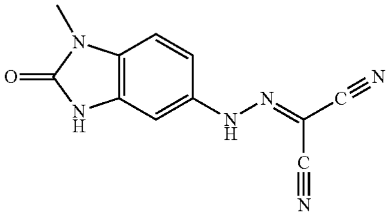 [SMILES: Cn1c(=O)[nH]c2cc(NN=C(C#N)C#N)ccc21]
18
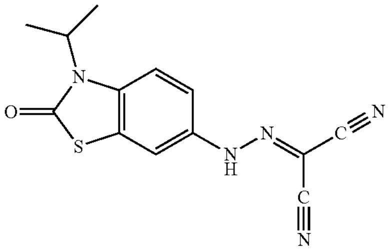 [SMILES: CC(C)n1c(=O)sc2cc(NN=C(C#N)C#N)ccc21]
19
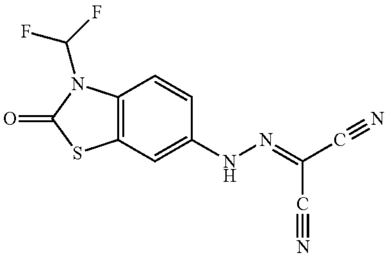 [SMILES: N#CC(C#N)=NNc1ccc2c(c1)sc(=O)n2C(F)F]
20
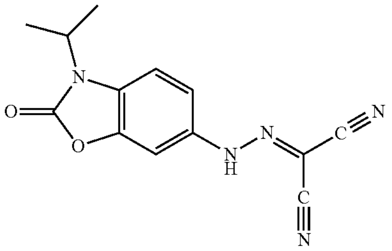 [SMILES: CC(C)n1c(=O)oc2cc(NN=C(C#N)C#N)ccc21]
21
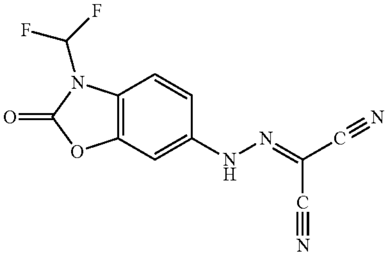 [SMILES: N#CC(C#N)=NNc1ccc2c(c1)oc(=O)n2C(F)F]
22
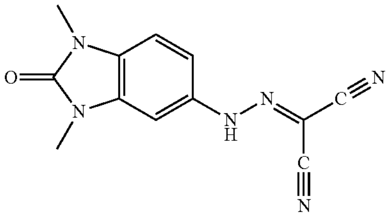 [SMILES: Cn1c(=O)n(C)c2cc(NN=C(C#N)C#N)ccc21]
TABLE 1-continued
23
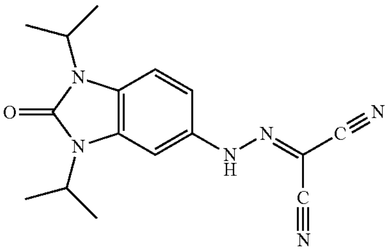 [SMILES: CC(C)n1c(=O)n(C(C)C)c2cc(NN=C(C#N)C#N)ccc21]
24
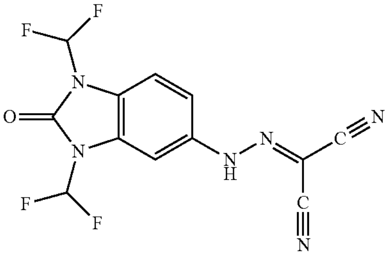 [SMILES: N#CC(C#N)=NNc1ccc2c(c1)n(C(F)F)c(=O)n2C(F)F]
25
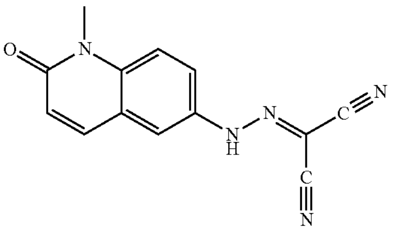 [SMILES: Cn1c(=O)ccc2cc(NN=C(C#N)C#N)ccc21]
26
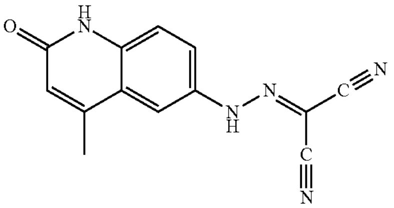 [SMILES: Cc1cc(=O)[nH]c2ccc(NN=C(C#N)C#N)cc12]
27
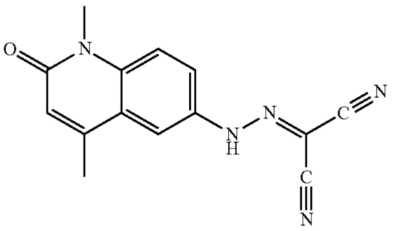 [SMILES: Cc1cc(=O)n(C)c2ccc(NN=C(C#N)C#N)cc12]
28
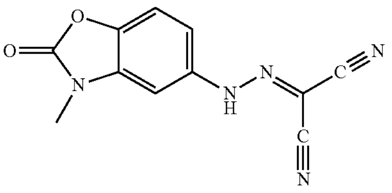 [SMILES: Cn1c(=O)oc2ccc(NN=C(C#N)C#N)cc21]

TABLE 1-continued
29
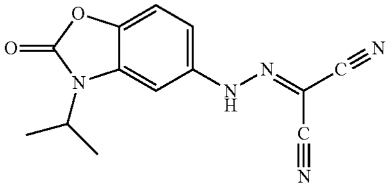 [SMILES: CC(C)n1c(=O)oc2ccc(NN=C(C#N)C#N)cc21]
30
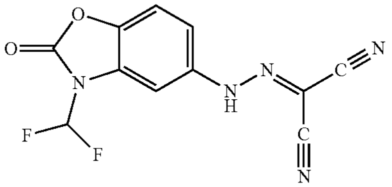 [SMILES: N#CC(C#N)=NNc1ccc2oc(=O)n(C(F)F)c2c1]
31
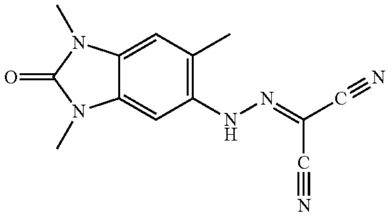 [SMILES: Cc1cc2c(cc1NN=C(C#N)C#N)n(C)c(=O)n2C]
32
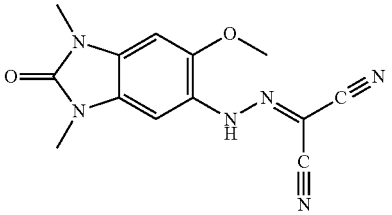 [SMILES: COc1cc2c(cc1NN=C(C#N)C#N)n(C)c(=O)n2C]
33
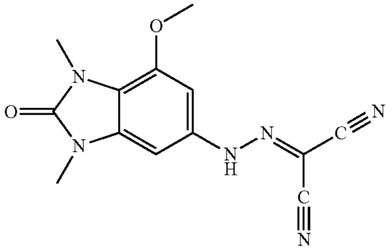 [SMILES: COc1cc(NN=C(C#N)C#N)cc2c1n(C)c(=O)n2C]
34
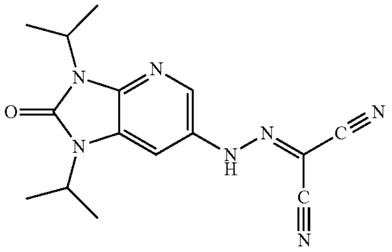 [SMILES: CC(C)n1c(=O)n(C(C)C)c2ncc(NN=C(C#N)C#N)cc21]
TABLE 1-continued
35
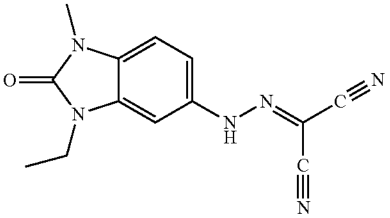 [SMILES: CCn1c(=O)n(C)c2ccc(NN=C(C#N)C#N)cc21]
36
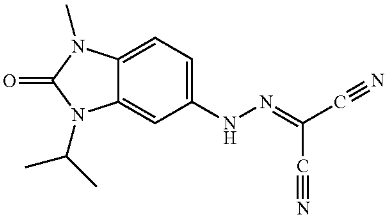 [SMILES: CC(C)n1c(=O)n(C)c2ccc(NN=C(C#N)C#N)cc21]
37
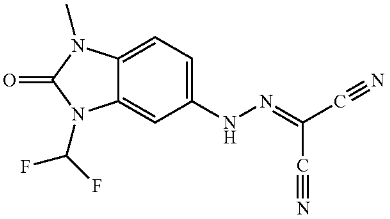 [SMILES: Cn1c(=O)n(C(F)F)c2cc(NN=C(C#N)C#N)ccc21]
38
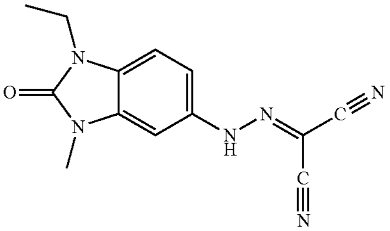 [SMILES: CCn1c(=O)n(C)c2cc(NN=C(C#N)C#N)ccc21]
39
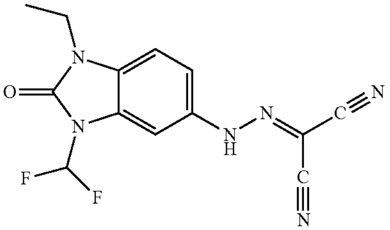 [SMILES: CCn1c(=O)n(C(F)F)c2cc(NN=C(C#N)C#N)ccc21]
40
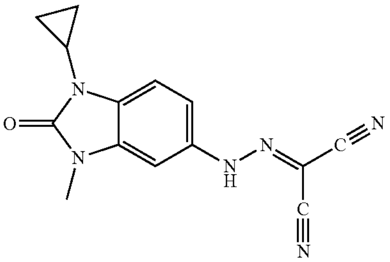 [SMILES: Cn1c(=O)n(C2CC2)c2ccc(NN=C(C#N)C#N)cc21]

TABLE 1-continued
41
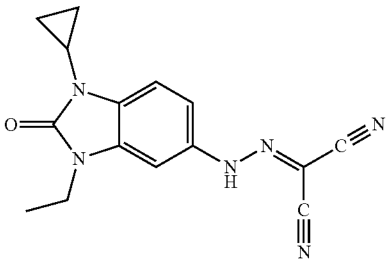 [SMILES: CCn1c(=O)n(C2CC2)c2ccc(NN=C(C#N)C#N)cc21]
42
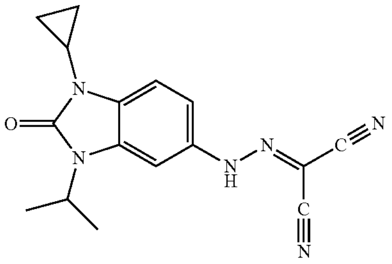 [SMILES: CC(C)n1c(=O)n(C2CC2)c2ccc(NN=C(C#N)C#N)cc21]
43
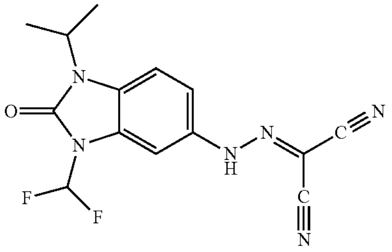 [SMILES: CC(C)n1c(=O)n(C(F)F)c2cc(NN=C(C#N)C#N)ccc21]
44
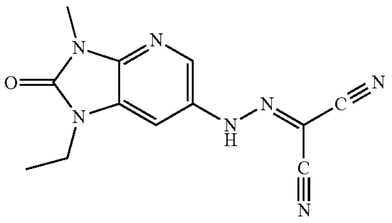 [SMILES: CCn1c(=O)n(C)c2ncc(NN=C(C#N)C#N)cc21]
45
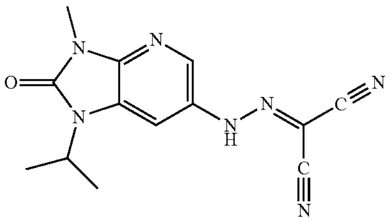 [SMILES: CC(C)n1c(=O)n(C)c2ncc(NN=C(C#N)C#N)cc21]
46
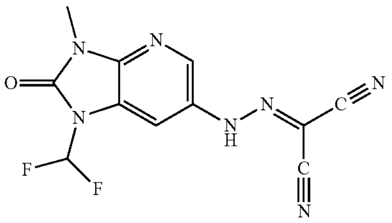 [SMILES: Cn1c(=O)n(C(F)F)c2cc(NN=C(C#N)C#N)cnc21]
TABLE 1-continued
47
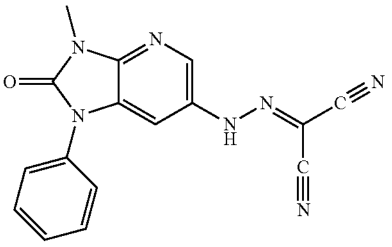 [SMILES: Cn1c(=O)n(-c2ccccc2)c2cc(NN=C(C#N)C#N)cnc21]
48
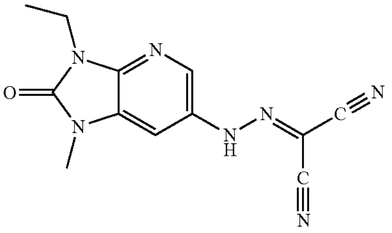 [SMILES: CCn1c(=O)n(C)c2cc(NN=C(C#N)C#N)cnc21]
49
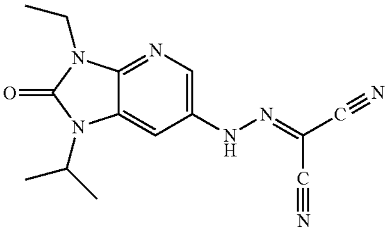 [SMILES: CCn1c(=O)n(C(C)C)c2cc(NN=C(C#N)C#N)cnc21]
50
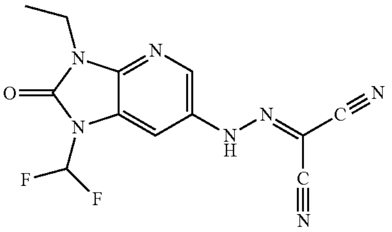 [SMILES: CCn1c(=O)n(C(F)F)c2cc(NN=C(C#N)C#N)cnc21]
51
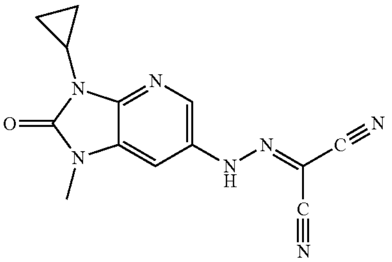 [SMILES: Cn1c(=O)n(C2CC2)c2ncc(NN=C(C#N)C#N)cc21]
52
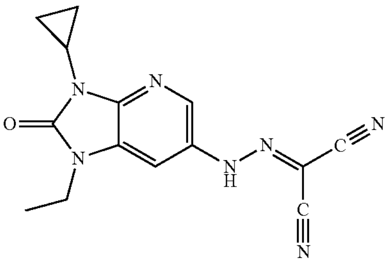 [SMILES: CCn1c(=O)n(C2CC2)c2ncc(NN=C(C#N)C#N)cc21]

TABLE 1-continued

| | |
|---|---|
| 53 | 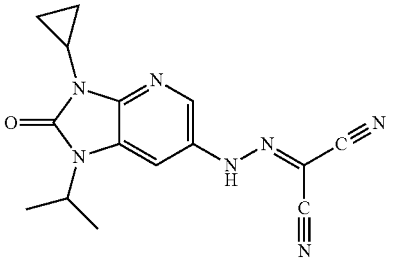 [SMILES: CC(C)n1c(=O)n(C2CC2)c2ncc(NN=C(C#N)C#N)cc21] |
| 54 | 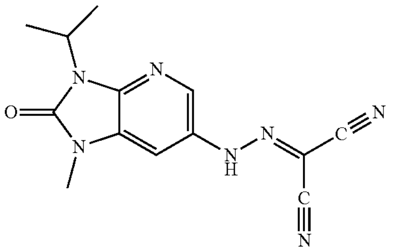 [SMILES: CC(C)n1c(=O)n(C)c2cc(NN=C(C#N)C#N)cnc21] |
| 55 | 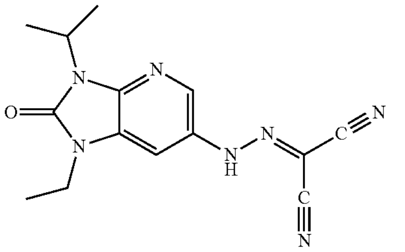 [SMILES: CCn1c(=O)n(C(C)C)c2ncc(NN=C(C#N)C#N)cc21] |
| 56 | 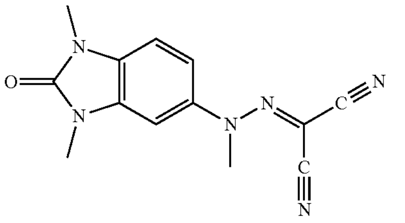 [SMILES: CN(N=C(C#N)C#N)c1ccc2c(c1)n(C)c(=O)n2C] |
| 57 | 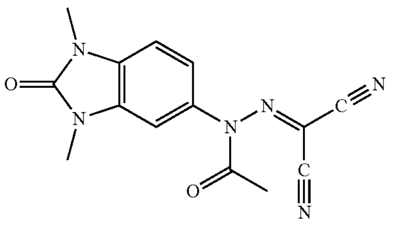 [SMILES: CC(=O)N(N=C(C#N)C#N)c1ccc2c(c1)n(C)c(=O)n2C] |

Meanwhile, the compounds of the present invention may exist in the form of a pharmaceutically acceptable salt. As the salt, an acid salt formed by a pharmaceutically acceptable free acid is useful. As used herein, the term "pharmaceutically acceptable salt" refers to any organic or inorganic addition salt of the compounds represented by Formulae 1 to 4 which is relatively non-toxic and harmless to patients, and side effects caused by this salt do not compromise the beneficial effects of this compound.

An acid addition salt is prepared by way of a conventional method, for example, by dissolving a compound in an excess amount of an aqueous acid solution and precipitating this solution using a water-miscible organic solvent such as methanol, ethanol, acetone, or acetonitrile. The same molar amounts of the compound and acid or alcohol (for example, glycol monoethyl ether) in water are heated, and subsequently the mixture may be evaporated and dried, or the precipitated salt may be suction-filtered.

In this case, as the free acid, an organic acid or an inorganic acid may be used. As the inorganic acid, hydrochloric acid, phosphoric acid, sulfuric acid, nitric acid, tartaric acid, or the like may be used. As the organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbon acid, vanillic acid, hydroiodic acid, or the like may be used. However, the present invention is not limited thereto.

Further, a pharmaceutically acceptable metal salt may be made using a base. An alkali metal salt or alkaline earth metal salt is obtained by dissolving the compound in an excess amount of an alkali metal hydroxide or alkaline earth metal hydroxide solution, filtering a non-soluble compound salt, and then evaporating and drying the filtrate. In this case, it is suitable for pharmaceutical use to prepare a sodium, potassium, or calcium salt as the metal salt, but the present invention is not limited thereto. Further, the corresponding silver salt may be obtained by reacting an alkali metal or alkaline earth metal salt with a suitable silver salt (for example, silver nitrate).

Pharmaceutically acceptable salts of the compounds of the present invention include salts of acidic or basic groups that may be present in the compounds of Formulae 1 to 4, unless otherwise indicated. For example, pharmaceutically acceptable salts may include sodium, calcium, and potassium salts of hydroxy groups, and other pharmaceutically acceptable salts of amino groups may include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate). These pharmaceutically acceptable salts may be prepared by way of preparation methods of salts known in the art.

As the salts of the compounds of Formulae 1 to 4 of the present invention, any salt, as a pharmaceutically acceptable salt, may be used without limitation as long as it exhibits pharmacological activity equivalent to the compounds of Formulae 1 to 4, for example, it inhibits the aggregation and/or hyperphosphorylation of tau protein.

Further, the compounds represented by Formulae 1 to 4 according to the present invention include, without limitation, pharmaceutically acceptable salts thereof, as well as solvates such as possible hydrates that may be prepared therefrom, and all possible stereoisomers. The solvates and stereoisomers of the compounds represented by Formulae 1 to 4 may be prepared from the compounds represented by Formulae 1 to 4 using any method known in the art.

Moreover, the compounds represented by Formulae 1 to 4 according to the present invention may be prepared in a crystalline or amorphous form, and may be optionally hydrated or solvated if prepared in a crystalline form. In the present invention, compounds containing various amounts of water as well as stoichiometric hydrates of the compounds represented by Formulae 1 to 4 may be provided. The solvates of the compounds represented by Formulae 1 to 4 according to the present invention include both stoichiometric solvates and non-stoichiometric solvates.

A second aspect of the present invention provides a method of preparing the compound of Formula 1.

For example, the compound of the present invention may be prepared by way of a process including:

a first step of reacting a compound represented by Formula 5 below including a reactive amine group at one end with sodium nitrite and malononitrile in the presence of an acid to form an imine bond; and optionally, a second step of introducing an $R_1$ substituent into a product obtained in the previous step when $R_1$ is a substituent other than hydrogen.

[Formula 5]

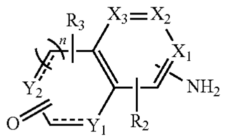

in Formula 5 above, $X_1$ to $X_3$, $Y_1$, $Y_2$, n, , $R_2$, and $R_3$ are as defined above, and when $Y_1$ and $Y_2$ are N(H), N(H) may be protected by tert-butoxycarbonyl.

In this regard, when N(H) of $Y_1$ and $Y_2$ is protected by tert-butoxycarbonyl, the process may further include a deprotection step after the reaction.

Specifically, the first step of the process may be performed by way of a series of processes including the steps of:

1-1) dissolving the compound of Formula 5 and sodium nitrite in a $C_{1-4}$ lower alcohol solvent and adding an aqueous acid solution thereto at a temperature of −5° C. to 5° C. to form a diazonium salt, 1-2) adding malononitrile to a reaction solution including the diazonium salt obtained in step 1-1) and performing a reaction at a temperature of 15° C. to 40° C., and 1-3) neutralizing the reaction solution of step 1-2) by adding an aqueous base solution thereto, without being limited thereto.

For example, the first step may be performed by performing the reaction of step 1-1) at a low temperature around 0° C. for 2 minutes to 1 hour using a 1 M hydrochloric acid solution, and then performing the reaction of step 1-2) at room temperature for 2 minutes to 1 hour, without being limited thereto.

For example, the second step may be performed by reacting the carbonohydrazonoyl dicyanide compound obtained in the previous step, in which $R_1$ is not substituted, with a halogenated derivative of $R_1$ in an organic solvent. Specifically, when $R_1$ is $C_{1-6}$ alkyl, the second step may be performed by dissolving the carbonohydrazonoyl dicyanide compound obtained in the previous step, in which $R_1$ is not substituted, in an organic solvent such as DMF, and adding a haloalkane such as alkane iodide corresponding to $R_1$ to the reaction solution, and performing a reaction at a temperature of 50° C. to 70° C., wherein the reaction solution may further include potassium tert-butoxide. However, the present invention is not limited thereto. Specifically, when $R_1$ is $C_{1-6}$ alkylcarbonyl, the second step may be performed by dissolving the carbonohydrazonoyl dicyanide compound obtained in the previous step, in which $R_1$ is not substituted, in a lower alcohol such as methanol, followed by reaction with a base such as potassium hydroxide and solidification to obtain a product, and reacting the product with a halogenated alkylcarbonyl such as acetyl chloride corresponding to the $C_{1-6}$ alkylcarbonyl in an organic solvent such as acetonitrile in the presence of triethylamine. However, the present invention is not limited thereto.

For example, the compound of Formula 5 used in the preparation of the compound of the present invention may be prepared from a compound represented by one of Formulae 5-a to 5-c below:

[Formula 5-a]

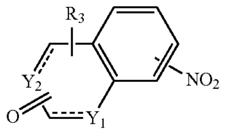

[Formula 5-b]

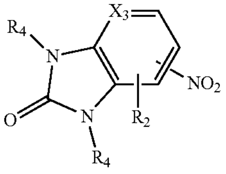

[Formula 5-c]

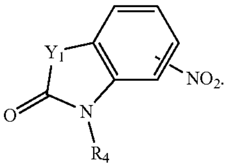

In Formula 5-b, each of the two $R_4$ may be selected from a series of the substituents defined above, and both $R_4$ may be the same, or one $R_4$ may be different from the other $R_4$.

Specifically, the method of the present invention may further include a step of reducing a nitro group of the compound represented by one of Formulae 5-a to 5-c into an amine group before the first step.

For example, the reduction may be performed via a reaction in an organic solvent such as a 1,4-dioxane or methanol solvent in the presence of a Pd/C catalyst, via a reaction with AcOH in the presence of Fe, or via a reaction with ammonium chloride in the presence of Fe, without being limited thereto.

Specifically, the compound represented by Formula 5-a may be prepared by reacting a precursor thereof, in which one of $Y_1$ and $Y_2$ is CH, and the other is O, with an amine-based compound $NH_2R_4$ in a state of being dissolved in an organic solvent, such that the O site is substituted with $NR_4$, but the compound is not limited thereto. For example, the reaction may be performed by stirring the precursor and ammonia or an $R_4$-substituted amine in an organic solvent such as THF or methanol at a temperature of 70° C. to 130° C. for 30 minutes to 5 hours, but is not limited thereto. In this regard, a microwave may be used for the stirring, without being limited thereto.

Furthermore, the precursor of the compound represented by Formula 5-a above, in which one of $Y_1$ and $Y_2$ is CH, and the other is O, may be prepared, optionally, by cyclization between a nitrobenzoic acid derivative and N,N-dimethylformamide dimethylacetal or acetal acetone, without being limited thereto. For example, the cydization may be performed by a reaction with N,N-dimethylformamide dimethylacetal in a DMF solvent or a reaction with acetal acetone in tert-butylalcohol in the presence of Cu. The reaction may be performed at a temperature of 100° C. to 130° C. for 2 to 24 hours while stirring, but is not limited thereto. In this regard, a microwave may be used for the stirring, without being limited thereto.

Specifically, in the method of the present invention, the compound represented by Formula 5-b or 5-c above may be prepared, optionally, by further performing a step of introducing an $R_4$ substituent via a reaction with a precursor compound including $R_4$ and a reactive halide. For example, the reaction with DBU (1,8-diazabicyclo[5.4.0]undec-7-ene) and $R_4$-halide or sodium $R_4$-haloacetate may be performed in a DMF solvent while stirring at room temperature for 6 to 24 hours, but is not limited thereto.

In addition, in the method of the present invention, the compound represented by Formula 5-b above may be prepared by way of cyclization between unsubstituted or $R_2$-substituted 1,2-diaminenitrophenyl and carbonyldiimidazole (CDI). For example, the reaction may be performed using a DMF solvent at room temperature for 6 to 24 hours, without being limited thereto.

For example, commercially available compounds may be used as purchased as reactants and intermediates used in each step of the method of the present invention, or the reactants and intermediates used in each step may be synthesized using commercially available compounds via reactions well known in the art alone or in combination, but the present invention is not limited thereto.

In addition, if required, the method may further include processes of isolating and/or purifying a product after each reaction, and these processes may be performed using various methods well known in the art.

A third aspect of the present invention is to provide a composition for inhibiting aggregation of tau protein including the compound of the present invention as an active ingredient.

A fourth aspect of the present invention is to provide a composition for inhibiting hyperphosphorylation of tau protein including the compound of the present invention as an active ingredient.

A fifth aspect of the present invention is to provide a pharmaceutical composition for preventing or treating a disease caused by aggregation or hyperphosphorylation of tau protein including the compound of the present invention as an active ingredient.

A sixth aspect of the present invention is to provide a method of preventing or treating a disease caused by aggregation or hyperphosphorylation of tau protein, the method including administering the compound of the present invention into a subject in need thereof.

In specific embodiments of the present invention, a total of 57 compounds, numbered 1 to 57 and represented by Formula 1, were newly synthesized, and the effects thereof on inhibiting aggregation and hyperphosphorylation of tau protein were confirmed. Moreover, in order to confirm the possibility of use as a pharmaceutical composition, it was confirmed that these compounds do not exhibit cytotoxicity.

As used herein, the term "prevention" refers to any action that inhibits or delays the occurrence, spread, and recurrence of a disease induced by aggregation or hyperphosphorylation of tau protein by administration of the pharmaceutical composition of the present invention, and the term "treatment" refers to any action in which symptoms of the disease are improved or beneficially changed by administration of the pharmaceutical composition of the present invention.

As described above, since the compound of the present invention not only inhibits aggregation or hyperphosphorylation of tau protein, but also does not exhibit toxicity to cells, the pharmaceutical composition containing this compound as an active ingredient may be used for the prevention or treatment of diseases caused by aggregation or hyperphosphorylation of tau protein. The disease caused by aggregation or hyperphosphorylation of tau protein to which the pharmaceutical composition of the present invention may be applied may be Alzheimer's disease, Parkinson's disease, vascular dementia, acute stroke, trauma, cerebrovascular disease, brain cord trauma, spinal cord trauma, peripheral neuropathy, retinopathy, glaucoma, or tauopathy. Non-limiting examples of the tauopathy may include chronic traumatic encephalopathy (CTE), primary age-related tauopathy, progressive supranuclear palsy, corticobasal degeneration, Pick's disease, argyrophilic grain disease (AGD), frontotemporal dementia (FTD), parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, post-traumatic stress disorder, and traumatic brain injury.

For example, the composition of the present invention may further include a pharmaceutically acceptable carrier, a diluent, or an excipient, may be formulated and used in various forms such as oral formulations such as powders, granules, tablets, capsules, suspensions, emulsions, syrups, aerosols, and injection drugs of sterile injection solutions according to a general method for each purpose of use, and may be administered orally or may be administered through various routes including intravenous, intraperitoneal, subcutaneous, rectal, and topical administrations. Examples of the suitable carrier, excipient, or diluent included in this composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The composition of the present invention may further include a filler, an anti-aggregating agent, a lubricant, a humectant, a flavoring agent, an emulsifying agent, a preservative, and the like.

Solid preparations for oral administration include tablets, pills, powders, granules, capsules, and the like, and such a solid preparation is formulated by mixing one or more excipients, such as starch, calcium carbonate, sucrose, lactose, and gelatin with the composition. Meanwhile, in addition to a simple excipient, a lubricant such as magnesium stearate or talc may be used.

As the oral liquid formulation, a suspension, a solution for internal use, an emulsion, a syrup, and the like may be exemplified, and the oral liquid formulation may include various excipients, such as a humectant, a sweetening agent, a fragrance, and a preservative in addition to water and liquid paraffin, which are commonly used as a simple diluent.

Preparations for parenteral administration include an aqueous solvent, a non-aqueous solvent, a suspension agent, an emulsifying agent, a lyophilized preparation, and a suppository, which are sterilized. As the non-aqueous solvent or the suspension agent, propylene glycol, polyethylene glycol, plant oil such as olive oil, injectable ester such as ethyloleate, or the like may be used. As a base of the suppository, witepsol, macrogol, twin 61, cacao oil, laurin oil, glycerogelatin, or the like may be used. Meanwhile, injectables may include conventional additives such as a solubilizing agent, an isotonic agent, a suspension agent, an emulsifying agent, a stabilizing agent, and a preservative.

The formulation may be prepared by way of a conventional mixing, granulating, or coating method, and may contain an active ingredient in an amount of about 0.1 wt % to 75 wt %, preferably about 0.1 wt % to 50 wt %. The unit formulation for a mammal weighing about 50 kg to 70 kg contains about 10 mg to 200 mg of an active ingredient.

In this case, the composition of the present invention is administered in a pharmaceutically effective amount. As used herein, the term “pharmaceutically effective amount” refers to an amount sufficient to treat a disease at a reasonable benefit/risk ratio applicable to medical treatment and not cause side effects, and the level of the effective amount may be determined depending on patients health status, type of disease, severity, activity of drug, sensitivity to drug, administration method, administration time, administration route, excretion rate, treatment period, factors including drugs used in combination or concurrently, and other factors well known in the medical field. The composition of the present invention may be administered as an individual therapeutic agent or administered in combination with other therapeutic agents, may be administered sequentially or simultaneously with a conventional therapeutic agent, and may be administered in a single dose or multiple doses. It is important to administer a minimum amount capable of obtaining the maximum effect without side effects in consideration of all of the above factors, which may be easily determined by those skilled in the art.

For example, since a dosage may increase or decrease depending on administration route, disease severity, sex, weight, age, and the like, the dosage does not limit the scope of the present invention in any way.

A preferred dosage of the compound of the present invention varies depending on the condition and weight of a patient, severity of disease, the form of drug, and the route and duration of administration, but may be appropriately selected by those skilled in the art. However, for a desired effect, the compound of the present invention may be administered in an amount of 0.0001 mg/kg to 100 mg/kg (body weight), preferably 0.001 mg/kg to 100 mg/kg (body weight) per day. The compound may be administered once a day or several times a day at divided doses via an oral or parenteral route.

A seventh aspect of the present invention is to provide a method for preventing or treating a disease caused by aggregation or hyperphosphorylation of tau protein, the method including administering the pharmaceutical composition of the present invention to a subject in need thereof.

As used herein, the term “subject” refers to any animal including monkeys, cows, horses, sheep, pigs, chickens, turkeys, quails, cats, dogs, mice, rabbits, and guinea pigs in addition to humans, which have developed or may develop a disease caused by aggregation or hyperphosphorylation of tau protein. The diseases may be effectively prevented or treated by administering the pharmaceutical composition of the present invention to the subject. Further, since the pharmaceutical composition of the present invention exhibits a therapeutic effect by inhibiting aggregation or hyperphosphorylation of tau protein, a synergistic effect may be exhibited by administering this composition in combination with a conventional therapeutic agent.

As used herein, the term “administration” refers to providing a predetermined substance to a patient by any suitable method, and the administration route of the composition of the present invention may be any general route as long as the substance is able to reach a target tissue. The composition may be administered through intraperitoneal administration, intravenous administration, intramuscular administration, subcutaneous administration, intradermal administration, oral administration, topical administration, intranasal administration, intrapulmonary administration, or rectal administration, but the present invention is not limited thereto. Also, the pharmaceutical composition of the present invention may be administered by any device capable of moving an active substance to a target cell. Preferred administrations and formulations include intravenous injection drugs, subcutaneous injection drugs, intradermal injection drugs, intramuscular injection drugs, and dropwise injection drugs. The injection drugs may be prepared using an aqueous solvent such as a physiological saline solution or Ringer’s solution, or a non-aqueous solvent such as plant oil, higher fatty acid ester (for example, ethyl oleate), or alcohol (for example, ethanol, benzyl alcohol, propylene glycol, or glycerin), and may include a pharmaceutical carrier such as a stabilizing agent for preventing denaturing (for example, ascorbic acid, sodium hydrogen sulfite, sodium pyrosulfite, BHA, tocopherol, or EDTA), an emulsifying agent, a buffering agent for pH control, or a preservative for inhibiting the growth of microorganisms (for example, phenylmercury nitrate, thimerosal, benzalkonium chloride, phenol, cresol, or benzyl alcohol).

MODE FOR INVENTION

Hereinafter, the present invention will be described in more detail with reference to examples and experimental examples. However, these examples and experimental examples are only illustrative of the present invention, and the scope of the present invention is not limited to these examples and experimental examples.

EXAMPLE 1: PREPARATION OF (1-OXO-1,2-DIHYDROISOQUINOLIN-7-YL)CARBONOHYDRAZONOYL DICYANIDE (COMPOUND 1)

Step 1-1: Preparation of 7-nitroisoquinolin-1(2H)-one

A 2.0 M ammonia solution (3.4 mL, 6.80 mmol) was added to 7-nitro-1H-isochromen-1-one (130 mg, 0.68 mmol) to obtain a reaction mixture, and the reaction mixture was stirred at 80° C. for 2 hours in a microwave. Upon completion of the reaction, a reaction product was solidified with distilled water and filtered to obtain 73 mg (yield: 56%) of the title compound.

$^1$H NMR (400 MHz, DMSO-$d_6$) δ 11.76 (s, 1H), 8.90 (d, J=2.5 Hz, 1H), 8.44 (dd, J=8.8 Hz, 2.5 Hz, 1H), 7.91 (d, J=8.7 Hz, 1H), 7.46 (d, J=7.1 Hz, 1H), 6.73 (d, J=7.1 Hz, 1H).

Step 1-2: Preparation of 7-aminoisoquinolin-1(2H)-one

7-Nitroisoquinolin-1(2H)-one (70 mg, 0.37 mmol) obtained in Step 1-1 was dissolved in 10% Pd/C (78 mg, 0.07 mmol) and 1,4-dioxane, and the reaction mixture was stirred at room temperature for 4 hours under a hydrogen atmosphere. Upon completion of the reaction, the reaction mixture was filtered, and the filtrate was concentrated under reduced pressure to obtain 27 mg (yield: 46%) of the title compound.

$^1$H NMR (400 MHz, DMSO-$d_6$) δ 10.82 (s, 1H), 7.40-7.20 (m, 2H), 6.97 (dd, J=8.4 Hz, 2.5 Hz, 1H), 6.80 (dd, J=7.0 Hz, 5.5 Hz, 1H), 6.34 (d, J=7.0 Hz, 1H), 5.47 (s, 2H).

Step 1-3: Preparation of (1-oxo-1,2-dihydroisoquinolin-7-yl)carbohydrazonoyl dicyanide 7-Aminoisoquinolin-1(2H)-one (20 mg, 0.12 mmol) obtained in Step 1-2 and sodium nitrite (13 mg, 0.19 mmol) were dissolved in ethanol under a nitrogen atmosphere, and a 1.0 M aqueous hydrochloric acid solution (0.4 mL, 0.37 mmol) was added thereto at 0° C. The reaction mixture was stirred at 0° C. for 10 minutes to form a diazonium salt. Malononitrile (16 mg, 0.25 mmol) was added to the reaction mixture including the diazonium salt, and the reaction mixture was stirred at room temperature for 10 minutes. The pH of the reaction mixture was adjusted to 6.0 using an aqueous sodium hydroxide solution and then further stirred at room temperature for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 20 mg (yield: 67%) of the title compound.

$^1$H NMR (400 MHz, DMSO-$d_6$) δ 13.22 (s, 1H), 11.33 (d, J=5.7 Hz, 1H), 8.24 (d, J=2.4 Hz, 1H), 7.81 (dd, J=8.7 Hz, 2.4 Hz, 1H), 7.72 (d, J=8.7 Hz, 1H), 7.16 (dd, J=7.1 Hz, 5.8 Hz, 1H), 6.56 (d, J=7.0 Hz, 1H).

EXAMPLE 2: PREPARATION OF (2-METHYL-1-OXO-1,2-DIHYDROISOQUINOLIN-7-YL)CARBONOHYDRAZONOYL DICYANIDE (COMPOUND 2)

Step 2-1: Preparation of 7-nitro-1H-Isochromen-1-one

2-Methyl-5-nitrobenzoic acid (500 mg, 2.76 mmol) was dissolved in dimethylformamide (DMF, 10 mL), and N,N-dimethylformamide dimethyl acetal (1.10 mL, 8.23 mmol) was added thereto, and the reaction mixture was stirred at 115° C. for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 65 mg (yield: 12%) of the title compound.

$^1$H NMR (400 MHz, DMSO-$d_6$) δ 8.79 (d, J=2.5 Hz, 1H), 8.61 (dd, J=8.6 Hz, 2.5 Hz, 1H), 7.93 (d, J=8.7 Hz, 1H), 7.80 (d, J=5.6 Hz, 1H), 7.01 (d, J=5.6 Hz, 1H).

Step 2-2: Preparation of 2-methyl-7-nitroisoquinolin-1(2H)-one 1.0 M methylamine (10.5 mL, 20.93 mmol) was added to 7-nitro-1H-isochromen-1-one (200 mg, 1.05 mmol) obtained in Step 2-1, and the reaction mixture was stirred at 120° C. for 12 hours. Upon completion of the reaction, a reaction product was extracted using distilled water and dichloromethane to obtain an organic layer, and the organic layer was dried over anhydrous magnesium sulfate and filtered. The filtrate was concentrated under reduced pressure, and the crude material was purified by column chromatography to obtain 126 mg (yield: 59%) of the title compound.

$^1$H NMR (400 MHz, DMSO-$d_6$) δ 8.90 (d, J=2.5 Hz, 1H), 8.43 (dd, J=8.8 Hz, 2.5 Hz, 1H), 7.89 (d, J=8.8 Hz, 1H), 7.75 (d, J=7.3 Hz, 1H), 6.78 (d, J=7.3 Hz, 1H), 3.55 (s, 3H).

Step 2-3: Preparation of 7-amino-2-methylisoquinolin-1(2H)-one 49 mg (yield: 57%) of the title compound was obtained in the same manner as in Step 1-2 of Example 1 above, except that 2-methyl-7-nitroisoquinolin-1(2H)-one (100 mg, 0.49 mmol) obtained in Step 2-2 above was used instead of 7-nitroisoquinolin-1(2H)-one.

$^1$H NMR (400 MHz, DMSO-$d_6$) δ 7.36-7.29 (m, 2H), 7.08 (d, J=7.2 Hz, 1H), 6.97 (dd, J=8.4 Hz, 2.5 Hz, 1H), 6.40 (d, J=7.2 Hz, 1H), 5.51 (s, 2H), 3.44 (s, 3H).

Step 2-4: Preparation of (2-methyl-1-oxo-1,2-dihydroisoquinolin-7-yl)carbohydrazonoyl dicyanide 49 mg (yield: 85%) of the title compound was obtained in the same manner as in Step 1-3 of Example 1 above, except that 7-amino-2-methylisoquinolin-1(2H)-one (40 mg, 0.23 mmol) obtained in Step 2-3 above was used instead of 7-aminoisoquinolin-1(2H)-one.

$^1$H NMR (400 MHz, DMSO-$d_6$) δ 13.25 (s, 1H), 8.28 (d, J=2.4 Hz, 1H), 7.81 (dd, J=8.7 Hz, 2.4 Hz, 1H), 7.72 (d, J=8.7 Hz, 1H), 7.46 (d, J=7.3 Hz, 1H), 6.63 (d, J=7.3 Hz, 1H), 3.52 (s, 3H).

EXAMPLE 3: PREPARATION OF (2-ISOPROPYL-1-OXO-1,2-DIHYDROISOQUINOLIN-7-YL) CARBONOHYDRAZONOYL DICYANIDE (COMPOUND 3)

Step 3-1: Preparation of 2-isopropyl-7-nitroisoquinolin-1(2H)-one

Isopropylamine (0.27 mL, 3.14 mmol) and methanol (3 mL) were added to 7-nitro-1H-isochromen-1-one (30 mg, 0.16 mmol) obtained in Step 2-1 of Example 2 above, and the reaction mixture was stirred at 80° C. for 12 hours in a microwave. Upon completion of the reaction, a reaction product was extracted using distilled water and ethyl acetate to obtain an organic layer, and the organic layer was dried over anhydrous magnesium sulfate and filtered. The filtrate was concentrated under reduced pressure and solidified with ether and hexane and filtered to obtain 20 mg (yield: 54%) of the title compound.

$^1$H NMR (400 MHz, Chloroform-d) δ 9.31 (d, J=2.4 Hz, 1H), 8.41 (dd, J=8.7 Hz, 2.4 Hz, 1H), 7.62 (d, J=8.7 Hz, 1H), 7.34 (d, J=7.6 Hz, 1H), 6.62 (d, J=7.5 Hz, 1H), 5.38 (p, J=6.8 Hz, 1H), 1.42 (d, J=6.8 Hz, 6H).

Step 3-2: Preparation of 7-amino-2-isopropylisoquinolin-1(2H)-one 54 mg (yield: 89%) of the title compound was obtained in the same manner as in Step 1-2 of Example 1 above, except that 2-isopropyl-7-nitroisoquinolin-1(2H)-one (70 mg, 0.30 mmol) obtained in Step 3-1 above was used instead of 7-nitroisoquinolin-1(2H)-one.

$^1$H NMR (400 MHz, DMSO-$d_6$) δ 9.31 (d, J=2.4 Hz, 1H), 8.41 (dd, J=8.7 Hz, 2.4 Hz, 1H), 7.62 (d, J=8.7 Hz, 1H), 7.34 (d, J=7.6 Hz, 1H), 6.62 (d, J=7.5 Hz, 1H), 5.38 (p, J=6.8 Hz, 1H), 1.42 (d, J=6.8 Hz, 6H).

Step 3-3: Preparation of (2-Isopropyl-1-oxo-1,2-dihydroisoquinolin-7-yl)carbohydrazonoyl dicyanide 30 mg (yield: 72%) of the title compound was obtained in the same manner as in Step 1-3 of Example 1 above, except that 7-amino-2-isopropylisoquinolin-1(2H)-one (30 mg, 0.15 mmol) obtained in Step 3-2 above was used instead of 7-aminoisoquinolin-1(2H)-one.

$^{1}$H NMR (400 MHz, DMSO-$d_6$) δ 13.25 (s, 1H), 8.30 (d, J=2.3 Hz, 1H), 7.81 (dd, J=8.7 Hz, 2.3 Hz, 1H), 7.72 (d, J=8.7 Hz, 1H), 7.52 (d, J=7.5 Hz, 1H), 6.69 (d, J=7.5 Hz, 1H), 5.19 (p, J=6.8 Hz, 1H), 1.33 (d, J=6.8 Hz, 6H).

EXAMPLE 4: PREPARATION OF (1-OXO-1,2-DIHYDROISOQUINOLIN-5-YL)CARBONOHYDRAZONOYL DICYANIDE (COMPOUND 4)

Step 4-1: Preparation of 5-nitro-1H-Isochromen-1-one 88 mg (yield: 42%) of the title compound was obtained in the same manner as in Step 2-1 of Example 2 above, except that 2-methyl-3-nitrobenzoic acid (200 mg, 1.10 mmol) was used instead of 2-methyl-5-nitrobenzoic acid.

$^{1}$H NMR (400 MHz, Chloroform-d) δ 8.69-8.61 (m, 1H), 8.49 (dd, J=8.1 Hz, 1.4 Hz, 1H), 7.68 (t, J=8.0 Hz, 1H), 7.44 (d, J=6.1 Hz, 1H), 7.38 (d, J=6.0 Hz, 1H).

Step 4-2: Preparation of 5-nitroisoquinolin-1(2H)-one 45 mg (yield: 45%) of the title compound was obtained in the same manner as in Step 1-1 of Example 1 above, except that 5-nitro-1H-isochromen-1-one (100 mg, 0.52 mmol) obtained in Step 4-1 above was used instead of 7-nitro-1H-isochromen-1-one.

$^{1}$H NMR (400 MHz, DMSO-$d_6$) δ 11.75 (s, 1H), 8.58 (d, J=8.0 Hz, 1H), 8.46 (dd, J=7.9 Hz, 1.4 Hz, 1H), 7.67 (t, J=8.0 Hz, 1H), 7.45 (d, J=7.6 Hz, 1H), 6.97 (d, J=7.6 Hz, 1H).

Step 4-3: Preparation of 5-amino-2-Isoquinolin-1(2H)-one 18 mg (yield: 42%) of the title compound was obtained in the same manner as in Step 1-2 of Example 1 above, except that 5-nitroisoquinolin-1(2H)-one (50 mg, 0.26 mmol) obtained in Step 4-2 above was used instead of 7-nitroisoquinolin-1(2H)-one.

$^{1}$H NMR (400 MHz, DMSO-$d_6$) δ 11.05 (s, 1H), 7.39 (d, J=7.9 Hz, 1H), 7.14 (t, J=7.8 Hz, 1H), 7.02 (dd, J=7.4 Hz, 4.8 Hz, 1H), 6.86 (dd, J=7.7 Hz, 1.2 Hz, 1H), 6.67 (d, J=7.4 Hz, 1H), 5.61 (s, 2H).

Step 4-4: Preparation of (1-oxo-1,2-dihydroisoquinolin-5-yl)carbohydrazonoyl dicyanide 6 mg (yield: 38%) of the title compound was obtained in the same manner as in Step 1-3 of Example 1 above, except that 5-amino-2-isoquinolin-1(2H)-one (30 mg, 0.15 mmol) obtained in Step 4-3 was used instead of 7-aminoisoquinolin-1(2H)-one.

$^{1}$H NMR (400 MHz, DMSO-$d_6$) δ 11.42 (s, 1H), 8.10 (d, J=7.9 Hz, 1H), 7.69 (dd, J=7.8 Hz, 1.3 Hz, 1H), 7.50 (t, J=7.9 Hz, 1H), 7.27 (dd, J=7.3 Hz, 5.8 Hz, 1H), 6.82 (d, J=7.4 Hz, 1H).

EXAMPLE 5: PREPARATION OF (2-METHYL-1-OXO-1,2-DIHYDROISOQUINOLIN-5-YL)CARBONOHYDRAZONOYL DICYANIDE (COMPOUND 5)

Step 5-1: Preparation of 2-methyl-5-nitroisoquinolin-1(2H)-one 37 mg (yield: 47%) of the title compound was obtained in the same manner as in Step 2-2 of Example 2 above, except that 5-nitro-1H-isochromen-1-one (74 mg, 0.39 mmol) was used instead of 7-nitro-1H-isochromen-1-one.

$^{1}$H NMR (400 MHz, DMSO-$d_6$) δ 8.61 (d, J=7.9 Hz, 1H), 8.47 (dd, J=7.9 Hz, 1.3 Hz, 1H), 7.74 (d, J=7.8 Hz, 1H), 7.68 (t, J=8.0 Hz, 1H), 7.03 (dd, J=7.7 Hz, 0.8 Hz, 1H), 3.55 (s, 3H).

Step 5-2: Preparation of 5-amino-2-methylisoquinolin-1(2H)-one 30 mg (yield: 69%) of the title compound was obtained in the same manner as in Step 1-2 of Example 1 above, except that 2-methyl-5-nitroisoquinolin-1(2H)-one (50 mg, 0.24 mmol) obtained in Step 5-1 was used instead of 7-nitroisoquinolin-1(2H)-one.

$^{1}$H NMR (400 MHz, DMSO-$d_6$) δ 7.42 (d, J=7.9 Hz, 1H), 7.32 (d, J=7.5 Hz, 1H), 7.16 (t, J=7.8 Hz, 1H), 6.84 (dd, J=7.8 Hz, 1.2 Hz, 1H), 6.73 (d, J=7.6 Hz, 1H), 5.64 (s, 2H), 3.46 (s, 3H).

Step 5-3: Preparation of (2-methyl-1-oxo-1,2-dihydroisoquinolin-5-yl)carbohydrazonoyl dicyanide 31 mg (yield: 86%) of the title compound was obtained in the same manner as in Step 1-3 of Example 1 above, except that 5-amino-2-methylisoquinolin-1(2H)-one (25 mg, 0.14 mmol) obtained in Step 5-2 was used instead of 7-aminoisoquinolin-1(2H)-one.

$^{1}$H NMR (400 MHz, Chloroform-d) δ 9.87 (s, 1H), 8.38 (d, J=8.0 Hz, 1H), 7.81 (dd, J=8.0 Hz, 1.2 Hz, 1H), 7.55 (t, J=8.0 Hz, 1H), 7.24 (d, J=7.7 Hz, 1H), 6.46 (d, J=7.6 Hz, 1H), 3.64 (s, 3H).

EXAMPLE 6: PREPARATION OF (2-ISOPROPYL-1-OXO-1,2-DIHYDROISOQUINOLIN-5-YL) CARBONOHYDRAZONOYL DICYANIDE (COMPOUND 6)

Step 6-1: Preparation of 2-isopropyl-6-nitroisoquinolin-1(2H)-one 11 mg (yield: 30%) of the title compound was obtained in the same manner as in Step 3-1 of Example 3 above, except that 5-nitro-1H-isochromen-1-one (30 mg, 0.16 mmol) was used instead of 7-nitro-1H-isochromen-1-one.

$^{1}$H NMR (400 MHz, Chloroform-d) δ 8.80 (dd, J=8.0 Hz, 1.4 Hz, 1H), 8.40 (dd, J=8.0 Hz, 1.4 Hz, 1H), 7.56 (t, J=8.0 Hz, 1H), 7.35 (s, 2H), 5.35 (p, J=6.6 Hz, 1H), 1.42 (d, J=6.8 Hz, 6H).

Step 6-2: Preparation of 6-amino-2-Isopropylisoquinolin-1(2H)-one 34 mg (yield: 99%) of the title compound was obtained in the same manner as in Step 1-2 of Example 1 above, except that 2-isopropyl-5-nitroisoquinolin-1(2H)-one (40 mg, 0.17 mmol) obtained in Step 6-1 above was used instead of 7-nitroisoquinolin-1(2H)-one.

$^{1}$H NMR (400 MHz, Chloroform-d) δ 7.92 (d, J=8.1 Hz, 1H), 7.29 (d, J=7.9 Hz, 1H), 7.13 (d, J=7.7 Hz, 1H), 6.94 (dd, J=7.6 Hz, 1.2 Hz, 1H), 6.55-6.42 (m, 1H), 5.40 (p, J=6.9 Hz, 1H), 3.95 (s, 2H), 1.38 (d, J=6.9 Hz, 6H).

Step 6-3: Preparation of (2-Isopropyl-1-oxo-1,2-dihydroisoquinolin-5-yl)carbohydrazonoyl dicyanide 22 mg (yield: 79%) of the title compound was obtained in the same manner as in Step 1-3 of Example 1 above, except that 5-amino-2-isopropylisoquinolin-1(2H)-one (20 mg, 0.10 mmol) obtained in Step 6-2 was used instead of 7-aminoisoquinolin-1(2H)-one.

$^1$H NMR (400 MHz, DMSO-$d_6$) δ 8.14 (d, J=8.0 Hz, 1H), 7.72-7.58 (m, 2H), 7.51 (t, J=7.9 Hz, 1H), 6.96 (d, J=7.8 Hz, 1H), 5.18 (p, J=6.8 Hz, 1H), 1.34 (d, J=6.8 Hz, 6H).

EXAMPLE 7: PREPARATION OF (2,3-DIMETHYL-1-OXO-1,2-DIHYDROISOQUINOLIN-5-YL)CARBONOHYDRAZONOYL DICYANIDE (COMPOUND 7)

Step 7-1: Preparation of 3-methyl-6-nitro-1H-isochromen-1-one

Acetylacetone (1.04 mL, 10.16 mmol), copper (13 mg, 0.20 mmol), potassium tert-butoxide (456 mg, 4.06 mmol), and tert-butylalcohol (10 mL) were added to 2-bromo-3-nitrobenzoic acid (500 mg, 2.03 mmol), and the reaction mixture was stirred at 110° C. for 5 hours in a microwave. Upon completion of the reaction, the reaction mixture was acidified by adding an aqueous hydrochloric acid solution to the reaction mixture, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 68 mg (yield: 16%) of the title compound.

$^1$H NMR (400 MHz, Chloroform-d) δ 8.58 (dt, J=7.8 Hz, 1.1 Hz, 1H), 8.44 (dd, J=8.2 Hz, 1.4 Hz, 1H), 7.57 (t, J=8.0 Hz, 1H), 7.16 (t, J=1.0 Hz, 1H), 2.38 (d, J=1.0 Hz, 3H).

Step 7-2: Preparation of 2,3-dimethyl-5-nitroisoquinolin-1(2H)-one 56 mg (yield: 88%) of the title compound was obtained in the same manner as in Step 2-2 of Example 2 above, except that 3-methyl-5-nitro-1H-isochromen-1-one (60 mg, 0.29 mmol) obtained in Step 7-1 was used instead of 7-nitro-1H-isochromen-1-one.

$^1$H NMR (400 MHz, DMSO-$d_6$) δ 8.26 (d, J=7.8 Hz, 1H), 8.18 (d, J=8.2 Hz, 1H), 7.62 (t, J=7.9 Hz, 1H), 6.23 (d, J=1.0 Hz, 1H), 3.02 (s, 3H), 1.46 (s, 3H).

Step 7-3: Preparation of 5-amino-2,3-dimethylisoquinoline-1(2H)-one 13 mg (yield: 29%) of the title compound was obtained in the same manner as in Step 1-2 of Example 1 above, except that 2,3-dimethyl-5-nitroisoquinolin-1(2H)-one (50 mg, 0.23 mmol) obtained in Step 7-2 was used instead of 7-nitroisoquinolin-1(2H)-one.

$^1$H NMR (400 MHz, DMSO-da) δ 7.38 (d, J=7.9 Hz, 1H), 7.08 (t, J=7.8 Hz, 1H), 6.81 (dd, J=7.7 Hz, 1.2 Hz, 1H), 6.64 (s, 1H), 5.51 (s, 2H), 3.48 (s, 3H), 2.39 (d, J=1.0 Hz, 3H).

Step 7-4: Preparation of (2,3-dimethyl-1-oxo-1,2-dihydroisoquinolin-5-yl)carbohydrazonoyl dicyanide 13 mg (yield: 92%) of the title compound was obtained in the same manner as in Step 1-3 of Example 1 above, except that 5-amino-2,3-dimethylisoquinolin-1(2H)-one (10 mg, 0.05 mmol) obtained in Step 7-3 was used instead of 7-aminoisoquinolin-1(2H)-one.

$^1$H NMR (400 MHz, DMSO-$d_6$) δ 8.11 (d, J=8.0 Hz, 1H), 7.65 (dd, J=7.8 Hz, 1.3 Hz, 1H), 7.44 (t, J=7.9 Hz, 1H), 6.78 (s, 1H), 3.54 (s, 3H), 2.47 (s, 3H).

EXAMPLE 8: PREPARATION OF (2-OXO-1,2-DIHYDROQUINOLIN-6-YL) CARBONOHYDRAZONOYL DICYANIDE (COMPOUND 8)

Step 8-1: Preparation of 6-aminoisoquinolin-2(1H)-one 34 mg (yield: 13%) of the title compound was obtained in the same manner as in Step 1-2 of Example 1 above, except that 6-nitroisoquinolin-2(1H)-one (300 mg, 1.58 mmol) was used instead of 7-nitroisoquinolin-1(2H)-one.

$^1$H NMR (400 MHz, DMSO-$d_6$) δ 11.36 (s, 1H), 7.66 (d, J=9.5 Hz, 1H), 7.02 (s, 1H), 6.83 (dd, J=8.7 Hz, 2.5 Hz, 1H), 6.71 (d, J=2.5 Hz, 1H), 6.36 (d, J=9.5 Hz, 1H), 4.98 (s, 2H).

Step 8-2: Preparation of (2-oxo-1,2-dihydroisoquinolin-6-yl)carbohydrazonoyl dicyanide 17 mg (yield: 59%) of the title compound was obtained in the same manner as in Step 1-3 of Example 1 above, except that 6-aminoisoquinolin-2(1H)-one (20 mg, 0.12 mmol) obtained in Step 8-1 was used instead of 7-aminoisoquinolin-1(2H)-one.

$^1$H NMR (400 MHz, DMSO-$d_6$) δ 13.13 (s, 1H), 11.87 (s, 1H), 7.97 (d, J=9.6 Hz, 1H), 7.74 (s, 1H), 7.66 (dd, J=8.9 Hz, 2.4 Hz, 1H), 7.34 (d, J=8.9 Hz, 1H), 6.55 (d, J=9.6 Hz, 1H).

EXAMPLE 9: PREPARATION OF (6-FLUORO-1,3-DIMETHYL-2-OXO-2,3-DIHYDRO-1H-BENZO[D]IMIDAZOL-5-YL)CARBONOHYDRAZONOYL DICYANIDE (COMPOUND 9)

Step 9-1: Preparation of 5-fluoro-6-nitro-1H-benzo[d]imidazol-2(3H)-one

4-Fluoro-5-nitrobenzene-1,2-diamine (500 mg, 2.92 mmol) and carbonyldiimidazole (CDI, 1.44 g, 8.77 mmol) were dissolved in DMF under a nitrogen atmosphere, and the reaction mixture was stirred at room temperature for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 512 mg (yield: 89%) of the title compound.

$^1$H NMR (400 MHz, Acetone-$d_6$) δ 10.38 (s, 1H), 10.08 (s, 1H), 7.75 (d, J=6.4 Hz, 1H), 7.09 (d, J=11.2 Hz, 1H).

Step 9-2: Preparation of 5-fluoro-1,3-dimethyl-6-nitro-1H-benzo[d]imidazol-2(3H)-one After 5-fluoro-6-nitro-1H-benzo[d]imidazol-2(3H)-one (450 mg, 2.28 mmol) obtained in Step 9-1 was dissolved in DMF under a nitrogen atmosphere, 1,8-diazabicyclo[5.4.0]undec-7-ene (DBU, 1.02 mL, 6.84 mmol) and methyl iodide (0.42 mL, 6.84 mmol) were added thereto, and the reaction mixture was stirred at room temperature for 1 to 5 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 328 mg (yield: 64%) of the title compound.

$^1$H NMR (400 MHz, Acetone-do) δ 7.85 (d, J=6.4 Hz, 1H), 7.26 (d, J=11.6 Hz, 1H), 3.49 (s, 3H), 3.46 (s, 3H).

Step 9-3: Preparation of 5-amino-6-fluoro-1,3-dimethyl-1H-benzo[d]imidazol-2(3H)-one 5-Fluoro-1,3-dimethyl-6-nitro-1H-benzo[d]imidazol-2(3H)-one (250 mg, 1.11 mmol) obtained in Step 9-2 and iron (496 mg, 8.88 mmol) were dissolved in acetic acid under a nitrogen atmosphere, and the reaction mixture was stirred at room temperature for 12 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 190 mg (yield: 88%) of the title compound.

$^1$H NMR (400 MHz, Acetone-$d_6$) δ 6.84 (d, J=10.8 Hz, 1H), 6.59 (d, J=7.6 Hz, 1H), 4.36 (s, 2H), 3.28 (s, 3H), 3.26 (s, 3H).

Step 9-4: Preparation of (6-fluoro-1,3-dimethyl-2-oxo-2,3-dihydro-1H-benzo[d]imidazol-5-vi)carbonohydrazonoyl dicyanide 5-Amino-6-fluoro-1,3-dimethyl-1H-benzo[d]imidazol-2(3H)-one (100 mg, 0.51 mmol) obtained in Step 9-3 and a 35% aqueous hydrochloric acid solution (0.2 mL) were dissolved in distilled water under a nitrogen atmosphere and sodium nitrite (65 mg, 0.77 mmol) was added thereto at 0° C. The reaction mixture was stirred at 0° C. for 30 minutes to form a diazonium salt. Malononitrile (51 mg, 0.77 mmol) was added to the reaction mixture including the diazonium salt, and the reaction mixture was stirred at room temperature for 11 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 28 mg (yield: 20%) of the title compound.

$^1$H NMR (400 MHz, Acetone-do) δ 7.36 (d, J=6.8 Hz, 1H), 7.15 (d, J=10.8 Hz, 1H), 3.43 (s, 3H), 3.39 (s, 3H).

EXAMPLE 10: PREPARATION OF (6-CHLORO-1,3-DIMETHYL-2-OXO-2,3-DIHYDRO-1H-BENZO[D]IMIDAZOL-5-YL)CARBONOHYDRAZONOYL DICYANIDE (COMPOUND 10)

Step 10-1: Preparation of 5-chloro-6-nitro-1H-benzo[d]imidazol-2(3H)-one 882 mg (yield: 77%) of the title compound was obtained in the same manner as in Step 9-1 of Example 9 above, except that 4-chloro-5-nitrobenzene-1,2-diamine (1 g, 5.33 mmol) was used instead of 4-fluoro-5-nitrobenzene-1,2-diamine.

$^1$H NMR (400 MHz, Acetone-$d_6$) δ 10.30 (s, 1H), 10.19 (s, 1H), 7.71 (s, 1H), 7.26 (s, 1H).

Step 10-2: Preparation of 5-chloro-1,3-dimethyl-6-nitro-1H-benzo[d]imidazol-2(3H)-one 410 mg (yield: 73%) of the title compound was obtained in the same manner as in Step 9-2 of Example 9 above, except that 5-chloro-6-nitro-1H-benzo[d]imidazol-2(3H)-one (500 mg, 2.34 mmol) obtained in Step 10-1 was used instead of 5-fluoro-6-nitro-1H-benzo[d]imidazol-2(3H)-one.

$^1$H NMR (400 MHz, Acetone-do) δ 7.83 (s, 1H), 7.41 (s, 1H), 3.48 (s, 3H), 3.47 (s, 3H).

Step 10-3: Preparation of 5-amino-6-chloro-1,3-dimethyl-1H-benzo[d]imidazol-2(3H)-one 190 mg (yield: 88%) of the title compound was obtained in the same manner as in Step 9-3 of Example 9 above, except that 5-chloro-1,3-dimethyl-6-nitro-1H-benzo[d]imidazol-2(3H)-one (250 mg, 1.03 mmol) obtained in Step 10-2 was used instead of 5-fluoro-1,3-dimethyl-6-nitro-1H-benzo[d]imidazol-2(3H)-one.

$^1$H NMR (400 MHz, Acetone-$d_6$) δ 6.84 (d, J=10.8 Hz, 1H), 6.59 (d, J=7.6 Hz, 1H), 4.36 (s, 2H), 3.28 (s, 3H), 3.26 (s, 3H).

Step 10-4: Preparation of (6-chloro-1,3-dimethyl-2-oxo-2,3-dihydro-1H-benzo[d]imidazol-6-yl)carbonohydrazonoyl dicyanide 28 mg (yield: 20%) of the title compound was obtained in the same manner as in Step 9-4 of Example 9 above, except that 5-amino-6-chloro-1,3-dimethyl-1H-benzo[d]imidazol-2(3H)-one (100 mg, 0.51 mmol) obtained in Step 10-3 was used instead of 5-amino-6-fluoro-1,3-dimethyl-1H-benzo[d]imidazol-2(3H)-one.

$^1$H NMR (400 MHz, DMSO-$d_6$) δ 7.39 (s, 1H), 7.30 (s, 1H), 3.34 (s, 3H), 3.33 (s, 3H).

EXAMPLE 11: PREPARATION OF (7-CHLORO-1,3-DIMETHYL-2-OXO-2,3-DIHYDRO-1H-BENZO[D]IMIDAZOL-5-YL)CARBONOHYDRAZONOYL DICYANIDE (COMPOUND 11)

Step 11-1: Preparation of 4-chloro-6-nitro-1H-benzo[d]imidazol-2(3H)-one 720 mg (yield: 63%) of the title compound was obtained in the same manner as in Step 9-1 of Example 9 above, except that 3-chloro-5-nitrobenzene-1,2-diamine (2.63 g, 15.99 mmol) was used instead of 4-fluoro-5-nitrobenzene-1,2-diamine.

$^1$H NMR (400 MHz, Acetone-$d_6$) δ 10.77 (s, 1H), 10.40 (s, 1H), 8.01 (d, J=2.0 Hz, 1H), 7.86 (d, J=2.0 Hz, 1H).

Step 11-2: Preparation of 4-chloro-1,3-dimethyl-6-nitro-1H-benzo[d]imidazol-2(3H)-one 412 mg (yield: 73%) of the title compound was obtained in the same manner as in Step 9-2 of Example 9 above, except that 4-chloro-6-nitro-1H-benzo[d]imidazol-2(3H)-one (500 mg, 2.34 mmol) obtained in Step 11-1 was used instead of 5-fluoro-6-nitro-1H-benzo[d]imidazol-2(3H)-one.

$^1$H NMR (400 MHz, Acetone-$d_6$) δ 7.99 (d, J=2.0 Hz, 1H), 7.95 (d, J=2.4 Hz, 1H), 3.75 (s, 3H), 3.53 (s, 3H).

Step 11-3: Preparation of 6-amino-4-chloro-1,3-dimethyl-1H-benzo[d]imidazol-2(3H)-one 154 mg (yield: 71%) of the title compound was obtained in the same manner as in Step 9-3 of Example 9 above, except that 4-chloro-1,3-dimethyl-6-nitro-1H-benzo[d]imidazol-2(3H)-one (250 mg, 1.03 mmol) obtained in Step 11-2 was used instead of 5-fluoro-1,3-dimethyl-6-nitro-1H-benzo[d]imidazol-2(3H)-one.

$^1$H NMR (400 MHz, Acetone-$d_6$) δ 6.39 (d, J=2.0 Hz, 1H), 6.37 (d, J=2.0 Hz, 1H), 4.64 (s, 2H), 3.55 (s, 3H), 3.26 (s, 3H).

Step 11-4: Preparation of (7-chloro-1,3-dimethyl-2-oxo-2,3-dihydro-1H-benzo[d]imidazol-5-yl)carbonohydrazonoyl dicyanide 42 mg (yield: 41%) of the title compound was obtained in the same manner as in Step 9-4 of Example 9 above, except that 6-amino-4-chloro-1,3-dimethyl-1H-benzo[d]imidazol-2(3H)-one (100 mg, 0.47 mmol) obtained in Step 11-3 was used instead of 5-amino-6-fluoro-1,3-dimethyl-1H-benzo[d]imidazol-2(3H)-one.

$^1$H NMR (400 MHz, DMSO-$d_6$) δ 7.20 (s, 2H), 3.58 (s, 3H).

EXAMPLE 12: PREPARATION OF (1,3-DIMETHYL-2-OXO-2,3-DIHYDRO-1H-IMIDAZO[4,5-B]PYRIDIN-6-YL)CARBONOHYDRAZONOYL DICYANIDE (COMPOUND 12)

Step 12-1: Preparation of 6-nitro-1H-imidazo[4,5-b]pyridin-2(3H)-one

5-Nitropyridine-2,3-diamine (600 mg, 3.89 mmol) and N,N'-disuccinimidyl carbonate (15 g, 5.84 mmol) were dissolved in acetonitrile under a nitrogen atmosphere, and the reaction mixture was stirred at 80° C. for 8 hours. Upon completion of the reaction, a reaction product was filtered using acetonitrile to obtain 570 mg (yield: 81%) of the title compound.

$^1$H NMR (400 MHz, Acetone-$d_6$) δ 11.00 (s, 1H), 10.29 (s, 1H), 8.87 (d, J=2.4 Hz, 1H), 8.02 (d, J=2.4 Hz, 1H).

Step 12-2: Preparation of 1,3-dimethyl-6-nitro-1H-imidazo[4,5-b]pyridin-2(3H)-one 351 mg (yield: 76%) of the title compound was obtained in the same manner as in Step 9-2 of Example 9 above, except that 6-nitro-1H-imidazo[4,5-b]pyridin-2(3H)-one (400 mg, 2.22 mmol) obtained in Step 12-1 was used instead of 5-fluoro-6-nitro-1H-benzo[d]imidazol-2(3H)-one.

$^1$H NMR (400 MHz, Acetone-$d_6$) δ 8.94 (d, J=2.4 Hz, 1H), 8.18 (d, J=2.0 Hz, 1H), 3.54 (s, 3H), 3.48 (s, 3H).

Step 12-3: Preparation of 6-amino-1,3-dimethyl-1H-imidazo[4,5-b]pyridin-2(3H)-one 1,3-Dimethyl-6-nitro-1H-imidazo[4,5-b]pyridin-2(3H)-one (300 mg, 1.44 mmol) obtained in Step 12-2 and 10% Pd/C (307 mg, 0.29 mmol) were dissolved in methanol, and the reaction mixture was stirred at room temperature for 2 hours. Upon completion of the reaction, a reaction product was filtered using methanol, and the filtrate was concentrated to obtain 241 mg (yield: 94%) of the title compound.

$^1$H NMR (400 MHz, Acetone-$d_6$) δ 7.49 (d, J=2.4 Hz, 1H), 6.78 (d, J=2.4 Hz, 1H), 4.49 (s, 2H), 3.30 (s, 3H), 3.29 (s, 3H).

Step 12-4: Preparation of (1,3-dimethyl-2-oxo-2,3-dihydro-1H-imidazo[4,5-b]pyridin-6-yl)carbonohydrazonoyl dicyanide 100 mg (yield: 47%) of the title compound was obtained in the same manner as in Step 9-4 of Example 9 above, except that 6-amino-1,3-dimethyl-1H-imidazo[4,5-b]pyridin-2(3H)-one (150 mg, 0.84 mmol) obtained in Step 12-3 was used instead of 5-amino-6-fluoro-1,3-dimethyl-1H-benzo[d]imidazol-2(3H)-one.

$^1$H NMR (400 MHz, Acetone-$d_6$) δ 8.18 (d, J=2.0 Hz, 1H), 7.63 (d, J=2.0 Hz, 1H), 3.47 (s, 3H), 3.41 (s, 3H).

EXAMPLE 13: PREPARATION OF (2-OXO-2,3-DIHYDROBENZO[D]THIAZOL-6-YL)CARBONOHYDRAZONOYL DICYANIDE (COMPOUND 13)

Step 13-1: Preparation of 6-aminobenzo[d]thiazol-2(3H)-one

6-Nitrobenzo[d]thiazol-2(3H)-one (200 mg, 1.02 mmol) was dissolved in ethanol/water under a nitrogen atmosphere, Fe (228 mg, 4.08 mmol) and ammonium chloride (545 mg, 10.19 mmol) were added thereto, and the reaction mixture was stirred at 80° C. for 1 hour. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was purified by column chromatography to obtain 83 mg (yield: 49%) of the title compound.

$^1$H NMR (400 MHz, DMSO-$d_6$) δ 11.34 (s, 1H), 6.79 (d, J=8.4 Hz, 1H), 6.69 (d, J=2.2 Hz, 1H), 6.51 (dd, J=8.5 Hz, 2.3 Hz, 1H), 4.95 (s, 2H).

Step 13-2: Preparation of (2-oxo-2,3-dihydrobenzo[d]thiazol-6-yl)carbonohydrazonoyl dicyanide 34 mg (yield: 47%) of the title compound was obtained in the same manner as in Step 9-4 of Example 9 above, except that 6-aminobenzo[d]thiazol-2(3H)-one (50 mg, 0.30 mmol) obtained in Step 13-1 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 11.96 (s, 1H), 7.68 (s, 1H), 7.39 (d, J=8.8 Hz, 1H), 7.13 (d, J=8.6 Hz, 1H).

EXAMPLE 14: PREPARATION OF (3-METHYL-2-OXO-2,3-DIHYDROBENZO[D]THIAZOL-6-YL)CARBONOHYDRAZONOYL DICYANIDE (COMPOUND 14)

Step 14-1: Preparation of 3-methyl-6-nitrobenzo[d]thiazol-2(3H)-one 68 mg (yield: 64%) of the title compound was obtained in the same manner as in Step 9-2 of Example 9 above, except that 6-nitrobenzo[d]thiazol-2(3H)-one (100 mg, 0.48 mmol) was used instead of 5-fluoro-6-nitro-1H-benzo[d]imidazol-2(3H)-one.

$^1$H NMR (400 MHz, Acetone-$d_6$) δ 8.61 (d, J=2.4 Hz, 1H), 8.31 (dd, J=8.9 Hz, 2.4 Hz, 1H), 7.50 (d, J=8.9 Hz, 1H), 3.58 (s, 3H).

Step 14-2: Preparation of 6-amino-3-methylbenzo[d]thiazol-2(3H)-one 79 mg (yield: 91%) of the title compound was obtained in the same manner as in Step 1-2 of Example 1 above, except that 3-methyl-6-nitrobenzo[d]thiazol-2(3H)-one (100 mg, 0.48 mmol) obtained in Step 14-1 was used instead of 7-nitroisoquinolin-1(2H)-one, and methanol was used as a solvent instead of 1,4-dioxane.

$^1$H NMR (400 MHz, Acetone-$d_6$) δ 6.95 (d, J=8.5 Hz, 1H), 6.87 (d, J=2.3 Hz, 1H), 6.72 (dd, J=8.5 Hz, 2.3 Hz, 1H), 4.62 (s, 2H), 3.35 (s, 3H).

Step 14-3: Preparation of (3-methyl-2-oxo-2,3-dihydrobenzo[d]thiazol-6-yl)carbonohydrazonoyl dicyanide 94 mg (yield: 83%) of the title compound was obtained in the same manner as in Step 9-4 of Example 9 above, except that 6-amino-3-methylbenzo[d]thiazol-2(3H)-one obtained in Step 14-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.81 (d, J=2.2 Hz, 1H), 7.51 (dd, J=8.8 Hz, 2.3 Hz, 1H), 7.36 (d, J=8.8 Hz, 1H), 3.41 (s, 3H).

EXAMPLE 15: PREPARATION OF (2-OXO-2,3-DIHYDROBENZO[D]OXAZOL-6-YL)CARBONOHYDRAZONOYL DICYANIDE (COMPOUND 16)

Step 15-1: Preparation of 6-aminobenzo[d]oxazol-2(3H)-one 131 mg (yield: 78%) of the title compound was obtained in the same manner as in Step 14-2 of Example 14 above, except that 6-nitrobenzo[d]oxazol-2(3H)-one was used instead of 3-methyl-6-nitrobenzo[d]thiazol-2(3H)-one.

$^1$H NMR (400 MHz, Acetone-$d_6$) δ 6.83 (d, J=8.3 Hz, 1H), 6.61 (d, J=2.1 Hz, 1H), 6.49 (dd, J=8.3 Hz, 2.1 Hz, 1H), 4.60 (s, 2H).

Step 15-2: Preparation of (2-oxo-2,3-dihydrobenzo[d]oxazol-6-yl)carbonohydrazonoyl dicyanide 115 mg (yield: 76%) of the title compound was obtained in the same manner as in Step 9-4 of Example 9 above, except that 6-aminobenzo[d]oxazol-2(3H)-one obtained in Step 15-1 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 11.77 (s, 1H), 7.40 (d, J=2.0 Hz, 1H), 7.30 (dd, J=8.4 Hz, 2.0 Hz, 1H), 7.13 (d, J=8.4 Hz, 1H).

EXAMPLE 16: PREPARATION OF (3-METHYL-2-OXO-2,3-DIHYDROBENZO[D]OXAZOL-6-YL)CARBONOHYDRAZONOYL DICYANIDE (COMPOUND 16)

Step 16-1: Preparation of 3-methyl-6-nitrobenzo[d]oxazol-2(3H)-one 282 mg (yield: 87%) of the title compound was obtained in the same manner as in Step 9-2 of Example 9 above, except that 6-nitrobenzo[d]oxazol-2(3H)-one was used instead of 5-fluoro-6-nitro-1H-benzo[d]imidazol-2(3H)-one.

$^1$H NMR (400 MHz, Acetone-$d_6$) δ 6.87 (d, J=8.3 Hz, 1H), 6.64 (d, J=2.1 Hz, 1H), 6.55 (dd, J=8.3 Hz, 2.1 Hz, 1H), 4.64 (s, 2H), 3.32 (s, 3H).

Step 16-2: Preparation of 6-amino-3-methylbenzo[d]oxazol-2(3H)-one 111 mg (yield: 88%) of the title compound was obtained in the same manner as in Step 14-2 of Example 14 above, except that 3-methyl-6-nitrobenzo[d]oxazol-2(3H)-one obtained in Step 16-1 was used instead of 3-methyl-6-nitrobenzo[d]thiazol-2(3H)-one.

$^1$H NMR (400 MHz, Acetone-$d_6$) δ 6.95 (d, J=8.5 Hz, 1H), 6.87 (d, J=2.3 Hz, 1H), 6.72 (dd, J=8.5 Hz, 2.3 Hz, 1H), 4.62 (s, 2H), 3.35 (s, 3H).

Step 16-3: Preparation of (3-methyl-2-oxo-2,3-dihydrobenzo[d]oxazol-6-yl)carbonohydrazonoyl dicyanide 107 mg (yield: 73%) of the title compound was obtained in the same manner as in Step 9-4 of Example 9 above, except that 6-amino-3-methylbenzo[d]oxazol-2(3H)-one obtained in Step 16-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.43 (d, J=2.0 Hz, 1H), 7.36 (dd, J=8.5 Hz, 2.0 Hz, 1H), 7.29 (d, J=8.5 Hz, 1H), 3.34 (s, 3H).

EXAMPLE 17: PREPARATION OF (1-METHYL-2-OXO-2,3-DIHYDRO-1H-BENZO[D]IMIDAZOL-5-YL)CARBONOHYDRAZONOYL DICYANIDE (COMPOUND 17)

Step 17-1: Preparation of N-methyl-2,4-dinitroaniline

1-Chloro-2,4-dinitrobenzene (3 g, 14.81 mmol) was dissolved in THF under a nitrogen atmosphere, 2.0 M methylamine (37.03 mL, 74.06 mmol) dissolved in THF was added thereto, and the reaction mixture was stirred at room temperature for 16 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified with ether and filtered to obtain 2.81 g (yield: 96%) of the title compound.

$^1$H NMR (400 MHz, Acetone-$d_6$) δ 8.99 (d, J=2.8 Hz, 1H), 8.82 (s, 1H), 8.35-8.32 (m, 1H), 7.23 (d, J=9.6 Hz, 1H), 3.24 (d, J=5.2 Hz, 3H).

Step 17-2: Preparation of $N^1$-methyl-4-nitrobenzene-1,2-diamine

After N-methyl-2,4-dinitroaniline (300 mg, 1.52 mmol) obtained in Step 17-1 was dissolved in methanol, sodium sulfide (356 mg, 4.57 mmol) and sodium hydrogen carbonate (384 mg, 4.57 mmol) dissolved in distilled water were added thereto, and the reaction mixture was stirred under a nitrogen atmosphere at 80° C. for 8 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified with ether and filtered to obtain 193 mg (yield: 76%) of the title compound.

$^{1}$H NMR (400 MHz, Acetone-$d_6$) δ 7.68 (dd, J=8.8 Hz, 2.8 Hz, 1H), 7.58 (d, J=2.8 Hz, 1H), 6.55 (d, J=8.8 Hz, 1H), 5.42 (s, 1H), 4.54 (s, 2H), 2.96 (s, 3H).

Step 17-3: Preparation of 1-methyl-5-nitro-1,3-dihydro-2H-benzo[d]imidazol-2-one After $N^1$-methyl-4-nitrobenzene-1,2-diamine (900 mg, 5.38 mmol) obtained in Step 17-2 was dissolved in DMF, CDI (2.56 g, 16.15 mmol) was added thereto, and the reaction mixture was stirred under a nitrogen atmosphere at room temperature for 15 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified with ether and filtered to obtain 568 mg (yield: 55%) of the title compound.

$^{1}$H NMR (400 MHz, Acetone-$d_6$) δ 10.27 (s, 1H), 8.10 (dd, J=8.6 Hz, 2.2 Hz, 1H), 7.93 (d, J=2.0 Hz, 1H), 7.29 (d, J=8.8 Hz, 1H), 3.47 (s, 3H).

Step 17-4: Preparation of 5-amino-1-methyl-1,3-dihydro-2H-benzo[d]imidazol-2-one 306 mg (yield: 91%) of the title compound was obtained in the same manner as in Step 1-2 of Example 1 above, except that 1-methyl-5-nitro-1,3-dihydro-2H-benzo[d]imidazol-2-one (400 mg, 2.07 mmol) obtained in Step 17-3 was used instead of 7-nitroisoquinolin-1(2H)-one, and methanol was used as a solvent instead of 1,4-dioxane.

$^{1}$H NMR (400 MHz, Acetone-$d_6$) δ 9.37 (s, 1H), 6.72 (d, J=8.4 Hz, 1H), 6.44 (d, J=2.0 Hz, 1H), 6.39 (dd, J=8.4 Hz, 2.0 Hz, 1H), 4.31 (s, 2H), 3.23 (s, 3H).

Step 17-5: Preparation of (1-methyl-2-oxo-2,3-dihydro-1H-benzo[d]imidazol-5-yl)carbonohydrazonoyl dicyanide 62 mg (yield: 17%) of the title compound was obtained in the same manner as in Step 9-4 of Example 9 above, except that 5-amino-1-methyl-1,3-dihydro-2H-benzo[d]imidazol-2-one (250 mg, 1.53 mmol) obtained in Step 17-4 was used instead of 5-amino-6-fluoro-1,3-dimethyl-1H-benzo[d]imidazol-2(3H)-one, and a mixed solution of ethanol and water in a ratio of 1:3 was used as a solvent.

$^{1}$H NMR (400 MHz, DMSO-$d_6$) δ 13.01 (s, 1H), 10.99 (s, 1H), 7.19 (dd, J=8.4 Hz, 2.0 Hz, 1H), 7.12-7.10 (m, 2H), 3.27 (s, 3H).

EXAMPLE 18: PREPARATION OF (3-ISOPROPYL-2-OXO-2,3-DIHYDROBENZO[D]THIAZOL-6-YL)CARBONOHYDRAZONOYL DICYANIDE (COMPOUND 18)

Step 18-1: Preparation of 3-isopropyl-6-nitrobenzo[d]thiazol-2(3H)-one 162 mg (yield: 44%) of the title compound was obtained in the same manner as in Step 9-2 of Example 9 above, except that 6-nitrobenzo[d]thiazol-2(3H)-one was used instead of 5-fluoro-6-nitro-1H-benzo[d]imidazol-2(3H)-one, and 2-iodopropane was used instead of methyl iodide.

$^{1}$H NMR (400 MHz, Acetone-$d_6$) δ 8.59 (d, J=2.4 Hz), 8.26 (dd, J=9.2 Hz, 2.4 Hz), 7.67 (d, J=9.2 Hz), 4.97-4.90 (m, 1H), 1.61 (d, J=6.8 Hz, 6H).

Step 18-2: Preparation of 6-amino-3-Isopropylbenzo[d]thiazol-2(3H)-one 112 mg (yield: 85%) of the title compound was obtained in the same manner as in Step 14-2 of Example 14 above, except that 3-isopropyl-6-nitrobenzo[d]thiazol-2(3H)-one obtained in Step 18-1 was used instead of 3-methyl-6-nitrobenzo[d]thiazol-2(3H)-one.

$^{1}$H NMR (400 MHz, Acetone-$d_6$) δ 7.13 (d, J=8.8 Hz, 1H), 6.87 (d, J=2.4 Hz, 1H), 6.71 (dd, J=8.8 Hz, 2.4 Hz, 1H), 4.76-4.69 (m, 1H), 4.64 (s, 2H), 1.53 (d, J=6.8 Hz, 6H).

Step 18-3: Preparation of (3-isopropyl-2-oxo-2,3-dihydrobenzo[d]thiazol-6-yl)carbonohydrazonoyl dicyanide 109 mg (yield: 80%) of the title compound was obtained in the same manner as in Step 9-4 of Example 9 above, except that 6-amino-3-isopropylbenzo[d]thiazol-2(3H)-one obtained in Step 18-2 was used instead of 5-amino-6-fluoro-1,3-dimethyl-1H-benzo[d]imidazol-2(3H)-one, and a mixed solution of ethanol and water in a ratio of 1:3 was used as a solvent.

$^{1}$H NMR (400 MHz, DMSO-$d_6$) δ 7.79 (d, J=2.4 Hz, 1H), 7.55 (d, J=9.2 Hz, 1H), 7.49 (d, J=2.4 Hz, 1H), 4.81-4.74 (m, 1H), 1.50 (d, J=7.2 Hz, 6H).

EXAMPLE 19: PREPARATION OF (3-(DIFLUOROMETHYL)-2-OXO-2,3-DIHYDROBENZO[D]THIAZOL-6-YL)CARBONOHYDRAZONOYL DICYANIDE (COMPOUND 19)

Step 19-1: Preparation of 3-(difluoromethyl)-6-nitrobenzo[d]thiazol-2(3H)-one

After 6-nitrobenzo[d]thiazol-2(3H)-one (300 mg, 1.53 mmol) was dissolved in DMF under a nitrogen atmosphere, sodium 2-chloro-2,2-difluoroacetate (467 mg, 3.06 mmol) and DBU (0.46 mL, 3.06 mmol) were added thereto, and the reaction mixture was stirred at room temperature for 16 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified with methanol and filtered to obtain 176 mg (yield: 47%) of the title compound.

$^{1}$H NMR (400 MHz, Acetone-$d_6$) δ 8.76 (d, J=2.4 Hz, 1H), 8.38 (dd, J=9.2 Hz, 2.4 Hz, 1H), 7.79 (d, J=8.8 Hz, 1H), 7.75 (t, J=57.2 Hz, 1H).

Step 19-2: Preparation of 6-amino-3-(difluoromethyl)benzo[d]thiazol-2(3H)-one 125 mg (yield: 95%) of the title compound was obtained in the same manner as in Step 1-2 of Example 1 above, except that 3-(difluoromethyl)-6-nitrobenzo[d]thiazol-2(3H)-one obtained in Step 19-1 was used instead of 7-nitroisoquinolin-1(2H)-one, and methanol was used as a solvent instead of 1,4-dioxane.

$^{1}$H NMR (400 MHz, Acetone-$d_6$) δ 7.55 (t, J=58.0 Hz, 1H), 7.23 (d, J=8.8 Hz, 1H), 6.93 (d, J=2.4 Hz, 1H), 6.76 (dd, J=8.6 Hz, 2.2 Hz, 1H), 4.89 (s, 2H).

Step 19-3: Preparation of (3-(difluoromethyl)-2-oxo-2,3-dihydrobenzo[d]thiazol-6-yl)carbonohydrazonoyl dicyanide 85 mg (yield: 63%) of the title compound was obtained in the same manner as in Step 9-4 of Example 9 above, except that 6-amino-3-(difluoromethyl)benzo[d]thiazol-2(3H)-one obtained in Step 19-2 instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.90 (s, 1H), 7.82 (t, J=56.8 Hz, 1H), 7.53 (s, 2H).

EXAMPLE 20: PREPARATION OF (3-ISOPROPYL-2-OXO-2,3-DIHYDROBENZO[D]OXAZOL-6-YL)CARBONOHYDRAZONOYL DICYANIDE (COMPOUND 20)

Step 20-1: Preparation of 3-isopropyl-6-nitrobenzo[d]oxazol-2(3H)-one 201 mg (yield: 54%) of the title compound was obtained in the same manner as in Step 9-2 of Example 9 above, except that 6-nitrobenzo[d]oxazol-2(3H)-one was used instead of 5-fluoro-6-nitro-1H-benzo[d]imidazol-2(3H)-one, and 2-iodopropane was used instead of methyl iodide.

$^1$H NMR (400 MHz, Acetone-$d_6$) δ 8.23 (dd, J=8.8 Hz, 2.0 Hz, 1H), 8.16 (d, J=2.0 Hz, 1H), 7.61 (d, J=8.8 Hz, 1H), 4.72-4.65 (m, 1H), 1.61 (d, J=6.8 Hz, 6H).

Step 20-2: Preparation of 6-amino-3-isopropylbenzo[d]oxazol-2(3H-one 124 mg (yield: 85%) of the title compound was obtained in the same manner as in Step 1-2 of Example 1 above, except that 3-isopropyl-6-nitrobenzo[d]thiazol-2(3H)-one obtained in Step 20-1 was used instead of 7-nitroisoquinolin-1(2H)-one, and methanol was used as a solvent instead of 1,4-dioxane.

$^1$H NMR (400 MHz, Acetone-$d_6$) δ 7.00 (d, J=8.4 Hz, 1H), 6.61 (d, J=2.0 Hz, 1H), 6.51 (dd, J=8.4 Hz, 2.0 Hz, 1H), 4.62 (s, 2H), 4.48-4.41 (m, 1H), 1.48 (d, J=6.8 Hz, 6H).

Step 20-3: Preparation of (3-isopropyl-2-oxo-2,3-dihydrobenzo[d]oxazol-6-yl)carbonohydrazonoyl dicyanide 99 mg (yield: 59%) of the title compound was obtained in the same manner as in Step 9-4 of Example 9 above, except that 6-amino-3-isopropylbenzo[d]oxazol-2(3H)-one obtained in Step 20-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.47-7.43 (m, 2H), 7.33 (dd, J=8.8 Hz, 2.0 Hz, 1H), 4.51-4.44 (m, 1H), 1.46 (d, J=6.8 Hz, 6H).

EXAMPLE 21: PREPARATION OF (3-(DIFLUOROMETHYL)-2-OXO-2,3-DIHYDROBENZO[D]OXAZOL-6-YL)CARBONOHYDRAZONOYL DICYANIDE (COMPOUND 21)

Step 21-1: Preparation of 3-(difluoromethyl)-6-nitrobenzo[d]oxazol-2(3H)-one 144 mg (yield: 38%) of the title compound was obtained in the same manner as in Step 19-1 of Example 19 above, except that 6-nitrobenzo[d]oxazol-2(3H)-one (300 mg, 1.67 mmol) was used instead of 6-nitrobenzo[d]thiazol-2(3H)-one.

$^1$H NMR (400 MHz, Acetone-$d_6$) δ 8.34-8.30 (m, 2H), 7.68 (d, J=8.8 Hz, 1H), 7.65 (t, J=57.6 Hz, 1H).

Step 21-2: Preparation of 6-amino-3-(difluoromethyl)benzo[d]oxazol-2(3H)-one 110 mg (yield: 98%) of the title compound was obtained in the same manner as in Step 1-2 of Example 1 above, except that 3-(difluoromethyl)-6-nitrobenzo[d]oxazol-2(3H)-one obtained in Step 21-1 was used instead of 7-nitroisoquinolin-1(2H)-one, and methanol was used as a solvent instead of 1,4-dioxane.

$^1$H NMR (400 MHz, Acetone-$d_6$) δ 7.68 (t, J=58.4 Hz, 1H), 7.08 (d, J=8.4 Hz, 1H), 6.70 (d, J=2.4 Hz, 1H), 6.61 (dd, J=8.4 Hz, 2.0 Hz, 1H) 4.91 (s, 2H).

Step 21-3: Preparation of (3-(difluoromethyl)-2-oxo-2,3-dihydrobenzo[d]oxazol-6-yl)carbonohydrazonoyl dicyanide 85 mg (yield: 63%) of the title compound was obtained in the same manner as in Step 9-4 of Example 9 above, except that 6-amino-3-(difluoromethyl)benzo[d]oxazol-2(3H)-one obtained in Step 21-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.73 (t, J=57.2 Hz, 1H), 7.52 (d, J=1.2 Hz, 1H), 7.45-7.40 (m, 2H).

EXAMPLE 22: PREPARATION OF (1,3-DIMETHYL-2-OXO-2,3-DIHYDRO-1H-BENZO[D]IMIDAZOL-5-YL)CARBONOHYDRAZONOYL DICYANIDE (COMPOUND 22)

Step 22-1: Preparation of 1,3-dimethyl-5-nitro-1H-benzo[d]imidazol-2(3H)-one 207 mg (yield: 64%) of the title compound was obtained in the same manner as in Step 9-2 of Example 9 above, except that 5-nitro-1H-benzo[d]imidazol-2(3H)-one was used instead of 5-fluoro-6-nitro-1H-benzo[d]imidazol-2(3H)-one.

$^1$H NMR (400 MHz, Acetone-$d_6$) δ 8.09 (dd, J=8.6 Hz, 2.2 Hz), 7.98 (d, J=2.0 Hz), 7.30 (d, J=8.4 Hz), 3.51 (s, 3H), 3.48 (s, 3H).

Step 22-2: Preparation of 5-amino-1,3-dimethyl-1H-benzo[d]imidazol-2(3H)-one 105 mg (yield: 82%) of the title compound was obtained in the same manner as in Step 1-2 of Example 1 above, except that 1,3-dimethyl-5-nitro-1H-benzo[d]imidazol-2(3H)-one obtained in Step 22-1 was used instead of 7-nitroisoquinolin-1(2H)-one, and methanol was used as a solvent instead of 1,4-dioxane.

$^1$H NMR (400 MHz, Acetone-$d_6$) δ 6.76 (d, J=8.0 Hz, 1H), 6.43-6.40 (m, 2H), 4.38 (s, 2H), 3.27 (s, 3H), 3.26 (s, 3H).

Step 22-3: Preparation of (1,3-dimethyl-2-oxo-2,3-dihydro-1H-benzo[d]imidazol-5-yl)carbonohydrazonoyl dicyanide 11 mg (yield: 8%) of the title compound was obtained in the same manner as in Step 9-4 of Example 9 above, except that 5-amino-1,3-dimethyl-1H-benzo[d]imidazol-2(3H)-one obtained in Step 22-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, Acetone-$d_6$) δ 7.18-7.14 (m, 2H), 6.97 (d, J=8.0 Hz, 1H), 3.37 (s, 3H), 3.35 (s, 3H).

EXAMPLE 23: PREPARATION OF (1,3-DIISOPROPYL-2-OXO-2,3-DIHYDRO-1H-BENZO[D]IMIDAZOL-5-YL)CARBONOHYDRAZONOYL DICYANIDE (COMPOUND 23)

Step 23-1: Preparation of 1,3-diisopropyl-5-nitro-1H-benzo[d]imidazol-2(3H)-one 204 mg (yield: 46%) of the title compound was obtained in the same manner as in Step 9-2 of Example 9 above, except that 5-nitro-1H-benzo[d]imidazol-2(3H)-one was used instead of 5-fluoro-6-nitro-1H-benzo[d]imidazol-2(3H)-one, and 2-iodopropane was used instead of methyl iodide.

$^1$H NMR (400 MHz, Acetone-$d_6$) δ 8.05-8.02 (m, 2H), 7.46 (d, J=8.8 Hz, 1H), 4.80-4.72 (m, 2H), 1.58-1.54 (m, 12H).

Step 23-2: Preparation of 5-amino-1,3-diisopropyl-1H-benzo[d]imidazol-2(3H)-one 118 mg (yield: 89%) of the title compound was obtained in the same manner as in Step 1-2 of Example 1 above, except that 1,3-diisopropyl-5-nitro-1H-benzo[d]imidazol-2(3H)-one obtained in Step 23-1 was used instead of 7-nitroisoquinolin-1(2H)-one, and methanol was used as a solvent instead of 1,4-dioxane.

$^1$H NMR (400 MHz, Acetone-$d_6$) δ 6.92 (d, J=8.0 Hz, 1H), 6.64 (d, J=2.0 Hz, 1H), 6.37 (dd, J=8.4 Hz, 2.4 Hz, 1H), 4.62-4.54 (m, 2H), 4.33 (s, 2H), 1.46-1.43 (m, 12H).

Step 23-3: Preparation of (1,3-diisopropyl-2-oxo-2,3-dihydro-1H-benzo[d]imidazol-5-yl)carbonohydrazonoyl dicyanide 12 mg (yield: 10%) of the title compound was obtained in the same manner as in Step 9-4 of Example 9 above, except that 5-amino-1,3-diisopropyl-1H-benzo[d]imidazol-2(3H)-one obtained in Step 23-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.22-7.20 (m, 2H), 7.04 (dd, J=8.8 Hz, 1.6 Hz, 1H), 4.61-4.55 (m, 2H), 1.44-1.42 (m, 12H).

EXAMPLE 24: PREPARATION OF (1,3-BIS(DIFLUOROMETHYL)-2-OXO-2,3-DIHYDRO-1H-BENZO[D]IMIDAZOL-5-YL)CARBONOHYDRAZONOYL DICYANIDE (COMPOUND 24)

Step 24-1: Preparation of 1,3-bis(difluoromethyl)-5-nitro-1H-benzo[d]imidazol-2(3H)-one 179 mg (yield: 38%) of the title compound was obtained in the same manner as in Step 19-1 of Example 19 above, except that 5-nitro-1H-benzo[d]imidazol-2(3H)-one was used instead of 6-nitrobenzo[d]thiazol-2(3H)-one.

$^1$H NMR (400 MHz, Acetone-$d_6$) δ 8.33 (dd. J=8.8 Hz, 2.0 Hz, 1H), 8.22 (d, J=2.0 Hz, 1H), 7.83-7.53 (m, 2H).

Step 24-2: Preparation of 5-amino-1,3-bis(difluoromethyl)-1H-benzo[d]imidazol-2(3H)-one 69 mg (yield: 96%) of the title compound was obtained in the same manner as in Step 1-2 of Example 1 above, except that 1,3-bis(difluoromethyl)-6-nitro-1H-benzo[d]imidazol-2(3H)-one obtained in Step 24-1 was used instead of 7-nitroisoquinolin-1(2H)-one, and methanol was used as a solvent instead of 1,4-dioxane.

$^1$H NMR (400 MHz, Acetone-$d_6$) δ 7.62-7.32 (m, 2H), 7.13 (d, J=8.8 Hz, 1H), 6.82 (s, 1H), 6.63 (dd, J=8.6 Hz, 2.2 Hz, 1H), 4.90 (s, 2H).

Step 24-3: Preparation of (1,3-bis(difluoromethyl)-2-oxo-2,3-dihydro-1H-benzo[d]imidazol-5-yl)carbonohydrazonoyl dicyanide 45 mg (yield: 58%) of the title compound was obtained in the same manner as in Step 9-4 of Example 9 above, except that 5-amino-1,3-bis(difluoromethyl)-1H-benzo[d]imidazol-2(3H)-one obtained in Step 24-2 was used instead of 5-amino-6-fluoro-1,3-dimethyl-1H-benzo[d]imidazol-2(3H)-one, and a mixed solution of ethanol and water in a ratio of 1:3 was used as a solvent.

$^1$H NMR (400 MHz, DMSO-$d_6$) δ 7.93-7.61 (m, 2H), 7.56 (s, 1H), 7.49-7.42 (m, 2H).

EXAMPLE 25: PREPARATION OF (1-METHYL-2-OXO-1,2-DIHYDROQUINOLIN-6-YL)CARBONOHYDRAZONOYL DICYANIDE (COMPOUND 25)

Step 25-1: Preparation of 1-methyl-6-nitroquinolin-2(1H)-one 123 mg (yield: 38%) of the title compound was obtained in the same manner as in Step 9-2 of Example 9 above, except that 6-nitroquinolin-2(1H)-one was used instead of 5-fluoro-6-nitro-1H-benzo[d]imidazol-2(3H)-one.

$^1$H NMR (400 MHz, DMSO-$d_6$) δ 8.74 (d, J=2.7 Hz, 1H), 8.40 (dd, J=9.4 Hz, 2.7 Hz, 1H), 8.15 (d, J=9.5 Hz, 1H), 7.73 (d, J=9.3 Hz, 1H), 6.80 (d, J=9.5 Hz, 1H), 3.67 (s, 3H).

Step 25-2: Preparation of 6-amino-1-methylquinolin-2(1H)-one 56 mg (yield: 59%) of the title compound was obtained in the same manner as in Step 13-2 of Example 13 above, except that 1-methyl-6-nitroquinolin-2(1H)-one obtained in Step 25-1 was used instead of 6-nitrobenzo[d]thiazol-2(3H)-one, and THF and water were used as solvents.

$^1$H NMR (400 MHz, DMSO-$d_6$) δ 7.66 (d, J=9.4 Hz, 1H), 7.25 (d, J=8.9 Hz, 1H), 6.94 (dd, J=8.9 Hz, 2.7 Hz, 1H), 6.78 (d, J=2.6 Hz, 1H), 6.48 (d, J=9.4 Hz, 1H), 5.09 (s, 2H), 3.53 (s, 3H).

Step 25-3: Preparation of (1-methyl-2-oxo-1,2-dihydroquinolin-6-yl)carbonohydrazonoyl dicyanide 55 mg (yield: 77%) of the title compound was obtained in the same manner as in Step 1-3 of Example 1 above, except that 6-amino-1-methylquinolin-2(1H)-one obtained in Step 25-2 was used instead of 7-aminoisoquinolin-1(2H)-one.

$^1H$ NMR (400 MHz, DMSO-$d_6$) δ 13.16 (s, 1H), 7.98 (d, J=9.5 Hz, 1H), 7.79 (d, J=2.5 Hz, 1H), 7.74 (dd, J=9.1 Hz, 2.6 Hz, 1H), 7.59 (d, J=9.1 Hz, 1H), 6.66 (d, J=9.5 Hz, 1H), 3.61 (s, 3H).

EXAMPLE 26: PREPARATION OF (4-METHYL-2-OXO-1,2-DIHYDROQUINOLIN-6-YL)CARBONOHYDRAZONOYL DICYANIDE (COMPOUND 26)

Step 26-1: Preparation of 4-methyl-6-nitroquinolin-2(1H)-one

After 4-methylquinolin-2(1H)-one (1 g, 6.28 mmol) was dissolved in sulfuric acid (4 mL), a 65% mixed solution of nitric acid (0.5 mL) and sulfuric acid (0.5 mL) was added thereto, and the reaction mixture was stirred at 0° C. for 2 hours. Upon completion of the reaction, distilled water (30 mL) was added thereto, and the reaction mixture was stirred at 0° C. and filtered to obtain 1.08 g (yield: 84%) of the title compound.

$^1H$ NMR (400 MHz, DMSO-$d_6$) δ 12.18 (s, 1H), 8.51 (d, J=2.6 Hz, 1H), 8.35 (dd, J=9.0 Hz, 2.5 Hz, 1H), 7.44 (d, J=9.0 Hz, 1H), 6.58 (s, 1H).

Step 26-2: Preparation of 6-amino-4-methylquinolin-2(1H)-one 47 mg (yield: 37%) of the title compound was obtained in the same manner as in Step 13-2 of Example 13 above, except that 4-methyl-6-nitroquinolin-2(1H)-one obtained in Step 26-1 was used instead of 6-nitrobenzo[d]thiazol-2(3H)-one, and THE and water were used as solvents.

$^1H$ NMR (400 MHz, DMSO-$d_6$) δ 11.22 (s, 1H), 7.04 (d, J=8.5 Hz, 1H), 6.87-6.78 (m, 2H), 6.28 (s, 1H), 5.00 (s, 2H), 2.31 (s, 3H).

Step 26-3: Preparation of (4-methyl-2-oxo-1,2-dihydroquinolin-6-yl)carbonohydrazonoyl dicyanide 48 mg (yield: 83%) of the title compound was obtained in the same manner as in Step 1-3 of Example 1 above, except that 6-amino-4-methylquinolin-2(1H)-one obtained in Step 26-2 was used instead of 7-aminoisoquinolin-1(2H)-one.

$^1H$ NMR (400 MHz, DMSO-$d_6$) δ 13.13 (s, 1H), 11.73 (s, 1H), 7.78 (d, J=2.4 Hz, 1H), 7.66 (dd, J=8.9 Hz, 2.4 Hz, 1H), 7.34 (d, J=8.9 Hz, 1H), 6.47 (s, 1H), 2.41 (s, 3H).

EXAMPLE 27: PREPARATION OF (1,4-DIMETHYL-2-OXO-1,2-DIHYDROQUINOLIN-6-YL) CARBONOHYDRAZONOYL DICYANIDE (COMPOUND 27)

Step 27-1: Preparation of 1,4-dimethyl-6-nitroquinolin-2(1H)-one 206 mg (yield: 38%) of the title compound was obtained in the same manner as in Step 9-2 of Example 9 above, except that 4-methyl-6-nitroquinolin-2(1H)-one was used instead of 5-fluoro-6-nitro-1H-benzo[d]imidazol-2(3H)-one.

$^1H$ NMR (400 MHz, DMSO-$d_6$) δ 8.55 (d, J=2.6 Hz, 1H), 8.42 (ddd, J=9.3 Hz, 2.6 Hz, 1.1 Hz, 1H), 7.73 (dd, J=9.4 Hz, 1.1 Hz, 1H), 6.72 (s, 1H), 3.65 (s, 3H), 2.53 (s, 3H).

Step 27-2: Preparation of 6-amino-1,4-dimethylquinolin-2(1M-one 33 mg (yield: 19%) of the title compound was obtained in the same manner as in Step 13-2 of Example 13 above, except that 1,4-dimethyl-6-nitroquinolin-2(1H)-one obtained in Step 27-1 was used instead of 6-nitrobenzo[d]thiazol-2(3H)-one, and THE and water were used as solvents.

$^1H$ NMR (400 MHz, DMSO-$d_6$) δ 7.25 (d, J=8.9 Hz, 1H), 6.94 (dd, J=8.9 Hz, 2.5 Hz, 1H), 6.89 (d, J=2.5 Hz, 1H), 6.42 (s, 1H), 5.10 (s, 2H), 3.52 (s, 3H), 2.32 (s, 3H).

Step 27-3: Preparation of (1,4-dimethyl-2-oxo-1,2-dihydroquinolin-6-yl)carbonohydrazonoyl dicyanide 55 mg (yield: 77%) of the title compound was obtained in the same manner as in Step 1-3 of Example 1 above, except that 6-amino-1,4-dimethylquinolin-2(1H)-one obtained in Step 27-2 was used instead of 7-aminoisoquinolin-1(2H)-one.

$^1H$ NMR (400 MHz, DMSO-$d_6$) δ 13.14 (s, 1H), 7.82 (d, J=2.5 Hz, 1H), 7.73 (dd, J=9.2 Hz, 2.5 Hz, 1H), 7.58 (d, J=9.2 Hz, 1H), 6.59 (s, 1H), 3.59 (s, 3H), 2.42 (s, 3H).

EXAMPLE 28: PREPARATION OF (3-METHYL-2-OXO-2,3-DIHYDROBENZO[D]OXAZOL-5-YL) CARBONOHYDRAZONOYL DICYANIDE (COMPOUND 28)

Step 28-1: Preparation of 3-methyl-5-nitrobenzo[d]oxazol-2(3H)-one 226 mg (yield: 70%) of the title compound was obtained in the same manner as in Step 9-2 of Example 9 above, except that 5-nitrobenzo[d]dioxol-2(3H)-one was used instead of 5-fluoro-6-nitro-1H-benzo[d]imidazol-2(3H)-one.

$^1H$ NMR (400 MHz, DMSO-$d_6$) δ 8.21 (d, J=2.3 Hz, 1H), 8.10 (dd, J=8.8 Hz, 2.4 Hz, 1H), 7.58 (d, J=8.8 Hz, 1H), 3.43 (s, 3H).

Step 28-2: Preparation of 5-amino-3-methylbenzo[d]oxazol-2(3H)-one 150 mg (yield: 88%) of the title compound was obtained in the same manner as in Step 1-2 of Example 1 above, except that 3-methyl-5-nitrobenzo[d]oxazol-2(3H)-one obtained in Step 28-1 was used instead of 7-nitroisoquinolin-1(2H)-one.

$^1H$ NMR (400 MHz, DMSO-$d_6$) δ 6.95 (d, J=8.5 Hz, 1H), 6.37 (d, J=2.2 Hz, 1H), 6.28 (dd, J=8.5 Hz, 2.2 Hz, 1H), 5.07 (s, 2H), 3.23 (s, 3H).

Step 28-3: Preparation of (3-methyl-2-oxo-2,3-dihydrobenzo[d]oxazol-5-yl)carbonohydrazonoyl dicyanide 73 mg (yield: 38%) of the title compound was obtained in the same manner as in Step 1-3 of Example 1 above, except that 5-amino-3-methylbenzo[d]oxazol-2(3H)-one obtained in Step 28-2 was used instead of 7-aminoisoquinolin-1(2H)-one.

$^1H$ NMR (400 MHz, DMSO-$d_6$) δ 13.11 (s, 1H), 7.36 (d, J=8.6 Hz, 1H), 7.32 (d, J=2.1 Hz, 1H), 7.24 (dd, J=8.6 Hz, 2.2 Hz, 1H).

EXAMPLE 29: PREPARATION OF (3-ISOPROPYL-2-OXO-2,3-DIHYDROBENZO[D]OXAZOL-5-YL)CARBONOHYDRAZONOYL DICYANIDE (COMPOUND 29)

Step 29-1: Preparation of 3-isopropyl-6-nitrobenzo[d]oxazol-2(3H)-one 94 mg (yield: 25%) of the title compound was obtained in the same manner as in Step 28-1 of Example 28 above, except that 2-iodopropane was used instead of methyl iodide.

$^1$H NMR (400 MHz, DMSO-$d_6$) δ 8.22 (d, J=2.3 Hz, 1H), 8.10 (dd, J=8.8 Hz, 2.3 Hz, 1H), 7.59 (d, J=8.8 Hz, 1H), 4.62 (hept, J=6.9 Hz, 1H), 1.48 (d, J=6.9 Hz, 6H).

Step 29-2: Preparation of 5-amino-3-isopropylbenzo[d]oxazol-2(3H)-one 48 mg (yield: 61%) of the title compound was obtained in the same manner as in Step 1-2 of Example 1 above, except that 3-isopropyl-5-nitrobenzo[d]oxazol-2(3H)-one obtained in Step 29-1 was used instead of 7-nitroisoquinolin-1(2H)-one.

$^1$H NMR (400 MHz, DMSO-$d_6$) δ 6.96 (d, J=8.4 Hz, 1H), 6.57 (d, J=2.2 Hz, 1H), 6.28 (dd, J=8.4 Hz, 2.2 Hz, 1H), 5.01 (s, 2H), 4.37 (hept, J=6.9 Hz, 1H), 1.42 (d, J=7.1 Hz, 6H).

Step 29-3: Preparation of (3-isopropyl-2-oxo-2,3-dihydrobenzo[d]oxazol-5-yl)carbonohydrazonoyl dicyanide 9 mg (yield: 15%) of the title compound was obtained in the same manner as in Step 1-3 of Example 1 above, except that 5-amino-3-isopropylbenzo[d]oxazol-2(3H)-one obtained in Step 29-2 was used instead of 7-aminoisoquinolin-1(2H)-one.

$^1$H NMR (400 MHz, DMSO-$d_6$) δ 13.00 (s, 1H), 7.46 (d, J=2.1 Hz, 1H), 7.38 (d, J=8.7 Hz, 1H), 7.24 (dd, J=8.7 Hz, 2.2 Hz, 1H), 4.51 (hept, J=6.9 Hz, 1H), 1.46 (d, J=6.9 Hz, 6H).

EXAMPLE 30: PREPARATION OF (3-(DIFLUOROMETHYL)-2-OXO-2,3-DIHYDROBENZO[D]OXAZOL-5-YL)CARBONOHYDRAZONOYL DICYANIDE (COMPOUND 30)

Step 30-1: Preparation of 3-(difluoromethyl)-5-nitrobenzo[d]oxazol-2(3H)-one 104 mg (yield: 27%) of the title compound was obtained in the same manner as in Step 28-1 of Example 28 above, except that sodium 2-chloro-2,2-difluoroacetate was used instead of methyl iodide.

$^1$H NMR (400 MHz, DMSO-$d_6$) δ 9.05 (s, 1H), 8.71 (s, 1H), 8.38 (dd, J=9.0 Hz, 2.3 Hz, 1H), 8.06 (d, J=9.0 Hz, 1H).

Step 30-2: Preparation of 5-amino-3-(difluoromethyl)benzo[d]oxazol-2(3H)-one

The title compound was obtained in the same manner as in Step 1-2 of Example 1 above, except that 3-(difluoromethyl)-5-nitrobenzo[d]oxazol-2(3H)-one obtained in Step 30-1 was used instead of 7-nitroisoquinolin-1(2H)-one and used in the next step without additional purification.

Step 30-3: Preparation of (3-(difluoromethyl)-2-oxo-2,3-dihydrobenzo[d]oxazol-5-yl)carbonohydrazonoyl dicyanide 30 mg (yield: 22%) of the title compound was obtained in the same manner as in Step 1-3 of Example 1 above, except that 5-amino-3-(difluoromethyl)benzo[d]oxazol-2(3H)-one obtained in Step 30-2 was used instead of 7-aminoisoquinolin-1(2H)-one.

$^1$H NMR (400 MHz, DMSO-$d_6$) δ 13.13 (s, 1H), 8.80 (s, 1H), 7.85-7.81 (m, 2H), 7.59 (dd, J=9.0 Hz, 2.1 Hz, 1H).

EXAMPLE 31: PREPARATION OF (1,3,6-TRIMETHYL-2-OXO-2,3-DIHYDRO-1H-BENZO[D]IMIDAZOL-5-YL)CARBONOHYDRAZONOYL DICYANIDE (COMPOUND 31)

Step 31-1: Preparation of 5-methyl-6-nitro-1H-benzo[d]imidazol-2(3H)-one 67 mg (yield: 29%) of the title compound was obtained in the same manner as in Step 9-1 of Example 9 above, except that 4-methyl-5-nitrobenzene-1,2-diamine was used instead of 4-fluoro-5-nitrobenzene-1,2-diamine.

$^1$H NMR (400 MHz, DMSO-$d_6$) δ 11.25 (s, 1H), 11.00 (s, 1H), 7.59 (s, 1H), 6.96 (s, 1H), 2.55 (s, 3H).

Step 31-2: Preparation of 1,3,5-trimethyl-6-nitro-1H-benzo[d]imidazol-2(3H)-one 268 mg (yield: 78%) of the title compound was obtained in the same manner as in Step 9-2 of Example 9 above, except that 5-methyl-6-nitro-1H-benzo[d]imidazol-2(3H)-one obtained in Step 31-1 was used instead of 5-fluoro-6-nitro-1H-benzo[d]imidazol-2(3H)-one $^1$H NMR (400 MHz, DMSO-$d_6$) δ 7.91 (s, 1H), 7.26 (s, 1H), 3.37 (d, J=5.5 Hz, 6H), 2.60 (s, 3H).

Step 31-3: Preparation of 5-amino-1,3,6-trimethyl-1H-benzo[d]imidazol-2(3H)-one 169 mg (yield: 78%) of the title compound was obtained in the same manner as in Step 1-2 of Example 1 above, except that 1,3,5-trimethyl-6-nitro-1H-benzo[d]imidazol-2(3H)-one obtained in Step 31-2 was used instead of 7-nitroisoquinolin-1(2H)-one.

$^1$H NMR (400 MHz, DMSO-$d_6$) δ 6.73 (s, 1H), 6.41 (s, 1H), 4.55 (s, 2H), 3.20 (d, J=5.0 Hz, 6H), 2.09 (s, 3H).

Step 31-4: Preparation of (1,3,6-trimethyl-2-oxo-2,3-dihydro-1H-benzo[d]imidazol-5-yl)carbonohydrazonoyl dicyanide 20 mg (yield: 10%) of the title compound was obtained in the same manner as in Step 1-3 of Example 1 above, except that 5-amino-1,3,6-trimethyl-6-nitro-1H-benzo[d]imidazol-one obtained in Step 31-3 was used instead of 7-aminoisoquinolin-1(2H)-one.

$^1$H NMR (400 MHz, DMSO-$d_6$) δ 12.26 (s, 1H), 7.14 (s, 1H), 7.05 (s, 1H), 3.31 (d, J=2.7 Hz, 6H), 2.38 (s, 3H).

EXAMPLE 32: PREPARATION OF (6-METHOXY-1,3-DIMETHYL-2-OXO-2,3-DIHYDRO-1H-BENZO[D]IMIDAZOL-5-YL)CARBONOHYDRAZONOYL DICYANIDE (COMPOUND 32)

Step 32-1: Preparation of 5-methoxy-6-nitro-1H-benzo[d]imidazol-2(3H)-one 336 mg (yield: 98%) of the title compound was obtained in the same manner as in Step 9-1 of Example 9 above, except that 4-methoxy-5-nitrobenzene-1,2-diamine was used instead of 4-fluoro-5-nitrobenzene-1,2-diamine.

$^1$H NMR (400 MHz, DMSO-$d_6$) δ 11.26 (s, 1H), 10.86 (s, 1H), 7.48 (s, 1H), 6.81 (s, 1H), 3.90 (s, 3H).

Step 32-2: Preparation of 5-methoxy-1,3-dimethyl-6-nitro-1H-benzo[d]imidazol-2(3H)-one 224 mg (yield: 66%) of the title compound was obtained in the same manner as in Step 9-2 of Example 9 above, except that 5-methoxy-6-nitro-1H-benzo[d]imidazol-2(3H)-one obtained in Step 32-1 was used instead of 5-fluoro-6-nitro-1H-benzo[d]imidazol-2(3H)-one.

$^1$H NMR (400 MHz, DMSO-$d_6$) δ 7.81 (s, 1H), 7.19 (s, 1H), 3.95 (s, 3H), 3.39 (s, 3H), 3.34 (s, 3H).

Step 32-3: Preparation of 5-amino-6-methoxy-1,3-dimethyl-1H-benzo[d]imidazol-2(3H)-one 78 mg (yield: 44%) of the title compound was obtained in the same manner as in Step 1-2 of Example 1 above, except that 5-methoxy-1,3-dimethyl-6-nitro-1H-benzo[d]imidazol-2(3H)-one obtained in Step 32-2 was used instead of 7-nitroisoquinolin-1(2H)-one.

$^1$H NMR (400 MHz, DMSO-$d_6$) δ 6.78 (s, 1H), 6.47 (s, 1H), 4.45 (s, 2H), 3.78 (s, 3H), 3.25 (s, 3H), 3.20 (s, 3H).

Step 32-4: Preparation of (6-methoxy-1,3-dimethyl-2-oxo-2,3-dihydro-1H-benzo[d]imidazol-5-yl)carbonohydrazonoyl dicyanide 37 mg (yield: 54%) of the title compound was obtained in the same manner as in Step 1-3 of Example 1 above, except that 5-amino-6-methoxy-1,3-dimethyl-6-nitro-1H-benzo[d]imidazol-one obtained in Step 32-3 was used instead of 7-aminoisoquinolin-1(2H)-one.

$^1$H NMR (400 MHz, DMSO-$d_6$) δ 11.75 (s, 1H), 7.21 (s, 1H), 7.12 (s, 1H), 3.94 (s, 3H), 3.34 (s, 3H), 3.31 (s, 3H).

EXAMPLE 33: PREPARATION OF (7-METHOXY-1,3-DIMETHYL-2-OXO-2,3-DIHYDRO-1H-BENZO[D]IMIDAZOL-5-YL)CARBONOHYDRAZONOYL DICYANIDE (COMPOUND 33)

Step 33-1: Preparation of 4-methoxy-6-nitro-1H-benzo[d]imidazol-2(3H)-one 509 mg (yield: 89%) of the title compound was obtained in the same manner as in Step 9-1 of Example 9 above, except that 3-methoxy-5-nitrobenzene-1,2-diamine was used instead of 4-fluoro-5-nitrobenzene-1,2-diamine.

$^1$H NMR (400 MHz, DMSO-$d_6$) δ 11.57 (s, 1H), 11.15 (s, 1H), 7.57 (d, J=2.0 Hz, 1H), 7.48 (d, J=2.0 Hz, 1H), 3.96 (s, 3H).

Step 33-2: Preparation of 4-methoxy-1,3-dimethyl-6-nitro-1H-benzo[d]imidazol-2(3H)-one 119 mg (yield: 70%) of the title compound was obtained in the same manner as in Step 9-2 of Example 9 above, except that 4-methoxy-6-nitro-1H-benzo[d]imidazol-2(3H)-one obtained in Step 33-1 was used instead of 5-fluoro-6-nitro-1H-benzo[d]imidazol-2(3H)-one.

$^1$H NMR (400 MHz, DMSO-$d_6$) δ 7.83 (d, J=2.0 Hz, 1H), 7.64 (d, J=2.0 Hz, 1H), 3.98 (s, 3H), 3.55 (s, 3H), 3.40 (s, 3H).

Step 33-3: Preparation of 6-amino-4-methoxy-1,3-dimethyl-1H-benzo[d]imidazol-2(3H)-one 15 mg (yield: 16%) of the title compound was obtained in the same manner as in Step 1-2 of Example 1 above, except that 4-methoxy-1,3-dimethyl-6-nitro-1H-benzo[d]imidazol-2(3H)-one obtained in Step 33-2 was used instead of 7-nitroisoquinolin-1(2H)-one.

$^1$H NMR (400 MHz, DMSO-$d_6$) δ 6.04 (d, J=1.7 Hz, 1H), 5.97 (d, J=1.7 Hz, 1H), 4.85 (s, 2H), 3.76 (s, 3H), 3.38 (s, 3H), 3.17 (s, 2H).

Step 33-4: Preparation of (7-methoxy-1,3-dimethyl-2-oxo-2,3-dihydro-1H-benzo[d]imidazol-5-yl)carbonohydrazonoyl dicyanide 20 mg (yield: 30%) of the title compound was obtained in the same manner as in Step 1-3 of Example 1 above, except that 6-amino-4-methoxy-1,3-dimethyl-1H-benzo[d]imidazol-one obtained in Step 33-3 was used instead of 7-aminoisoquinolin-1(2H)-one.

$^1$H NMR (400 MHz, DMSO-$d_6$) δ 13.00 (s, 1H), 6.96 (d, J=1.8 Hz, 1H), 6.91 (d, J=1.8 Hz, 1H), 3.87 (s, 3H), 3.48 (s, 3H), 3.30 (s, 3H).

EXAMPLE 34: PREPARATION OF (1,3-DIISOPROPYL-2-OXO-2,3-DIHYDRO-1H-IMIDAZO[4,5-B]PYRIDIN-6-YL)CARBONOHYDRAZONOYL DICYANIDE (COMPOUND 34)

Step 34-1: Preparation of 1,3-diisopropyl-6-nitro-1H-Imidazo[4,5-b]pyridin-2(3H)-one 387 mg (yield: 30%) of the title compound was obtained in the same manner as in Step 9-2 of Example 9 above, except that 6-nitro-1H-imidazo[4,5-b]pyridin-2(3H)-one was used instead of 5-fluoro-6-nitro-1H-benzo[d]imidazol-2(3H)-one, and 2-iodopropane was used instead of methyl iodide.

$^1$H NMR (400 MHz, DMSO-$d_6$) δ 8.94 (d, J=2.3 Hz, 1H), 8.32 (d, J=2.3 Hz, 1H), 4.72 (dhept, J=16.6 Hz, 6.9 Hz, 2H), 1.50 (dd, J=16.1 Hz, 6.9 Hz, 12H).

Step 34-2: Preparation of 6-amino-1,3-diisopropyl-1H-imidazo[4,5-b]pyridin-2(3H)-one 162 mg (yield: 42%) of the title compound was obtained in the same manner as in Step 28-2 of Example 28 above, except that 1,3-diisopropyl-6-nitro-1H-imidazo[4,5-b]pyridin-2(3H)-one obtained in Step 34-1 was used instead of 1-methyl-6-nitroquinolin-2(1H)-one.

$^1$H NMR (400 MHz, DMSO-$d_6$) δ 7.37 (d, J=2.2 Hz, 1H), 6.92 (d, J=2.2 Hz, 1H), 4.84 (s, 2H), 4.61-4.48 (m, J=7.0 Hz, 2H), 1.41 (dd. J=19.6 Hz, 6.9 Hz, 12H).

Step 34-3: Preparation of 6-amino-1,3-diisopropyl-1H-imidazo[4,5-b]pyridin-2(3H)-one 43 mg (yield: 27%) of the title compound was obtained in the same manner as in Step 1-3 of Example 1 above, except that 6-amino-1,3-diisopropyl-1H-imidazo[4,5-b]pyridin-2 (3H)-one obtained in Step 34-2 was used instead of 7-aminoisoquinolin-1(2H)-one.

$^1$H NMR (400 MHz, DMSO-$d_6$) δ 8.13 (d, J=2.2 Hz, 1H), 7.64 (d, J=2.2 Hz, 1H), 4.64 (dp, J=11.5 Hz, 6.9 Hz, 2H), 1.46 (dd, J=19.8 Hz, 6.9 Hz, 12H).

EXAMPLE 35: PREPARATION OF (3-ETHYL-1-METHYL-2-OXO-2,3-DIHYDRO-1H-BENZO[D]IMIDAZOL-5-YL)CARBONOHYDRAZONOYL DICYANIDE (COMPOUND 35)

Step 35-1: Preparation of 3-ethyl-1-methyl-5-nitro-1H-benzo[d]imidazol-2(3H)-one 1-Methyl-5-nitro-1H-benzo[d]imidazol-2(3H)-one (150 mg, 0.78 mmol) was dissolved in DMF (3 mL) and potassium carbonate (214.7 mg, 1.55 mmol) was added thereto, and then the reaction mixture was cooled to 0° C. Ethyl iodide (0.156 mL, 1.94 mmol) was slowly added thereto, and the reaction mixture was slowly heated to room temperature and stirred at room temperature for 17 hours. Upon completion of the reaction, a reaction product was extracted using distilled water and ethyl acetate to obtain an organic layer, and the organic layer was dried over anhydrous magnesium sulfate and filtered. The filtrate was concentrated under reduced pressure, and the crude material was solidified with ether and filtered to obtain 133.5 mg (yield: 77%) of the title compound.

$^{1}$H NMR (400 MHz, Chloroform-d) δ 8.11 (dd, J=8.7 Hz, 2.2 Hz, 1H), 7.90 (d, J=2.1 Hz, 1H), 7.02 (d, J=8.7 Hz, 1H), 3.49 (s, 3H).

Step 35-2: Preparation of 5-amino-3-ethyl-1-methyl-1H-benzo[d]imidazol-2(3H)-one 74.7 mg (yield: 68%) of the title compound was obtained in the same manner as in Step 1-2 of Example 1 above, except that 3-ethyl-1-methyl-5-nitro-1H-benzo[d]imidazol-2(3H)-one obtained in Step 35-1 was used instead of 7-nitroisoquinolin-1(2H)-one.

$^{1}$H NMR (400 MHz, DMSO-$d_6$) δ 6.79 (d, J=8.3 Hz, 1H), 6.40 (d, J=2.1 Hz, 1H), 6.31 (dd, J=8.2 Hz, 2.1 Hz, 1H), 4.76 (s, 2H), 3.74 (q, J=7.2 Hz, 2H), 3.21 (s, 3H), 1.16 (t, J=7.2 Hz, 3H).

Step 35-3: Preparation of (3-ethyl-1-methyl-2-oxo-2,3-dihydro-1H-benzo[d]imidazol-5-yl)carbonohydrazonoyl dicyanide 60.9 mg (yield: 58%) of the title compound was obtained in the same manner as in Step 1-3 of Example 1 above, except that 5-amino-3-ethyl-1-methyl-1H-benzo[d]imidazol-2(3H)-one obtained in Step 35-2 was used instead of 7-aminoisoquinolin-1(2H)-one.

$^{1}$H NMR (400 MHz, DMSO-$d_6$) δ 13.04 (s, 1H), 7.30 (d, J=2.0 Hz, 1H), 7.23 (dd, J=8.4 Hz, 2.0 Hz, 1H), 7.18 (d, J=8.4 Hz, 1H), 3.88 (q, J=7.2 Hz, 2H), 3.32 (s, 3H), 1.20 (t, J=7.2 Hz, 3H).

EXAMPLE 36: PREPARATION OF (3-ISOPROPYL-1-METHYL-2-OXO-2,3-DIHYDRO-1H-BENZO[D]IMIDAZOL-5-YL)CARBONOHYDRAZONOYL DICYANIDE (COMPOUND 36)

Step 36-1: Preparation of 3-isopropyl-1-methyl-5-nitro-1H-benzo[d]imidazol-2(3H)-one 135.9 mg (yield: 55%) of the title compound was obtained in the same manner as in Step 9-2 of Example 9 above, except that 1-methyl-5-nitro-1H-benzo[d]imidazol-2(3H)-one was used instead of 5-fluoro-6-nitro-1H-benzo[d]imidazol-2(3H)-one, and isopropyl iodide was used instead of methyl iodide.

$^{1}$H NMR (400 MHz, Chloroform-d) δ 8.10 (dd, J=8.7 Hz, 2.1 Hz, 1H), 8.01 (d, J=2.2 Hz, 1H), 7.01 (d, J=8.7 Hz, 1H), 4.75 (hept, J=7.0 Hz, 1H), 3.47 (s, 3H), 1.58 (d, J=7.1 Hz, 7H).

Step 36-2: Preparation of 5-amino-3-isopropyl-1-methyl-1H-benzo[d]imidazol-2(3H)-one 114.2 mg (yield: 100%) of the title compound was obtained in the same manner as in Step 1-2 of Example 1 above, except that 3-isopropyl-1-methyl-5-nitro-1H-benzo[d]imidazol-2(3H)-one obtained in Step 36-1 was used instead of 7-nitroisoquinolin-1(2H)-one.

$^{1}$H NMR (400 MHz, DMSO-$d_6$) δ 6.78 (d, J=8.2 Hz, 1H), 6.56 (d, J=2.0 Hz, 1H), 6.30 (dd, J=8.3 Hz, 2.0 Hz, 1H), 4.73 (s, 2H), 4.49 (hept, J=7.0 Hz, 1H), 3.19 (s, 3H), 1.39 (d, J=7.0 Hz, 6H).

Step 36-3: Preparation of (3-Isopropyl-1-methyl-2-oxo-2,3-dihydro-1H-benzo[d]imidazol-5-yl)carbonohydrazonoyl dicyanide 15.2 mg (yield: 9%) of the title compound was obtained in the same manner as in Step 1-3 of Example 1 above, except that 5-amino-3-isopropyl-1-methyl-1H-benzo[d]imidazol-2(3H)-one obtained in Step 36-2 was used instead of 7-aminoisoquinolin-1(2H)-one.

$^{1}$H NMR (400 MHz, DMSO-$d_6$) δ 12.96 (s, 1H), 7.42 (d, J=1.9 Hz, 1H), 7.22 (dd, J=8.5 Hz, 1.9 Hz, 1H), 7.17 (d, J=8.5 Hz, 1H), 4.61 (hept, J=7.0 Hz, 1H), 3.30 (s, 3H), 1.44 (d, J=6.9 Hz, 6H).

EXAMPLE 37: PREPARATION OF (3-(DIFLUOROMETHYL)-1-METHYL-2-OXO-2,3-DIHYDRO-1H-BENZO[D]IMIDAZOL-5-YL)CARBONOHYDRAZONOYL DICYANIDE (COMPOUND 37)

Step 37-1: Preparation of 3-difluoromethyl-1-methyl-5-nitro-1H-benzo[d]imidazol-2(3H)-one After 1-methyl-5-nitro-1H-benzo[d]imidazol-2(3H)-one (100 mg, 0.52 mmol) was dissolved in DMF under a nitrogen atmosphere, sodium 2-chloro-2,2-difluoroacetate (157.9 mg, 1.04 mmol) and potassium carbonate (143.1 mg, 1.04 mmol) were added thereto, and the reaction mixture was heated to 80° C. and stirred for 5 hours. Upon completion of the reaction, water was added thereto and an obtained precipitate was filtered and purified by column chromatography to obtain 58.5 mg (yield: 46%) of the title compound.

$^{1}$H NMR (400 MHz, DMSO-$d_6$) δ 8.23 (dd, J=8.8 Hz, 2.2 Hz, 1H), 8.05 (d, J=2.2 Hz, 1H), 7.81 (t, J=57.5 Hz, 1H), 7.52 (d, J=8.8 Hz, 1H), 3.41 (s, 3H).

Step 37-2: Preparation of 5-amino-3-difluoromethyl-1-methyl-1H-benzo[d]imidazol-2(3H)-one 56.1 mg (yield: 72%) of the title compound was obtained in the same manner as in Step 1-2 of Example 1 above, except that 3-difluoromethyl-1-methyl-5-nitro-1H-benzo[d]imidazol-2(3H)-one obtained in Step 37-1 was used instead of 7-nitroisoquinolin-1(2H)-one.

$^{1}$H NMR (400 MHz, DMSO-dB) δ 7.56 (t, J=58.3 Hz, 1H), 6.92 (d, J=8.4 Hz, 1H), 6.65 (d, J=2.0 Hz, 1H), 6.45 (dd, J=8.4 Hz, 2.1 Hz, 1H), 5.03 (s, 2H), 3.24 (s, 3H).

Step 37-3: Preparation of (3-difluoromethyl-1-methyl-2-oxo-2,3-dihydro-1H-benzo[d]imidazol-5-yl)carbonohydrazonoyl dicyanide 53.2 mg (yield: 71%) of the title compound was obtained in the same manner as in Step 1-3 of Example 1 above, except that 5-amino-3-difluoromethyl-1-methyl-1H-benzo[d]imidazol-2(3H)-one obtained in Step 37-2 was used instead of 7-aminoisoquinolin-1(2H)-one.

$^1$H NMR (400 MHz, Acetone-$d_6$) δ 11.86 (s, 1H), 7.56 (d, J=2.1 Hz, 1H), 7.52 (t, J=58.4 Hz, 1H), 7.45 (dd, J=8.6 Hz, 2.1 Hz, 1H), 7.30 (d, J=8.6 Hz, 1H), 3.42 (s, 3H).

EXAMPLE 38: PREPARATION OF (1-ETHYL-3-METHYL-2-OXO-2,3-DIHYDRO-1H-BENZO[D]IMIDAZOL-5-YL)CARBONOHYDRAZONOYL DICYANIDE (COMPOUND 38)

Step 38-1: Preparation of N-ethyl-2,4-dinitroaniline 1.95 g (yield: 93%) of the title compound was obtained in the same manner as in Step 17-1 of Example 17 above, except that ethylamine was used instead of methylamine.

$^1$H NMR (400 MHz, Chloroform-d) δ 9.13 (d, J=2.7 Hz, 1H), 8.49 (s, 1H), 8.27 (ddd, J=9.5 Hz, 2.7 Hz, 0.8 Hz, 1H), 6.92 (d, J=9.5 Hz, 1H), 3.48 (qd, J=7.2 Hz, 5.2 Hz, 2H), 1.43 (t, J=7.2 Hz, 3H).

Step 38-2: Preparation of N-ethyl-4-nitrobenzene-1,2-diamine 1.46 g (yield: 88%) of the title compound was obtained in the same manner as in Step 17-2 of Example 17 above, except that N-ethyl-2,4-dinitroaniline obtained in Step 38-1 was used instead of N-methyl-2,4-dinitroaniline.

$^1$H NMR (400 MHz, Chloroform-d) δ 7.83 (dd, J=8.9 Hz, 2.5 Hz, 1H), 7.62 (d, J=2.5 Hz, 1H), 6.54 (d, J=8.9 Hz, 1H), 4.18 (s, 1H), 3.35 (s, 2H), 3.31-3.17 (m, 2H), 1.34 (t, J=7.2 Hz, 3H).

Step 38-3: Preparation of 1-ethyl-6-nitro-1H-benzo[d]imidazol-2(3H)-one 1.57 g (yield: 95%) of the title compound was obtained in the same manner as in Step 9-1 of Example 9 above, except that N-ethyl-4-nitrobenzene-1,2-diamine obtained in Step 38-2 was used instead of 4-fluoro-5-nitrobenzene-1,2-diamine.

$^1$H NMR (400 MHz, DMSO-$d_6$) δ 11.42 (s, 1H), 8.01 (dd, J=8.7 Hz, 2.3 Hz, 1H), 7.75 (d, J=2.3 Hz, 1H), 7.36 (d, J=8.7 Hz, 1H), 3.90 (q, J=7.2 Hz, 2H), 1.21 (t, J=7.2 Hz, 3H).

Step 38-4: Preparation of 1-ethyl-3-methyl-5-nitro-1H-benzo[d]imidazol-2(3H)-one 172.0 mg (yield: 80%) of the title compound was obtained in the same manner as in Step 9-1 of Example 9 above, except that 1-ethyl-5-nitro-1H-benzo[d]imidazol-2(3H)-one obtained in Step 38-3 was used instead of 1-methyl-5-nitro-1H-benzo[d]imidazol-2(3H)-one, and methyl iodide was used instead of ethyl iodide.

$^1$H NMR (400 MHz, Chloroform-d) δ 8.11 (dd, J=8.7 Hz, 2.2 Hz, 1H), 7.89 (d, J=2.1 Hz, 1H), 7.04 (d, J=8.7 Hz, 1H), 4.00 (q, J=7.3 Hz, 2H), 3.49 (s, 3H), 1.37 (t, J=7.2 Hz, 3H).

Step 38-5: Preparation of 5-amino-1-ethyl-3-methyl-H-benzo[d]imidazol-2(3H)-one 117.6 mg (yield: 80%) of the title compound was obtained in the same manner as in Step 1-2 of Example 1 above, except that 1-ethyl-3-methyl-5-nitro-1H-benzo[d]imidazol-2(3H)-one obtained in Step 38-4 was used instead of 7-nitroisoquinolin-1(2H)-one.

$^1$H NMR (400 MHz, DMSO-$d_6$) δ 6.82 (d, J=8.2 Hz, 1H), 6.35 (d, J=2.1 Hz, 1H), 6.30 (dd, J=8.2 Hz, 2.1 Hz, 1H), 4.78 (s, 2H), 3.75 (q, J=7.1 Hz, 2H), 3.20 (s, 3H), 1.15 (t, J=7.1 Hz, 3H).

Step 38-6: Preparation of (1-ethyl-3-methyl-2-oxo-2,3-dihydro-1H-benzo[d]imidazol-5-yl)carbonohydrazonoyl dicyanide 10.8 mg (yield: 6%) of the title compound was obtained in the same manner as in Step 1-3 of Example 1 above, except that 5-amino-1-ethyl-3-methyl-1H-benzo[d]imidazol-2(3H)-one obtained in Step 38-5 was used instead of 7-aminoisoquinolin-1(2H)-one.

$^1$H NMR (400 MHz, DMSO-$d_6$) δ 13.07 (s, 1H), 7.26-7.22 (m, 3H), 3.86 (q, J=7.2 Hz, 2H), 1.20 (t, J=7.1 Hz, 3H).

EXAMPLE 39: PREPARATION OF (3-(DIFLUOROMETHYL)-1-ETHYL-2-OXO-2,3-DIHYDRO-1H-BENZO[D]IMIDAZOL-5-YL)CARBONOHYDRAZONOYL DICYANIDE (COMPOUND 39)

Step 39-1: Preparation of 3-difluoromethyl-1-ethyl-5-nitro-1H-benzo[d]imidazol-2(3H)-one 133.0 mg (yield: 42%) of the title compound was obtained in the same manner as in Step 37-1 of Example 37 above, except that 1-ethyl-5-nitro-1H-benzo[d]imidazol-2(3H)-one obtained in Step 38-3 of Example 38 was used instead of 1-methyl-5-nitro-1H-benzo[d]imidazol-2(3H)-one.

$^1$H NMR (400 MHz, DMSO-$d_6$) δ 8.22 (dd, J=8.8 Hz, 2.2 Hz, 1H), 8.06 (d, J=2.2 Hz, 1H), 7.81 (t, J=57.5 Hz, 1H), 7.60 (d, J=8.9 Hz, 1H), 3.97 (q, J=7.2 Hz, 2H), 1.26 (t, J=7.2 Hz, 3H).

Step 39-2: Preparation of 5-amino-3-difluoromethyl-1-ethyl-1H-benzo[d]imidazol-2(3H)-one 88.2 mg (yield: 75%) of the title compound was obtained in the same manner as in Step 1-2 of Example 1 above, except that 3-difluoromethyl-1-ethyl-5-nitro-1H-benzo[d]imidazol-2(3H)-one obtained in Step 39-1 was obtained instead of 7-nitroisoquinolin-1(2H)-one.

$^1$H NMR (400 MHz, DMSO-$d_6$) δ 7.56 (t, J=58.3 Hz, 1H), 6.97 (d, J=8.4 Hz, 1H), 6.65 (d, J=2.0 Hz, 1H), 6.44 (dd, J=8.4 Hz, 2.1 Hz, 1H), 5.03 (s, 2H), 3.77 (q, J=7.2 Hz, 2H), 1.19 (t, J=7.2 Hz, 3H).

Step 39-3: Preparation of (3-difluoromethyl-1-ethyl-2-oxo-2,3-dihydro-1H-benzo[d]imidazol-5-yl)carbonohydrazonoyl dicyanide 64.7 mg (yield: 56%) of the title compound was obtained in the same manner as in Step 1-3 of Example 1 above, except that 5-amino-3-difluoromethyl-1-ethyl-1H-benzo[d]imidazol-2(3H)-one obtained in Step 39-2 was used instead of 7-aminoisoquinolin-1(2H)-one.

$^1$H NMR (400 MHz, Acetone-$d_6$) δ 11.85 (s, 1H), 7.57 (d, J=2.1 Hz, 1H), 7.52 (t, J=58.4 Hz, 1H), 7.44 (dd, J=8.6 Hz, 2.1 Hz, 1H), 7.37 (d, J=8.4 Hz, 1H), 3.97 (q, J=7.3 Hz, 2H), 1.32 (t, J=7.2 Hz, 3H).

EXAMPLE 40: PREPARATION OF (1-CYCLOPROPYL-3-METHYL-2-OXO-2,3-DIHYDRO-1H-BENZO[D]IMIDAZOL-5-YL)CARBONOHYDRAZONOYL DICYANIDE (COMPOUND 40)

Step 40-1: Preparation of N-cyclopropyl-2,4-dinitroaniline 179.9 mg (yield: 81%) of the title compound was obtained in the same manner as in Step 17-1 of Example 17 above, except that cyclopropylamine was used instead of methylamine.

$^1$H NMR (400 MHz, Chloroform-d) δ 9.13 (d, J=2.6 Hz, 1H), 8.56 (s, 1H), 8.31 (ddd, J=9.5 Hz, 2.6 Hz, 0.7 Hz, 1H), 7.40 (d, J=9.5 Hz, 1H), 2.70 (tdt, J=6.8 Hz, 3.8 Hz, 1.8 Hz, 1H), 1.12-0.98 (m, 2H), 0.82-0.67 (m, 2H).

Step 40-2: Preparation of $N^1$-cyclopropyl-4-nitrobenzene-1,2-diamine 1.69 g (yield: 89%) of the title compound was obtained in the same manner as in Step 17-2 of Example 17 above, except that N-cyclopropyl-2,4-dinitroaniline obtained in Step 40-1 above was used instead of N-methyl-2,4-dinitroaniline.

$^1$H NMR (400 MHz, Chloroform-d) δ 7.85 (ddd, J=8.9 Hz, 2.5 Hz, 0.6 Hz, 1H), 7.61 (d, J=2.5 Hz, 1H), 6.98 (d, J=8.9 Hz, 1H), 4.66 (s, 1H), 3.29 (s, 2H), 2.53 (ttd, J=6.7 Hz, 3.6 Hz, 1.3 Hz, 1H), 0.93-0.82 (m, 2H), 0.63-0.55 (m, 2H).

Step 40-3: Preparation of 1-cyclopropyl-5-nitro-1H-benzo[d]imidazol-2(3H)-one 1.83 g (yield: 96%) of the title compound was obtained in the same manner as in Step 9-1 of Example 9 above, except that N-cyclopropyl-4-nitrobenzene-1,2-diamine obtained in Step 40-2 was used instead of 4-fluoro-5-nitrobenzene-1,2-diamine.

$^1$H NMR (400 MHz, DMSO-$d_6$) δ 11.30 (s, 1H), 8.01 (dd, J=8.7 Hz, 2.3 Hz, 1H), 7.71 (d, J=2.3 Hz, 1H), 7.32 (d, J=8.7 Hz, 1H), 2.93 (tt, J=7.0 Hz, 3.7 Hz, 1H), 1.09-1.01 (m, 2H), 0.93-0.85 (m, 2H).

Step 40-4: Preparation of 1-cyclopropyl-3-methyl-5-nitro-1H-benzo[d]imidazol-2(3H-one 186.6 mg (yield: 87%) of the title compound was obtained in the same manner as in Step 35-1 of Example 35 above, except that 1-cyclopropyl-5-nitro-1H-benzo[d]imidazol-2(3H)-one obtained in Step 40-3 was used instead of 1-methyl-5-nitro-1H-benzo[d]imidazol-2(3H)-one, and methyl iodide was used instead of ethyl iodide.

$^1$H NMR (400 MHz, Chloroform-d) δ 8.10 (ddd, J=8.6 Hz, 2.3 Hz, 1.0 Hz, 1H), 7.85 (d, J=2.0 Hz, 1H), 7.23 (s, 1H), 3.45 (d, J=1.0 Hz, 3H), 2.93 (tdd, J=7.1 Hz, 4.1 Hz, 3.1 Hz, 1H), 1.22-1.11 (m, 2H), 1.07-0.98 (m, 2H).

Step 40-5: Preparation of 5-amino-1-cyclopropyl-3-methyl-H-benzo[d]imidazol-2(3H)-one 41.6 mg (yield: 75%) of the title compound was obtained in the same manner as in Step 1-2 of Example 1 above, except that 1-cyclopropyl-3-methyl-5-nitro-1H-benzo[d]imidazol-2(3H)-one obtained in Step 40-4 was used instead of 7-nitroisoquinolin-1(2H)-one, and methanol was used as a solvent instead of dioxane.

$^1$H NMR (400 MHz, Chloroform-d) δ 6.96 (d, J=8.2 Hz, 1H), 6.44 (dd, J=8.2 Hz, 2.1 Hz, 1H), 6.34 (d, J=2.1 Hz, 1H), 3.58 (s, 2H), 3.31 (s, 3H), 2.90-2.69 (m, 1H), 1.08-1.01 (m, 2H), 1.01-0.94 (m, 2H).

Step 40-6: Preparation of (1-cyclopropyl-3-methyl-2-oxo-2,3-dihydro-1H-benzo[d]imidazol-5-yl)carbonohydrazonoyl dicyanide 29.9 mg (yield: 52%) of the title compound was obtained in the same manner as in Step 1-3 of Example 1 above, except that 5-amino-1-cyclopropyl-3-methyl-1H-benzo[d]imidazol-2(3H)-one obtained in Step 40-5 was used instead of 7-aminoisoquinolin-1(2H)-one.

$^1$H NMR (400 MHz, Chloroform-d) δ 9.86 (s, 1H), 7.18 (d, J=8.3 Hz, 1H), 7.05 (d, J=2.1 Hz, 1H), 6.95 (dd, J=8.4 Hz, 2.1 Hz, 1H), 3.41 (s, 3H), 2.89 (t, J=7.0 Hz, 3.7 Hz, 1H), 1.17-1.09 (m, 2H), 1.01 (tt, J=5.3 Hz, 3.7 Hz, 2H).

EXAMPLE 41: PREPARATION OF (1-CYCLOPROPYL-3-ETHYL-2-OXO-2,3-DIHYDRO-1H-BENZO[D]IMIDAZOL-5-YL)CARBONOHYDRAZONOYL DICYANIDE (COMPOUND 41)

Step 41-1: Preparation of 1-cyclopropyl-3-ethyl-5-nitro-1H-benzo[d]imidazol-2(3H)-one 159.9 mg (yield: 70%) of the title compound was obtained in the same manner as in Step 35-1 of Example 35 above, except that 1-cyclopropyl-5-nitro-1H-benzo[d]imidazol-2(3H)-one obtained in Step 40-3 was used instead of 1-methyl-5-nitro-1H-benzo[d]imidazol-2(3H)-one.

$^1$H NMR (400 MHz, DMSO-$d_6$) δ 8.09 (d, J=2.2 Hz, 1H), 8.07 (dd, J=8.6 Hz, 2.3 Hz, 1H), 7.38 (d, J=8.6 Hz, 1H), 3.94 (q, J=7.1 Hz, 2H), 2.98 (tt, J=7.1 Hz, 3.7 Hz, 1H), 1.21 (t, J=7.2 Hz, 3H), 1.12-1.03 (m, 2H), 0.95-0.86 (m, 2H).

Step 41-2: Preparation of 5-amino-1-cyclopropyl-3-ethyl-H-benzo[d]imidazol-2(3H)-one 83.2 mg (yield: 61%) of the title compound was obtained in the same manner as in Step 1-2 of Example 1 above, except that 1-cyclopropyl-3-ethyl-5-nitro-1H-benzo[d]imidazol-2(3H)-one obtained in Step 41-1 was used instead of 7-nitroisoquinolin-1(2H)-one, and methanol was used as a solvent instead of dioxane.

$^1$H NMR (400 MHz, Chloroform-d) δ 6.96 (d, J=8.2 Hz, 1H), 6.43 (dd, J=8.2 Hz, 2.2 Hz, 1H), 6.37 (d, J=2.1 Hz, 1H), 3.83 (q, J=7.2 Hz, 2H), 3.58 (br s, 2H), 2.90-2.72 (m, 1H), 1.28 (t, J=7.2 Hz, 3H), 1.08-0.94 (m, 4H).

Step 41-3: Preparation of (1-cyclopropyl-3-ethyl-2-oxo-2,3-dihydro-1H-benzo[d]imidazol-5-yl)carbonohydrazonoyl dicyanide 53.6 mg (yield: 49%) of the title compound was obtained in the same manner as in Step 1-3 of Example 1 above, except that 5-amino-1-cyclopropyl-3-ethyl-1H-benzo[d]imidazol-2(3H)-one obtained in Step 41-2 was used instead of 7-aminoisoquinolin-1(2H)-one.

$^1$H NMR (400 MHz, DMSO-$d_6$) δ 13.04 (s, 1H), 7.52-7.06 (m, 3H), 3.83 (q, J=7.2 Hz, 2H), 2.89 (tt, J=7.0 Hz, 3.7 Hz, 1H), 1.18 (t, J=7.2 Hz, 3H), 1.02 (td, J=7.3 Hz, 5.0 Hz, 2H), 0.92-0.82 (m, 2H).

EXAMPLE 42: PREPARATION OF (1-CYCLOPROPYL-3-ISOPROPYL-2-OXO-2,3-DIHYDRO-1H-BENZO[D]IMIDAZOL-5-YL)CARBONOHYDRAZONOYL DICYANIDE (COMPOUND 42)

Step 42-1: Preparation of 1-cyclopropyl-3-isoproplyl-5-nitro-1H-benzo[d]imidazol-2(3H)-one 207.5 mg (yield: 69%) of the title compound was obtained in the same manner as in Step 35-1 of Example 35 above, except that 1-cyclopropyl-5-nitro-1H-benzo[d]imidazol-2(3H)-one obtained in Step 40-3 was used instead of 1-methyl-5-nitro-1H-benzo[d]imidazol-2(3H)-one, and isopropyl iodide was used instead of ethyl iodide.

$^1$H NMR (400 MHz, DMSO-$d_6$) δ 8.17 (d, J=2.3 Hz, 1H), 8.03 (dd, J=8.8 Hz, 2.2 Hz, 1H), 7.51 (d, J=8.8 Hz, 1H), 5.27 (hept, J=6.2 Hz, 1H), 3.18 (tt, J=7.1 Hz, 3.7 Hz, 1H), 1.43 (d, J=6.2 Hz, 6H), 1.13 (td, J=7.4 Hz, 5.2 Hz, 2H), 0.98-0.90 (m, 2H).

Step 42-2: Preparation of 5-amino-1-cyclopropyl-3-isopropyl-H-benzo[d]imidazol-2(3H)-one 114.5 mg (yield: 62%) of the title compound was obtained in the same manner as in Step 1-2 of Example 1 above, except that 1-cyclopropyl-3-isopropyl-5-nitro-1H-benzo[d]imidazol-2(3H)-one obtained in Step 42-1 was used instead of 7-nitroisoquinolin-1(2H)-one, and methanol was used as a solvent instead of dioxane.

$^1$H NMR (400 MHz, Chloroform-d) δ 6.97 (d, J=8.2 Hz, 1H), 6.52 (d, J=2.1 Hz, 1H), 6.43 (dd, J=8.2 Hz, 2.1 Hz, 1H), 4.65 (hept, J=7.0 Hz, 1H), 3.56 (s, 2H), 2.84-2.71 (m, 1H), 1.48 (d, J=7.0 Hz, 6H), 1.07-0.94 (m, 4H).

Step 42-3: Preparation of (1-cyclopropyl-3-isopropyl-2-oxo-2,3-dihydro-1H-benzo[d]imidazol-5-yl) carbonohydrazonoyl dicyanide 39.8 mg (yield: 26%) of the title compound was obtained in the same manner as in Step 1-3 of Example 1 above, except that 5-amino-1-cyclopropyl-3-isopropyl-1H-benzo[d]imidazol-2(3H)-one obtained in Step 42-2 was used instead of 7-aminoisoquinolin-1(2H)-one.

$^1$H NMR (400 MHz, DMSO-$d_6$) δ 12.96 (s, 1H), 7.39 (d, J=1.3 Hz, 1H), 7.22 (d, J=1.2 Hz, 2H), 4.58 (hept, J=6.9 Hz, 1H), 2.87 (tt, J=7.0 Hz, 3.6 Hz, 1H), 1.42 (d, J=6.9 Hz, 6H), 1.01 (td, J=7.2 Hz, 5.0 Hz, 2H), 0.90-0.82 (m, 2H).

EXAMPLE 43: PREPARATION OF (3-(DIFLUOROMETHYL)-1-ISOPROPYL-2-OXO-2,3-DIHYDRO-1H-BENZO[D]IMIDAZOL-5-YL)CARBONOHYDRAZONOYL DICYANIDE (COMPOUND 43)

Step 43-1: Preparation of N-Isopropyl-2,4-dinitroaniline 2.02 g (yield: 90%) of the title compound was obtained in the same manner as in Step 17-1 of Example 17 above, except that isopropylamine was used instead of methylamine.

$^1$H NMR (400 MHz, Chloroform-d) δ 9.14 (d, J=2.7 Hz, 1H), 8.50 (s, 1H), 8.26 (ddd, J=9.6 Hz, 2.7 Hz, 0.8 Hz, 1H), 6.93 (d, J=9.6 Hz, 1H), 4.00-3.89 (m, 1H), 1.40 (d, J=6.4 Hz, 6H).

Step 43-2: Preparation of $N^1$-isopropyl-4-nitrobenzene-1,2-diamine 1.08 g (yield: 62%) of the title compound was obtained in the same manner as in Step 17-2 of Example 17 above, except that N-isopropyl-2,4-dinitroaniline obtained in Step 43-1 was used instead of N-methyl-2,4-dinitroaniline, and a mixed solution of methanol and water in a ratio of 1:1 was used as a solvent.

$^1$H NMR (400 MHz, Chloroform-d) δ 7.84 (dd, J=8.9 Hz, 2.6 Hz, 1H), 7.63 (d, J=2.6 Hz, 1H), 6.55 (d, J=9.0 Hz, 1H), 4.20 (s, 1H), 3.82-3.63 (m, J=6.3 Hz, 1H), 3.29 (s, 2H), 1.29 (d, J=6.3 Hz, 6H).

Step 43-3: Preparation of 1-Isopropyl-5-nitro-1H-benzo[d]imidazol-2(3H)-one 1.15 g (yield: 94%) of the title compound was obtained in the same manner as in Step 9-1 of Example 9 above, except that N-isopropyl-4-nitrobenzene-1,2-diamine obtained in Step 43-2 was used instead of 4-fluoro-5-nitrobenzene-1,2-diamine.

$^1$H NMR (400 MHz, DMSO-$d_6$) δ 11.42 (s, 1H), 7.96 (dd, J=8.8 Hz, 2.4 Hz, 1H), 7.74 (d, J=2.3 Hz, 1H), 7.47 (d, J=8.8 Hz, 1H), 4.63 (hept, J=6.9 Hz, 1H), 1.46 (d, J=7.0 Hz, 6H).

Step 43-4: Preparation of 3-difluoromethyl-1-isopropyl-5-nitro-1H-benzo[d]imidazol-2(3H)-one 89.3 mg (yield: 29%) of the title compound was obtained in the same manner as in Step 37-1 of Example 37 above, except that 1-isopropyl-5-nitro-1H-benzo[d]imidazol-2(3H)-one obtained in Step 43-3 was used instead of 1-methyl-5-nitro-1H-benzo[d]imidazol-2(3H)-one.

$^1$H NMR (400 MHz, DMSO-$d_6$) δ 8.17 (dd, J=8.9 Hz, 2.3 Hz, 1H), 8.05 (d, J=2.3 Hz, 1H), 7.79 (t, J=57.6 Hz, 1H), 7.69 (d, J=8.9 Hz, 1H), 4.68 (hept, J=6.9 Hz, 1H), 1.49 (d, J=6.9 Hz, 6H).

Step 43-5: Preparation of 5-amino-3-difluoromethyl-1-ethyl-H-benzo[d]imidazol-2(3H)-one 67.2 mg (yield: 84%) of the title compound was obtained in the same manner as in Step 1-2 of Example 1 above, except that 3-difluoromethyl-1-ethyl-5-nitro-1H-benzo[d]imidazol-2(3H)-one obtained in Step 43-4 was used instead of 7-nitroisoquinolin-1(2H)-one, and methanol was used as a solvent instead of dioxane.

$^1$H NMR (400 MHz, DMSO-$d_6$) δ 7.53 (t, J=58.4 Hz, 1H), 7.07 (d, J=8.5 Hz, 1H), 6.65 (d, J=2.1 Hz, 1H), 6.42 (dd, J=8.5 Hz, 2.1 Hz, 1H), 5.03 (s, 2H), 4.49 (hept, J=6.9 Hz, 1H), 1.41 (d, J=6.9 Hz, 6H).

Step 43-6: Preparation of (1-ethyl-3-methyl-2-oxo-2,3-dihydro-1H-benzo[d]imidazol-5-yl)carbonohydrazonoyl dicyanide 53.6 mg (yield: 60%) of the title compound was obtained in the same manner as in Step 1-3 of Example 1 above, except that 5-amino-3-difluoromethyl-1-ethyl-1H-benzo[d]imidazol-2(3H)-one obtained in Step 43-5 was used instead of 7-aminoisoquinolin-1(2H)-one, and water was used as a solvent.

$^1$H NMR (400 MHz, DMSO-$d_6$) δ 13.10 (s, 1H), 7.69 (t, J=57.8 Hz, 1H), 7.53-7.44 (m, 2H), 7.35 (dd, J=8.8 Hz, 2.1 Hz, 1H), 4.59 (p, J=6.9 Hz, 1H), 1.46 (d, J=7.0 Hz, 6H).

EXAMPLE 44: PREPARATION OF (1-ETHYL-3-METHYL-2-OXO-2,3-DIHYDRO-1H-IMIDAZO[4,5-B]PYRIDIN-6-YL)CARBONOHYDRAZONOYL DICYANIDE (COMPOUND 44)

Step 44-1: Preparation of N-methyl-3,5-dinitropyridine-2-amine 1.62 g (yield: 83%) of the title compound was obtained in the same manner as in Step 17-1 of Example 17 above, except that 2-chloro-3,5-dinitropyridine was used instead of 1-chloro-2,4-dinitrobenzene.

$^1H$ NMR (400 MHz, Acetone-$d_6$) δ 9.27 (d, J=2.6 Hz, 1H), 9.13 (s, 1H), 9.10 (d, J=2.6 Hz, 1H), 3.30 (d, J=1.2 Hz, 3H).

Step 44-2: Preparation of $N^1$-methyl-5-nitropyridine-2,3-diamine 1.14 g (yield: 83%) of the title compound was obtained in the same manner as in Step 17-2 of Example 17 above, except that N-methyl-3,5-dinitropyridine-2-amine obtained in Step 44-1 was used instead of N-methyl-2,4-dinitroaniline.

$^1H$ NMR (400 MHz, DMSO-$d_6$) δ 8.40 (d, J=2.5 Hz, 1H), 7.34 (d, J=2.6 Hz, 1H), 7.12 (s, 1H), 5.32 (s, 2H), 2.97 (d, J=4.6 Hz, 3H).

Step 44-3: Preparation of 3-methyl-6-nitro-1H-imidazo[4,5-b]pyridin-2(3H)-one 669.7 mg (yield: 53%) of the title compound was obtained in the same manner as in Step 9-1 of Example 9 above, except that N-methyl-5-nitropyridine-2,3-diamine obtained in Step 44-2 was used instead of 4-fluoro-5-nitrobenzene-1,2-diamine.

$^1H$ NMR (400 MHz, DMSO-$d_6$) δ 11.69 (s, 1H), 8.92 (d, J=2.3 Hz, 1H), 7.92 (d, J=2.3 Hz, 1H), 3.36 (s, 3H).

Step 44-4: Preparation of 1-ethyl-3-methyl-6-nitro-1H-Imidazo[4,5-b]pyridin-2(3H)-one 148.8 mg (yield: 65%) of the title compound was obtained in the same manner as in Step 35-1 of Example 35 above, except that 3-methyl-6-nitro-1H-imidazo[4,5-b]pyridin-2(3H)-one obtained in Step 44-3 was used instead of 1-methyl-5-nitro-1H-benzo[d]imidazol-2(3H)-one.

$^1H$ NMR (400 MHz, Chloroform-d) δ 9.03 (d, J=2.2 Hz, 1H), 7.96 (d, J=2.2 Hz, 1H), 4.01 (q, J=7.3 Hz, 2H), 3.56 (s, 3H), 1.40 (t, J=7.3 Hz, 3H).

Step 44-5: Preparation of 6-amino-1-ethyl-3-methyl-1H-imidazo[4,5-b]pyridin-2(3H-one 92.8 mg (yield: 74%) of the title compound was obtained in the same manner as in Step 1-2 of Example 1 above, except 1-ethyl-3-methyl-6-nitro-1H-imidazo[4,5-b]pyridin-2(3H)-one obtained in Step 44-4 was used instead of 7-nitroisoquinolin-1(2H)-one, methanol was used as a solvent instead of dioxane, and the reaction was performed at 40° C.

$^1H$ NMR (400 MHz, Chloroform-d) δ 7.56 (d, J=2.2 Hz, 1H), 6.65 (d, J=2.3 Hz, 1H), 3.88 (q, J=7.3 Hz, 2H), 3.52 (s, 2H), 3.43 (s, 3H), 1.31 (t, J=7.2 Hz, 3H).

Step 44-6: Preparation of (1-cyclopropyl-3-methyl-2-oxo-2,3-dihydro-1H-benzo[d]imidazol-5-yl)carbonohydrazonoyl dicyanide 45.8 mg (yield: 31%) of the title compound was obtained in the same manner as in Step 1-3 of Example 1 above, except that 6-amino-1-ethyl-3-methyl-1H-imidazo[4,5-b]pyridin-2(3H)-one obtained in Step 44-5 was used instead of 7-aminoisoquinolin-1(2H)-one.

$^1H$ NMR (400 MHz, DMSO-$d_6$) δ 13.10 (s, 1H), 8.16 (d, J=2.1 Hz, 1H), 7.62 (d, J=2.1 Hz, 1H), 3.92 (q, J=7.1 Hz, 2H), 3.33 (s, 4H), 1.20 (t, J=7.1 Hz, 3H).

EXAMPLE 45: PREPARATION OF (1-ISOPROPYL-3-METHYL-2-OXO-2,3-DIHYDRO-1H-IMIDAZO[4,5-B]PYRIDIN-6-YL)CARBONOHYDRAZONOYL DICYANIDE (COMPOUND 45)

Step 45-1: Preparation of 1-isopropyl-3-methyl-6-nitro-1H-imidazo[4,5-b]pyridin-2(3H)-one 98.5 mg (yield: 40%) of the title compound was obtained in the same manner as in Step 35-1 of Example 35 above, except that 3-methyl-6-nitro-1H-imidazo[4,5-b]pyridin-2(3H)-one obtained in Step 44-3 of Example 44 was used instead of 1-methyl-5-nitro-1H-benzo[d]imidazol-2(3H)-one.

$^1H$ NMR (400 MHz, Chloroform-d) δ 9.01 (d, J=2.2 Hz, 1H), 8.05 (d, J=2.3 Hz, 1H), 4.76 (hept, J=7.0 Hz, 1H), 3.54 (s, 3H), 1.57 (d, J=7.0 Hz, 6H).

Step 45-2: Preparation of 6-amino-1-Isopropyl-3-methyl-1H-Imidazo[4,5-b]pyridin-2(3H)-one 64.1 mg (yield: 81%) of the title compound was obtained in the same manner as in Step 1-2 of Example 1 above, except that 1-isopropyl-3-methyl-6-nitro-1H-imidazo[4,5-b]pyridin-2(3H)-one obtained in Step 45-1 was used instead of 7-nitroisoquinolin-1(2H)-one, and ethyl acetate was used as a solvent instead of dioxane.

$^1H$ NMR (400 MHz, Chloroform-d) δ 7.55 (d, J=2.3 Hz, 1H), 6.78 (d, J=2.2 Hz, 1H), 4.71 (hept, J=7.0 Hz, 1H), 3.51 (s, 2H), 3.41 (s, 3H), 1.48 (d, J=7.0 Hz, 6H).

Step 45-3: Preparation of (1-isopropyl-3-methyl-2-oxo-2,3-dihydro-1H-imidazo[4,5-b]pyridin-6-yl) carbonohydrazonoyl dicyanide 8.6 mg (yield: 9%) of the title compound was obtained in the same manner as in Step 1-3 of Example 1 above, except that 5-amino-1-cyclopropyl-3-ethyl-1H-benzo[d]imidazol-2(3H)-one obtained in Step 45-2 was used instead of 7-aminoisoquinolin-1(2H)-one.

$^1H$ NMR (400 MHz, DMSO-$d_6$) δ 13.10 (s, 1H), 8.15 (d, J=2.1 Hz, 1H), 7.66 (d, J=2.1 Hz, 1H), 4.64 (hept, J=6.9 Hz, 1H), 3.32 (s, 3H), 1.44 (d, J=6.9 Hz, 6H).

EXAMPLE 46: PREPARATION OF (1-(DIFLUOROMETHYL)-3-METHYL-2-OXO-2,3-DIHYDRO-1H-IMIDAZO[4,5-B]PYRIDIN-6-YL) CARBONOHYDRAZONOYL DICYANIDE (COMPOUND 46)

Step 46-1: Preparation of 1-difluoromethyl-3-methyl-6-nitro-1H-imidazo[4,5-b]pyridin-2(3H)-one 58.5 mg (yield: 46%) of the title compound was obtained in the same manner as in Step 37-1 of Example 37 above, except that 3-methyl-1-nitro-1H-imidazo[4,5-b]pyridin-2(3H)-one obtained in Step 44-3 of Example 44 was used instead of 1-methyl-5-nitro-1H-benzo[d]imidazol-2(3H)-one.

$^1$H NMR (400 MHz, DMSO-$d_6$) δ 9.11 (d, J=2.3 Hz, 1H), 8.25 (d, J=2.3 Hz, 1H), 7.87 (t, J=57.4 Hz, 1H), 3.40 (s, 3H).

Step 46-2: Preparation of 6-amino-1-difluoromethyl-3-methyl-1H-imidazo[4,5-b]pyridin-2(3H)-one 121.1 mg (yield: 88%) of the title compound was obtained in the same manner as in Step 1-2 of Example 1 above, except that 1-difluoromethyl-3-methyl-6-nitro-1H-imidazo[4,5-b]pyridin-2(3H)-one obtained in Step 46-1 was used instead of 7-nitroisoquinolin-1(2-H)-one, and methanol was used as a solvent instead of dioxane.

$^1$H NMR (400 MHz, Chloroform-d) δ 7.66 (d, J=2.4 Hz, 1H), 7.31 (t, J=58.9 Hz, 1H), 7.02 (d, J=2.3 Hz, 1H), 3.62 (s, 2H), 3.42 (s, 3H).

Step 46-3: Preparation of (1-difluoromethyl-3-methyl-2-oxo-2,3-dihydro-1H-imidazo[4,5-b]pyridin-6-yl)carbonohydrazonoyl dicyanide 57.3 mg (yield: 81%) of the title compound was obtained in the same manner as in Step 1-3 of Example 1 above, except that 6-amino-1-difluoromethyl-3-methyl-1H-imidazo[4,5-b]pyridin-2(3H)-one obtained in Step 46-2 was used instead of 7-aminoisoquinolin-1(2H)-one.

$^1$H NMR (400 MHz, DMSO-$d_6$) δ 8.29 (d, J=2.1 Hz, 1H), 7.79 (t, J=57.6 Hz, 1H), 7.68 (d, J=2.1 Hz, 1H), 3.33 (s, 3H).

EXAMPLE 47: PREPARATION OF (3-METHYL-2-OXO-1-PHENYL-2,3-DIHYDRO-1H-IMIDAZO[4,5-B]PYRIDIN-6-YL)CARBONOHYDRAZONOYL DICYANIDE (COMPOUND 47)

Step 47-1: Preparation of 3-methyl-6-nitro-1-phenyl-1H-imidazo[4,5-b]pyridin-2(3H)-one 3-Methyl-6-nitro-1H-imidazo[4,5-b]pyridin-2(3H)-one (50 mg, 0.26 mmol) obtained in Step 44-3 of Example 44, potassium carbonate (71.2 mg, 0.52 mmol), copper iodide (9.8 mg, 0.052 mmol), and trans-4-hydroxy-L-proline (13.5 mg, 0.10 mmol) were dissolved in DMSO, and benzene iodide (28.7 mg, 0.26 mmol) dissolved in DMSO was slowly added thereto. The reaction mixture was heated to 130° C. and stirred for 14 hours. Upon completion of the reaction, a reaction product was extracted using a saturated aqueous solution of ammonium chloride and ethyl acetate to obtain an organic layer, and the organic layer was dried with anhydrous magnesium sulfate and filtered. The filtrate was concentrated under reduced pressure, and the crude material was purified by column chromatography to obtain 36.6 mg (yield: 52%) of the title compound.

$^1$H NMR (400 MHz, DMSO-$d_6$) δ 9.05 (d, J=2.3 Hz, 1H), 7.88 (d, J=2.3 Hz, 1H), 7.63 (d, J=5.7 Hz, 4H), 7.58-7.47 (m, 1H), 3.50 (s, 3H).

Step 47-2: Preparation of 6-amino-3-methyl-1-phenyl-1H-imidazo[4,5-b]pyridin-2(3H)-one 18.2 mg (yield: 34%) of the title compound was obtained in the same manner as in Step 1-2 of Example 1 above, except that 3-methyl-6-nitro-1-phenyl-1H-imidazo[4,5-b]pyridin-2(3H)-one obtained in Step 47-1 was used instead of 7-nitroisoquinolin-1(2H)-one, DMF was used as a solvent instead of dioxane, and the reaction was performed at 60° C.

$^1$H NMR (400 MHz, DMSO-$d_6$) δ 7.61-7.49 (m, 4H), 7.46 (d, J=2.3 Hz, 1H), 7.45-7.41 (m, 1H), 6.73 (d, J=2.2 Hz, 1H), 4.96 (s, 2H), 3.32 (s, 3H).

Step 47-3: Preparation of (1-difluoromethyl-3-methyl-2-oxo-2,3-dihydro-1H-Imidazo[4,5-b]pyridin-6-yl)carbonohydrazonoyl dicyanide 14.0 mg (yield: 58%) of the title compound was obtained in the same manner as in Step 1-3 of Example 1 above, except that 6-amino-3-methyl-1-phenyl-1H-imidazo[4,5-b]pyridin-2(3H)-one obtained in Step 47-2 was used instead of 7-aminoisoquinolin-1(2H)-one.

$^1$H NMR (400 MHz, Acetone-$d_6$) δ 11.91 (s, 1H), 8.26 (d, J=2.2 Hz, 1H), 7.67-7.56 (m, 4H), 7.53 (d, J=2.2 Hz, 1H), 7.48 (tt, J=6.1 Hz, 2.2 Hz, 1H), 3.48 (s, 3H).

EXAMPLE 48: PREPARATION OF (3-ETHYL-1-METHYL-2-OXO-2,3-DIHYDRO-1H-IMIDAZO[4,5-B]PYRIDIN-6-YL)CARBONOHYDRAZONOYL DICYANIDE (COMPOUND 48)

Step 48-1: Preparation of N-ethyl-3,5-dinitropyridine-2-amine 1.66 g (yield: 79%) of the title compound was obtained in the same manner as in Step 17-1 of Example 17 above, except that 2-chloro-3,5-dinitropyridine was used instead of 1-chloro-2,4-dinitrobenzene, and ethylamine was used instead of methylamine.

$^1$H NMR (400 MHz, Chloroform-d) δ 9.26 (d, J=2.6 Hz, 1H), 9.22 (d, J=2.6 Hz, 1H), 8.73 (s, 1H), 3.80 (qd, J=7.2 Hz, 5.6 Hz, 2H), 1.37 (t, J=7.3 Hz, 3H).

Step 48-2: Preparation of N-ethyl-5-nitropyridine-2,3-diamine 1.15 g (yield: 80%) of the title compound was obtained in the same manner as in Step 17-2 of Example 17 above, except that N-ethyl-3,5-dinitropyridine-2-amine obtained in Step 48-1 was used instead of N-methyl-2,4-dinitroaniline, and a mixed solution of methanol and water in a ratio of 1:1 was used as a solvent.

$^1$H NMR (400 MHz, Chloroform-d) δ 8.74 (d, J=2.4 Hz, 1H), 7.60 (d, J=2.4 Hz, 1H), 5.02 (s, 1H), 3.61 (qd, J=7.2 Hz, 5.4 Hz, 2H), 3.30 (s, 2H), 1.31 (t, J=7.2 Hz, 3H).

Step 48-3: Preparation of 3-ethyl-6-nitro-1H-imidazo[4,5-b]pyridin-2(3H)-one 891.8 mg (yield: 68%) of the title compound was obtained in the same manner as in Step 9-1 of Example 9 above, except that N-ethyl-5-nitropyridine-2,3-diamine obtained in Step 48-2 was used instead of 4-fluoro-5-nitrobenzene-1,2-diamine.

$^1$H NMR (400 MHz, DMSO-$d_6$) δ 11.69 (s, 1H), 8.93 (d, J=2.4 Hz, 1H), 7.93 (d, J=2.3 Hz, 1H), 3.92 (q, J=7.2 Hz, 2H), 1.27 (t, J=7.2 Hz, 3H).

Step 48-4: Preparation of 3-ethyl-1-methyl-6-nitro-1H-imidazo[4,5-b]pyridin-2(3H)-one 127.8 mg (yield: 80%) of the title compound was obtained in the same manner as in Step 35-1 of Example 35 above, except that 3-ethyl-6-nitro-1H-imidazo[4,5-b]pyridin-2(3H)-one obtained in Step 48-3 was used instead of 1-methyl-5-nitro-1H-benzo[d]imidazol-2(3H)-one, and methyl iodide was used instead of ethyl iodide.

$^1$H NMR (400 MHz, Chloroform-d) δ 9.03 (d, J=2.2 Hz, 1H), 7.94 (d, J=2.2 Hz, 1H), 4.11 (q, J=7.2 Hz, 2H), 3.50 (s, 3H), 1.41 (t, J=7.2 Hz, 3H).

Step 48-5: Preparation of 6-amino-3-ethyl-1-methyl-1H-imidazo[4,5-b]pyridin-2(3H)-one 94.8 mg (yield: 87%) of the title compound was obtained in the same manner as in Step 1-2 of Example 1 above, except that 3-ethyl-1-methyl-6-nitro-1H-imidazo[4,5-b]pyridin-2(3H)-one obtained in Step 48-4 was used instead of 7-nitroisoquinolin-1(2H)-one, and ethyl acetate was used as a solvent instead of dioxane.

$^1$H NMR (400 MHz, Chloroform-d) δ 7.55 (d, J=2.3 Hz, 1H), 6.61 (d, J=2.3 Hz, 1H), 3.98 (q, J=7.2 Hz, 2H), 3.53 (s, 2H), 3.35 (s, 3H), 1.34 (t, J=7.2 Hz, 3H).

Step 48-6: Preparation of (3-ethyl-1-methyl-2-oxo-2,3-dihydro-1H-imidazo[4,5-b]pyridin-6-yl)carbonohydrazonoyl dicyanide 61.6 mg (yield: 46%) of the title compound was obtained in the same manner as in Step 1-3 of Example 1 above, except that 6-amino-3-ethyl-1-methyl-1H-imidazo[4,5-b]pyridin-2(3H)-one obtained in Step 48-5 was used instead of 7-aminoisoquinolin-1(2H)-one.

$^1$H NMR (400 MHz, Acetone-$d_6$) δ 8.15 (d, J=2.2 Hz, 1H), 7.61 (d, J=2.2 Hz, 1H), 3.96 (q, J=7.2 Hz, 2H), 3.45 (s, 3H), 1.31 (t, J=7.2 Hz, 3H).

EXAMPLE 49: PREPARATION OF (3-ETHYL-1-ISOPROPYL-2-OXO-2,3-DIHYDRO-1H-IMIDAZO[4,5-B]PYRIDIN-6-YL)CARBONOHYDRAZONOYL DICYANIDE (COMPOUND 49)

Step 49-1: Preparation of 3-ethyl-1-isopropyl-6-nitro-1H-imidazo[4,5-b]pyridin-2(3H)-one 108.3 mg (yield: 45%) of the title compound was obtained in the same manner as in Step 48-4 of Example 48 above, except that isopropyl iodide was used instead of methyl iodide.

$^1$H NMR (400 MHz, Chloroform-d) δ 9.01 (d, J=2.2 Hz, 1H), 8.05 (d, J=2.2 Hz, 1H), 4.77 (hept, J=7.0 Hz, 1H), 4.10 (q, J=7.2 Hz, 2H), 1.57 (d, J=7.1 Hz, 6H), 1.41 (t, J=7.2 Hz, 3H).

Step 49-2: Preparation of 6-amino-3-ethyl-1-isopropyl-1H-imidazo[4,5-b]pyridin-2(3H)-one 75.2 mg (yield: 82%) of the title compound was obtained in the same manner as in Step 1-2 of Example 1 above, except that 3-ethyl-1-isopropyl-6-nitro-1H-imidazo[4,5-b]pyridin-2(3H)-one obtained in Step 49-1 was used instead of 7-nitroisoquinolin-1(2H)-one, and ethyl acetate was used as a solvent instead of dioxane.

$^1$H NMR (400 MHz, Chloroform-d) δ 7.54 (d, J=2.3 Hz, 1H), 6.78 (d, J=2.2 Hz, 1H), 4.71 (hept, J=7.0 Hz, 1H), 3.97 (q, J=7.2 Hz, 2H), 3.51 (s, 2H), 1.48 (d, J=7.0 Hz, 6H), 1.34 (t, J=7.2 Hz, 3H).

Step 49-3: Preparation of (3-ethyl-1-isopropyl-2-oxo-2,3-dihydro-1H-imidazo[4,5-b]pyridin-6-yl)carbonohydrazonoyl dicyanide 43.5 mg (yield: 42%) of the title compound was obtained in the same manner as in Step 1-3 of Example 1 above, except that 6-amino-3-ethyl-1-isopropyl-1H-imidazo[4,5-b]pyridin-2(3H)-one obtained in Step 49-2 was used instead of 7-aminoisoquinolin-1(2H)-one, and water was used as a solvent.

$^1$H NMR (400 MHz, Acetone-$d_6$) δ 11.89 (s, 1H), 8.16 (d, J=2.2 Hz, 1H), 7.72 (d, J=2.2 Hz, 1H), 4.72 (hept, J=6.9 Hz, 1H), 3.95 (q, J=7.2 Hz, 2H), 1.52 (d, J=7.0 Hz, 6H), 1.30 (t, J=7.2 Hz, 3H).

EXAMPLE 50: PREPARATION OF (1-(DIFLUOROMETHYL)-3-ETHYL-2-OXO-2,3-DIHYDRO-1H-IMIDAZO[4,6-B]PYRIDIN-6-YL)CARBONOHYDRAZONOYL DICYANIDE (COMPOUND 50)

Step 50-1: Preparation of 1-difluoromethyl-3-ethyl-6-nitro-1H-imidazo[4,5-b]pyridin-2(3H)-one 129.6 mg (yield: 70%) of the title compound was obtained in the same manner as in Step 37-1 of Example 37 above, except that 3-ethyl-6-nitro-1H-imidazo[4,5-b]pyridin-2(3H)-one obtained in Step 48-3 of Example 48 was used instead of 1-methyl-5-nitro-1H-benzo[d]imidazol-2(3H)-one.

$^1$H NMR (400 MHz, DMSO-$d_6$) δ 9.12 (d, J=2.3 Hz, 1H), 8.26 (d, J=2.3 Hz, 1H), 7.87 (t, J=57.4 Hz, 1H), 3.97 (q, J=7.2 Hz, 2H), 1.31 (t, J=7.2 Hz, 3H).

Step 50-2: Preparation of 6-amino-1-difluoromethyl-3-ethyl-1H-Imidazo[4,5-b]pyridin-2(3H)-one 103.7 mg (yield: 90%) of the title compound was obtained in the same manner as in Step 1-2 of Example 1 above, except that 1-difluoromethyl-3-ethyl-6-nitro-1H-benzo[d]imidazol-2(3H)-one obtained in Step 50-1 was used instead of 7-nitroisoquinolin-1(2H)-one.

$^1$H NMR (400 MHz, DMSO-$d_6$) δ 7.67 (t, J=58.2 Hz, 1H), 7.53 (d, J=2.2 Hz, 1H), 7.02 (d, J=2.2 Hz, 1H), 5.18 (s, 2H), 3.81 (q, J=7.2 Hz, 2H), 1.23 (t, J=7.2 Hz, 3H).

Step 50-3: Preparation of (3-difluoromethyl-1-ethyl-2-oxo-2,3-dihydro-1H-Imidazo[4,5-b]pyridin-6-yl)carbonohydrazonoyl dicyanide 69.3 mg (yield: 80%) of the title compound was obtained in the same manner as in Step 1-3 of Example 1 above, except that 6-amino-1-difluoromethyl-3-ethyl-1H-benzo[d]imidazol-2(3H)-one obtained in Step 50-2 was used instead of 7-aminoisoquinolin-1(2H)-one.

$^1$H NMR (400 MHz, DMSO-$d_6$) δ 8.30 (d, J=2.1 Hz, 1H), 7.79 (t, J=57.6 Hz, 1H), 7.70 (d, J=2.2 Hz, 1H), 3.90 (q, J=7.2 Hz, 2H), 1.28 (t, J=7.2 Hz, 3H).

EXAMPLE 51: PREPARATION OF (3-CYCLOPROPYL-1-METHYL-2-OXO-2,3-DIHYDRO-1H-IMIDAZO[4,5-B]PYRIDIN-6-YL)CARBONOHYDRAZONOYL DICYANIDE (COMPOUND 51)

Step 51-1: Preparation of N-cyclopropyl-3,5-dinitropyridine-2-amine 1.99 g (yield: 90%) of the title compound was obtained in the same manner as in Step 17-1 of Example 17 above, except that 2-chloro-3,5-dinitropyridine was used instead of 1-chloro-2,4-dinitrobenzene, and cyclopropylamine was used instead of methylamine.

$^1$H NMR (400 MHz, Chloroform-d) δ 9.32 (d, J=2.5 Hz, 1H), 9.21 (d, J=2.5 Hz, 1H), 8.69 (s, 1H), 3.21 (ddt, J=11.1 Hz, 7.1 Hz, 3.9 Hz, 1H), 1.11-0.97 (m, 2H), 0.80-0.64 (m, 2H).

Step 51-2: Preparation of $N^2$-cyclopropyl-5-nitropyridine-2,3-diamine 1.33 g (yield: 78%) of the title compound was obtained in the same manner as in Step 17-2 of Example 17 above, except that N-cyclopropyl-3,5-dinitropyridine-2-amine obtained in Step 51-1 was used instead of N-methyl-2,4-dinitroaniline, and a mixed solution of methanol and water in a ratio of 1:1 was used as a solvent.

$^1$H NMR (400 MHz, DMSO-$d_6$) δ 8.41 (d, J=2.5 Hz, 1H), 7.34 (d, J=2.5 Hz, 1H), 7.12 (d, J=3.6 Hz, 1H), 5.35 (s, 2H), 2.93 (tq, J=7.3 Hz, 3.8 Hz, 1H), 0.84-0.71 (m, 2H), 0.57-0.45 (m, 2H).

Step 51-3: Preparation of 3-cyclopropyl-6-nitro-1H-imidazo[4,5-b]pyridin-2(3H)-one 1.16 g (yield: 77%) of the title compound was obtained in the same manner as in Step 9-1 of Example 9 above, except that $N^2$-cyclopropyl-5-nitropyridine-2,3-diamine obtained in Step 51-2 was used instead of 4-fluoro-5-nitrobenzene-1,2-diamine.

$^1$H NMR (400 MHz, DMSO-$d_6$) δ 11.56 (s, 1H), 8.91 (d, J=2.4 Hz, 1H), 7.88 (d, J=2.4 Hz, 1H), 3.07-2.92 (m, 1H), 1.17-0.78 (m, 4H).

Step 51-4: Preparation of 3-cyclopropyl-1-methyl-6-nitro-1H-imidazo[4,5-b]pyridin-2(3H)-one 172.0 mg (yield: 80%) of the title compound was obtained in the same manner as in Step 35-1 of Example 35 above, except that 3-cyclopropyl-6-nitro-1H-imidazo[4,5-b]pyridin-2(3H)-one obtained in Step 51-3 was used instead of 1-methyl-5-nitro-1H-benzo[d]imidazol-2(3H)-one, and methyl iodide was used instead of ethyl iodide.

$^1$H NMR (400 MHz, DMSO-$d_6$) δ 8.95 (d, J=2.3 Hz, 1H), 8.31 (d, J=2.3 Hz, 1H), 3.40 (s, 3H), 3.08-2.97 (m, 1H), 1.11-0.99 (m, 4H).

Step 51-5: Preparation of 6-amino-3-cyclopropyl-1-methyl-1H-imidazo[4,5-b]pyridin-2(3H)-one 89.3 mg (yield: 78%) of the title compound was obtained in the same manner as in Step 1-2 of Example 1 above, except that 3-cyclopropyl-1-methyl-6-nitro-1H-imidazo[4,5-b]pyridin-2(3H)-one obtained in Step 51-4 was used instead of 7-nitroisoquinolin-1(2H)-one, and methanol was used as a solvent instead of dioxane.

$^1$H NMR (400 MHz, DMSO-$d_6$) δ 7.37 (d, J=2.3 Hz, 1H), 6.69 (d, J=2.3 Hz, 1H), 4.92 (s, 2H), 3.20 (s, 3H), 2.86 (tt, J=7.2 Hz, 3.5 Hz, 1H), 1.04-0.85 (m, 4H).

Step 51-6: Preparation of (3-cyclopropyl-1-methyl-2-oxo-2,3-dihydro-1H-benzo[d]imidazol-5-yl)carbonohydrazonoyl dicyanide 25.6 mg (yield: 20%) of the title compound was obtained in the same manner as in Step 1-3 of Example 1 above, except that 6-amino-3-cyclopropyl-1-methyl-1H-imidazo[4,5-b]pyridin-2(3H)-one obtained in Step 51-5 was used instead of 7-aminoisoquinolin-1(2H)-one.

$^1$H NMR (400 MHz, DMSO-$d_6$) δ 8.15 (d, J=2.2 Hz, 1H), 7.52 (d, J=2.2 Hz, 1H), 3.32 (s, 3H), 2.94 (td, J=6.8 Hz, 3.6 Hz, 1H), 0.99 (d, J=7.5 Hz, 4H).

EXAMPLE 52: PREPARATION OF (3-CYCLOPROPYL-1-ETHYL-2-OXO-2,3-DIHYDRO-1H-IMIDAZO[4,5-B]PYRIDIN-6-YL)CARBONOHYDRAZONOYL DICYANIDE (COMPOUND 52)

Step 52-1: Preparation of 3-cyclopropyl-1-ethyl-6-nitro-1H-imidazo[4,5-b]pyridin-2(3H)-one 179.5 mg (yield: 79%) of the title compound was obtained in the same manner as in Step 35-1 of Example 35 above, except that 3-cyclopropyl-6-nitro-1H-imidazo[4,5-b]pyridin-2(3H)-one obtained in Step 51-3 was used instead of 1-methyl-5-nitro-1H-benzo[d]imidazol-2(3H)-one.

$^1$H NMR (400 MHz, DMSO-$d_6$) δ Chloroform-d) δ 9.03 (d, J=2.3 Hz, 1H), 7.92 (d, J=2.2 Hz, 1H), 3.98 (q, J=7.3 Hz, 2H), 3.07 (tt, J=6.6 Hz, 4.1 Hz, 1H), 1.38 (t, J=7.3 Hz, 3H), 1.29-1.09 (m, 4H).

Step 52-2: Preparation of 6-amino-3-cyclopropyl-1-ethyl-1H-imidazo[4,5-b]pyridin-2(3H)-one 112.0 mg (yield: 71%) of the title compound was obtained in the same manner as in Step 1-2 of Example 1 above, except that 3-cyclopropyl-1-ethyl-6-nitro-1H-imidazo[4,5-b]pyridin-2(3H)-one obtained in Step 52-1 was used instead of 7-nitroisoquinolin-1(2H)-one, and methanol was used as a solvent instead of dioxane.

$^1$H NMR (400 MHz, Chloroform-d) δ 7.58 (d, J=2.3 Hz, 1H), 6.62 (d, J=2.3 Hz, 1H), 3.84 (q, J=7.3 Hz, 2H), 3.52 (s, 2H), 2.93 (tt, J=6.4 Hz, 4.1 Hz, 1H), 1.30 (t, J=7.2 Hz, 3H), 1.10 (dddt, J=7.0 Hz, 4.5 Hz, 2.8 Hz, 1.2 Hz, 4H).

Step 52-3: Preparation of (3-cyclopropyl-1-ethyl-2-oxo-2,3-dihydro-1H-benzo[d]imidazol-5-yl)carbonohydrazonoyl dicyanide 66.2 mg (yield: 44%) of the title compound was obtained in the same manner as in Step 1-3 of Example 1 above, except that 6-amino-3-cyclopropyl-1-ethyl-1H-imidazo[4,5-b]pyridin-2(3H)-one obtained in Step 52-2 was used instead of 7-aminoisoquinolin-1(2H)-one.

$^1$H NMR (400 MHz, DMSO-$d_6$) δ 13.11 (s, 1H), 8.16 (d, J=2.2 Hz, 1H), 7.58 (d, J=2.2 Hz, 1H), 3.88 (q, J=7.1 Hz, 2H), 2.95 (td, J=7.0 Hz, 3.6 Hz, 1H), 1.19 (t, J=7.1 Hz, 3H), 1.00 (ddt, J=9.9 Hz, 5.2 Hz, 2.7 Hz, 4H).

EXAMPLE 53: PREPARATION OF (3-CYCLOPROPYL-1-ISOPROPYL-2-OXO-2,3-DIHYDRO-1H-IMIDAZO[4,5-B]PYRIDIN-6-YL)CARBONOHYDRAZONOYL DICYANIDE (COMPOUND 53)

Step 53-1: Preparation of 3-cyclopropyl-1-isopropyl-6-nitro-1H-imidazo[4,5-b]pyridin-2(3H)-one 187.7 mg (yield: 76%) of the title compound was obtained in the same manner as in Step 35-1 of Example 35 above, except that 3-cyclopropyl-6-nitro-1H-imidazo[4,5-b]pyridin-2(3H)-one obtained in Step 51-3 was used instead of 1-methyl-5-nitro-1H-benzo[d]imidazol-2(3H)-one, and isopropyl iodide was used instead of ethyl iodide.

$^1$H NMR (400 MHz, DMSO-$d_6$) δ Chloroform-d) δ 9.02 (d, J=2.2 Hz, 1H), 8.02 (d, J=2.3 Hz, 1H), 4.74 (hept, J=7.0 Hz, 1H), 3.06 (tt, J=6.7 Hz, 4.1 Hz, 1H), 1.56 (d, J=7.1 Hz, 6H), 1.24-1.12 (m, 4H).

Step 53-2: Preparation of 6-amino-3-cyclopropyl-1-Isopropyl-1H-imidazo[4,5-b]pyridin-2(3H-one 130.9 mg (yield: 79%) of the title compound was obtained in the same manner as in Step 1-2 of Example 1 above, except that 3-cyclopropyl-1-isopropyl-6-nitro-1H-imidazo[4,5-b]pyridin-2(3H)-one obtained in Step 53-1 was used instead of 7-nitroisoquinolin-1(2H)-one, and methanol was used as a solvent instead of dioxane.

$^1$H NMR (400 MHz, Chloroform-d) δ 7.58 (d, J=2.3 Hz, 1H), 6.75 (d, J=2.3 Hz, 1H), 4.69 (hept, J=7.0 Hz, 1H), 3.50 (s, 2H), 2.92 (tt, J=6.5 Hz, 4.1 Hz, 1H), 1.47 (d, J=7.0 Hz, 6H), 1.10 (dddd, J=9.7 Hz, 4.2 Hz, 2.6 Hz, 1.2 Hz, 4H).

Step 53-3: Preparation of (3-cyclopropyl-1-isopropyl-2-oxo-2,3-dihydro-1H-benzo[d]imidazol-5-yl) carbonohydrazonoyl dicyanide 22.9 mg (yield: 34%) of the title compound was obtained in the same manner as in Step 1-3 of Example 1 above, except that 6-amino-3-cyclopropyl-1-isopropyl-1H-imidazo[4,5-b]pyridin-2(3H)-one obtained in Step 53-2 was used instead of 7-aminoisoquinolin-1(2H)-one, and water was used as a solvent.

$^1$H NMR (400 MHz, DMSO-$d_6$) δ 13.13 (s, 1H), 8.14 (d, J=2.1 Hz, 1H), 7.62 (d, J=2.2 Hz, 1H), 4.61 (hept, J=6.9 Hz, 1H), 3.03-2.79 (m, 1H), 1.42 (d, J=6.9 Hz, 6H), 1.08-0.91 (m, 4H).

EXAMPLE 64: PREPARATION OF (3-ISOPROPYL-1-METHYL-2-OXO-2,3-DIHYDRO-1H-IMIDAZO[4,5-B]PYRIDIN-6-YL)CARBONOHYDRAZONOYL DICYANIDE (COMPOUND 54)

Step 54-1: Preparation of N-Isopropyl-3,5-dinitropyridine-2-amine 2.07 g (yield: 93%) of the title compound was obtained in the same manner as in Step 17-1 of Example 17 above, except that 2-chloro-3,5-dinitropyridine was used instead of 1-chloro-2,4-dinitrobenzene, and isopropylamine was used instead of methylamine.

$^1$H NMR (400 MHz, Chloroform-d) δ 9.25 (d, J=2.6 Hz, 1H), 9.22 (d, J=2.5 Hz, 1H), 8.60 (s, 1H), 4.62 (dh, J=7.6 Hz, 6.6 Hz, 1H), 1.37 (d, J=6.5 Hz, 6H).

Step 54-2: Preparation of $N^2$-isopropyl-6-nitropyridine-2,3-diamine 1.07 g (yield: 59%) of the title compound was obtained in the same manner as in Step 17-2 of Example 17 above, except that N-isopropyl-3,5-dinitropyridine-2-amine obtained in Step 54-1 was used instead of N-methyl-2,4-dinitroaniline, and a mixed solution of methanol and water in a ratio of 1:1 was used as a solvent.

$^1$H NMR (400 MHz, DMSO-$d_6$) δ 8.37 (d, J=2.5 Hz, 1H), 7.32 (d, J=2.6 Hz, 1H), 6.74 (d, J=7.2 Hz, 1H), 5.41 (s, 2H), 4.39-4.26 (m, J=6.6 Hz, 1H), 1.21 (d, J=6.5 Hz, 6H).

Step 54-3: Preparation of 3-isopropyl-6-nitro-1H-imidazo[4,5-b]pyridin-2(3H)-one 1.08 g (yield: 91%) of the title compound was obtained in the same manner as in Step 9-1 of Example 9 above, except that $N^2$-isopropyl-5-nitropyridine-2,3-diamine obtained in Step 54-2 was used instead of 4-fluoro-5-nitrobenzene-1,2-diamine.

$^1$H NMR (400 MHz, DMSO-$d_6$) 8.91 (d, J=2.4 Hz, 1H), 7.91 (d, J=2.4 Hz, 1H), 4.69 (hept, J=6.9 Hz, 1H), 1.51 (d, J=6.9 Hz, 6H).

Step 54-4: Preparation of 3-isopropyl-1-methyl-6-nitro-1H-imidazo[4,5-b]pyridin-2(3H)-one 143.5 mg (yield: 67%) of the title compound was obtained in the same manner as in Step 35-1 of Example 35 above, except that 3-isopropyl-6-nitro-1H-imidazo[4,5-b]pyridin-2(3H)-one obtained in Step 54-3 was used instead of 1-methyl-5-nitro-1H-benzo[d]imidazol-2(3H)-one, and methyl iodide was used instead of ethyl iodide.

$^1$H NMR (400 MHz, Chloroform-d) δ 9.01 (d, J=2.3 Hz, 1H), 7.92 (d, J=2.3 Hz, 1H), 4.88 (hept, J=6.9 Hz, 1H), 3.48 (s, 3H), 1.61 (d, J=6.9 Hz, 6H).

Step 54-5: Preparation of 6-amino-3-isopropyl-1-methyl-1H-imidazo[4,5-b]pyridin-2(3H)-one 97.2 mg (yield: 78%) of the title compound was obtained in the same manner as in Step 1-2 of Example 1 above, except that 3-isopropyl-1-methyl-6-nitro-1H-imidazo[4,5-b]pyridin-2(3H)-one obtained in Step 54-4 was used instead of 7-nitroisoquinolin-1(2H)-one, and methanol was used as a solvent instead of dioxane.

$^1$H NMR (400 MHz, DMSO-$d_6$) δ 7.37 (d, J=2.3 Hz, 1H), 6.71 (d, J=2.2 Hz, 1H), 4.90 (s, 2H), 4.55 (hept, J=6.9 Hz, 1H), 3.22 (s, 3H), 1.44 (d, J=6.9 Hz, 6H).

Step 54-6: Preparation of (3-isopropyl-1-methyl-2-oxo-2,3-dihydro-1H-benzo[d]imidazol-5-yl)carbonohydrazonoyl dicyanide 103.5 mg (yield: 77%) of the title compound was obtained in the same manner as in Step 1-3 of Example 1 above, except that 6-amino-3-isopropyl-1-methyl-1H-imidazo[4,5-b]pyridin-2(3H)-one obtained in Step 54-5 was used instead of 7-aminoisoquinolin-1(2H)-one.

$^1$H NMR (400 MHz, DMSO-$d_6$) δ 13.18 (s, 1H), 8.16 (d, J=2.2 Hz, 1H), 7.56 (d, J=2.2 Hz, 1H), 4.66 (hept, J=6.9 Hz, 1H), 3.35 (s, 3H), 1.49 (d, J=6.9 Hz, 6H).

EXAMPLE 55: PREPARATION OF (1-ETHYL-3-ISOPROPYL-2-OXO-2,3-DIHYDRO-1H-IMIDAZO[4,5-B]PYRIDIN-6-YL)CARBONOHYDRAZONOYL DICYANIDE (COMPOUND 55)

Step 55-1: Preparation of 1-ethyl-3-isopropyl-6-nitro-1H-imidazo[4,5-b]pyridin-2(3H)-one 194.1 mg (yield: 86%) of the title compound was obtained in the same manner as in Step 35-1 of Example 35 above, except that 3-isopropyl-6-nitro-1H-imidazo[4,5-b]pyridin-2(3H)-one obtained in Step 54-3 was used instead of 1-methyl-5-nitro-1H-benzo[d]imidazol-2(3H)-one.

$^1$H NMR (400 MHz, Chloroform-d) 69.00 (d, J=2.3 Hz, 1H), 7.92 (d, J=2.3 Hz, 1H), 4.87 (hept, J=6.9 Hz, 1H), 3.98 (q, J=7.2 Hz, 2H), 1.61 (d, J=6.9 Hz, 6H), 1.39 (t, J=7.3 Hz, 3H).

Step 55-2: Preparation of 6-amino-1-ethyl-3-isopropyl-1H-imidazo[4,5-b]pyridin-2(3H)-one 27.4 mg (yield: 16%) of the title compound was obtained in the same manner as in Step 1-2 of Example 1 above, except that 1-ethyl-3-isopropyl-6-nitro-1H-imidazo[4,5-b]

pyridin-2(3H)-one obtained in Step 55-1 was used instead of 7-nitroisoquinolin-1(2H)-one, and methanol was used as a solvent instead of dioxane.

$^1$H NMR (400 MHz, DMSO-$d_6$) δ 7.37 (d, J=2.2 Hz, 1H), 6.77 (d, J=2.3 Hz, 1H), 4.88 (s, 2H), 4.55 (hept, J=6.9 Hz, 1H), 3.75 (q, J=7.2 Hz, 2H), 1.44 (d, J=6.9 Hz, 6H), 1.17 (t, J=7.2 Hz, 3H).

Step 55-3: Preparation of (1-ethyl-3-isopropyl-2-oxo-2,3-dihydro-1H-benzo[d]imidazol-5-yl)carbonohydrazonoyl dicyanide 5.7 mg (yield: 15%) of the title compound was obtained in the same manner as in Step 1-3 of Example 1 above, except that 6-amino-1-ethyl-3-isopropyl-1H-imidazo[4,5-b]pyridin-2(3H)-one obtained in Step 55-2 was used instead of 7-aminoisoquinolin-1(2H)-one.

$^1$H NMR (400 MHz, DMSO-$d_6$) δ 13.17 (s, 1H), 8.16 (d, J=2.2 Hz, 1H), 7.61 (d, J=2.2 Hz, 1H), 4.65 (h, J=7.0 Hz, 1H), 3.90 (q, J=7.2 Hz, 2H), 1.49 (d, J=6.9 Hz, 6H), 1.21 (t, J=7.0 Hz, 3H).

EXAMPLE 56: PREPARATION OF (1,3-DIMETHYL-2-OXO-2,3-DIHYDRO-1H-BENZO[D]IMIDAZOL-5-YL)METHYL)CARBONOHYDRAZONOYL DICYANIDE (COMPOUND 56)

(1,3-Dimethyl-2-oxo-2,3-dihydro-1H-benzo[d]imidazol-5-yl)carbonohydrazonoyl dicyanide (100 mg, 0.39 mmol) prepared in Example 22 was dissolved in dimethylformamide under a nitrogen atmosphere and potassium tert-butoxide (66 mg, 0.59 mmol) was added thereto at room temperature, and then methane iodide (122 μL, 1.97 mmol) was added thereto. The reaction mixture was stirred at 60° C. for 4 hours. Upon completion of the reaction, a reaction product was extracted using distilled water and ethyl acetate to obtain an organic layer, and the organic layer was dried with anhydrous magnesium sulfate and filtered. The filtrate was concentrated under reduced pressure, and the crude material was purified by column chromatography to obtain 41 mg (yield: 38%) of the title compound.

$^1$H NMR (400 MHz, DMSO-$d_6$) δ 7.48-7.15 (m, 3H), 4.10-3.84 (m, 3H), 3.35 (s, 6H).

EXAMPLE 57: PREPARATION OF ACETYL(1,3-DIMETHYL-2-OXO-2,3-DIHYDRO-1H-BENZO[D]IMIDAZOL-5-YL)CARBONOHYDRAZONOYL DICYANIDE (COMPOUND 57)

(1,3-Dimethyl-2-oxo-2,3-dihydro-1H-benzo[d]imidazol-5-yl)carbonohydrazonoyl dicyanide (150 mg, 0.59 mmol) prepared in Example 22 and KOH (36 mg, 0.65 mmol) were dissolved in methanol, and the solution was stirred at room temperature for 3 hours. Upon completion of the reaction, the solvent was removed under reduced pressure and solidified with ether. After a produced solid (170 mg, 0.58 mmol) and triethylamine (40 μL, 0.29 mmol) were dissolved in acetonitrile, acetyl chloride (103 μL, 1.45 mmol) was added thereto, and the reaction mixture was stirred at room temperature for 4 hours. Upon completion of the reaction, a reaction product was extracted using distilled water and ethyl acetate to obtain an organic layer, and the organic layer was dried with anhydrous magnesium sulfate and filtered. The filtrate was concentrated under reduced pressure and solidified with ether and then filtered. The filtrate was re-concentrated under reduced pressure and solidified with hexane to obtain 43 mg (yield: 25%) of the title compound.

$^1$H NMR (400 MHz, Chloroform-d) δ 7.07 (d, J=8.5 Hz, 1H), 6.91 (dd, J=8.2 Hz, 1.7 Hz, 1H), 6.77 (s, 1H), 3.46 (s, 3H), 3.42 (s, 3H), 2.61 (s, 3H).

PREPARATION EXAMPLES

Meanwhile, the novel compound represented by Formula 1 according to the present invention may be formulated in various forms. The following examples exemplarily describe several methods of preparing formulations including the compound represented by Formula 1 according to the present invention as an active ingredient, and the present invention is not limited thereto.

Preparation Example 1: Preparation of Tablet by Direct Pressing 5.0 mg of each of the active ingredients prepared in Examples 1 to 57 was sieved, mixed with 14.1 mg of lactose, 0.8 mg of crospovidone USNF, and 0.1 mg of magnesium stearate, and then pressed into tablets.

Preparation Example 2: Preparation of Tablet by Wet Granulation 5.0 mg of each of the active ingredients prepared in Examples 1 to 57 was sieved and mixed with 16.0 mg of lactose and 4.0 mg of starch. 0.3 mg of polysorbate 80 was dissolved in pure water, and this solution was added to the mixture in a suitable amount, followed by atomizing to obtain fine particles. After drying, the fine particles were sieved, mixed with 2.7 mg of colloidal silicon dioxide and 2.0 mg of magnesium stearate, and pressed into tablets.

Preparation Example 3: Preparation of Powder and Capsule 5.0 mg of each of the active ingredients prepared in Examples 1 to 57 was sieved and then mixed with 14.8 mg of lactose, 10.0 mg of polyvinylpyrrolidone, and 0.2 mg of magnesium stearate. The mixture was filled into hard No. 5 gelatin capsules using a suitable apparatus to prepare capsules.

Preparation Example 4: Preparation of Injection Drug 100 mg of each of the active ingredients prepared in Examples 1 to 57 was mixed with 180 mg of mannitol, 26 mg of $Na_2HPO_4 \cdot 12H_2O$, and 2974 mg of distilled water to prepare injection drugs.

Experimental Example 1: Selection of Tau Protein Aggregation-Inhibiting Substance Using Cell Model In order to select novel tau protein aggregation-inhibiting substances, tau-BiFC cell model, in which formation of tau oligomers in living cells is easily observed, was used. Tau-BiFC cells were aliquoted into a 384-well plate. On the next day, the cells were treated with each of the compounds prepared according to Examples 1 to 57 at concentrations of 1 μM, 3 μM, and 10 μM, together with Forskolin (at a treatment concentration of 30 μM), which is a compound inducing tau protein aggregation by activating tau phosphorylase PKA. After 48 hours, nuclei in the cells were stained using Hoechst (at a treatment concentration of 2 μg/mL), and BiFC fluorescence intensity was automatically measured using Operetta (PerkinElmer) to count stained nuclei in each well out of the entire well plate. The group treated only with Forskolin, which induces tau protein aggregation, was set to a reference point of a 100% tau protein-aggregated state, and the effects of the compounds were confirmed using the equation "BiFC fluorescence intensity due to compound synthesized according to embodiment of present invention/(fluorescence intensity of control group treated only with Forskolin inducing tau protein aggregation−fluorescence intensity of untreated control group)×100". Furthermore, the degree of cytotoxicity induced by the newly synthesized compound was also measured based on the 100% cell viability of the group treated only with Forskolin as a reference, and the cytotoxicity value of each compound was calculated using the equation "(number of stained nuclei in group treated with compound/number of stained nuclei in group treated with Forskolin)×100". Based on the treatment results, substances inhibiting intracellular tau protein aggregation were selected from a series of candidate groups showing a tau protein aggregation inhibition rate of 70% or more and cell viability of 100% at a compound treatment concentration of 10 μM or more.

Experimental Example 2: Confirmation of Concentration-Dependent Inhibitory Effect of Novel Compound on Tau Protein Aggregation In order to evaluate dose-dependent tau protein aggregation inhibition effects of the compounds selected according to Experimental Example 1 on tau protein aggregation, tau-BiFC cells were treated with the selected compounds at concentrations of 0.03 μM, 0.01 μM, 0.3 μM, 1 μM, 3 μM, 10 μM, and 30 μM, respectively, together with Forskolin (at a treatment concentration of 30 μM), which is a tau protein aggregation-inducing substance. After 48 hours, tau protein aggregation reaction and degrees of cytotoxicity were analyzed by observing images of the cells. $IC_{50}$ and toxicity of the compounds were analyzed by way of nonlinear regression analysis of prism software (Graph Pad). Calculated results of representative compounds are shown in Table 2 below.

TABLE 2

| | Tau BiFC in cells | | |
|---|---|---|---|
| Compound # | $IC_{50}$ (μM) | Response (% @10 μM) | Cell viability (% @10 μM) |
| 1 | 0.13 | 0 | 152.9 |
| 2 | N.D. | 0 | 57.5 |
| 3 | 0.2 | 0 | 112 |
| 4 | 1.8 | 0 | 99.3 |
| 5 | N.D. | 0 | 41.4 |
| 6 | 0.7 | 0 | 118.1 |
| 7 | 0.2 | 0 | 101.9 |
| 8 | 0.43 | 0 | 152.5 |
| 9 | 0.17 | 0 | 155.3 |
| 10 | 0.3 | 0 | 145.3 |
| 11 | 0.1 | 0 | 142.3 |
| 12 | 0.87 | 0 | 145.2 |
| 13 | 0.2 | 0.8 | 115.8 |
| 14 | 0.06 | 0 | 129.1 |
| 15 | 8.4 | 5.5 | 127.7 |
| 16 | 0.6 | 0 | 129.8 |
| 17 | 1.2 | 0 | 94.38 |
| 18 | 0.04 | 0 | 110.7 |
| 19 | 0.1 | 0 | 125.3 |
| 20 | 0.1 | 0 | 106 |
| 21 | 0.6 | 0 | 135 |

TABLE 2-continued

| | Tau BiFC in cells | | |
|---|---|---|---|
| Compound # | $IC_{50}$ (μM) | Response (% @10 μM) | Cell viability (% @10 μM) |
| 22 | 0.2 | 0 | 120.7 |
| 23 | 0.1 | 0 | 117 |
| 24 | 0.2 | 0 | 125.1 |
| 25 | 0.02 | −16 | 118 |
| 26 | 0.77 | −5 | 120 |
| 27 | 0.01 | −41 | 115 |
| 28 | — | 13 | 134 |
| 29 | 0.07 | −31 | 133 |
| 30 | — | 36 | 127 |
| 31 | — | 47 | 119 |
| 32 | — | 38 | 132 |
| 33 | 0.005 | −43 | 114 |
| 34 | 0.05 | −45 | 120 |
| 35 | 0.01 | −44 | 130 |
| 36 | 0.02 | −57 | 104 |
| 37 | 0.2 | −49 | 121 |
| 38 | 0.03 | −31 | 106 |
| 39 | 0.01 | −45 | 106 |
| 40 | 0.03 | −38 | 122 |
| 41 | 0.02 | −54 | 112 |
| 42 | 0.08 | −52 | 124 |
| 43 | 0.01 | −49 | 96 |
| 44 | — | 10 | 138 |
| 45 | 0.2 | −24 | 113 |
| 46 | — | 23 | 131 |
| 47 | — | 13 | 117 |
| 48 | 0.06 | −18 | 143 |
| 49 | 0.05 | −34 | 139 |
| 50 | — | 2 | 119 |
| 51 | 0.66 | −11 | 137 |
| 52 | 0.20 | −30 | 133 |
| 53 | 0.16 | −39 | 125 |
| 54 | 0.30 | −38 | 118 |
| 55 | 0.11 | −32 | 124 |

N.D.: Not Determined

Experimental Example 3: Inhibitory Effect of Novel Compound on CYP Coenzyme Activity The inhibitory effects of the compounds prepared according to Examples 1 to 57 on CYP coenzyme activity were identified. Specifically, human liver microsomes (0.25 mg/mL), a 0.1 M phosphate buffer solution (pH 7.4), a substrate drug cocktail of five types of drug metabolism enzymes (50 μM phenacetin, 10 μM diclofenac, 100 μM S-mephenytoin, 5 μM dextromethorphan, and 2.5 μM midazolam), and the compound at a concentration of 0 μM or 10 μM were mixed and pre-cultured at 37° C. for 5 minutes, and then further cultured at 37° C. for 15 minutes together with an NADPH generation system solution added thereto. Thereafter, the reaction was terminated by adding an acetonitrile solution containing an internal standard material (terfenadine) and centrifuged for 5 minutes (14,000 rpm, 4° C.), and then a supernatant was injected into an LC-MS/MS system for simultaneous analysis of metabolites of the substrate drugs to thereby evaluate the inhibitory effects on drug metabolism.

Metabolites of each CYP coenzyme indicator drug generated through the reaction were analyzed using the Shimadzu Nexera XR system and TSQ Vantage (Thermo). In an HPLC column, Kinetex C18 (2.1 mm×100 mm, 2.6 μm, particle size; Phenomenex, USA) was used, and mobile phases were (A) distilled water containing 0.1% formic acid and (B) acetonitrile containing 0.1% formic acid, and a gradient program shown in Table 3 was applied thereto.

TABLE 3

| Time (min) | Flow rate (mL/min) | % A | % B |
|---|---|---|---|
| 0 | 0.3 | 100 | 0 |
| 1.0 | 0.3 | 60 | 40 |
| 4.0 | 0.3 | 50 | 50 |
| 4.1 | 0.3 | 100 | 0 |
| 7.0 | 0.3 | 100 | 0 |

The generated metabolites were quantified using a multiple reaction monitoring (MRM) quantification mode, and Xcalibur (version 1.6.1) was used for data analysis. In order to express inhibitory effects of the novel compound prepared according to the examples of the present invention on CYP coenzyme activity, CYP coenzyme activities (%) with respect to the control group not treated with the compound are shown in Table 4 below.

TABLE 4

| Compound # | CYP1A2 | CYP2C9 | CYP2C19 | CYP2D6 | CYP3A4 |
|---|---|---|---|---|---|
| 2 | 43.5 | 77.9 | 79.2 | 94.3 | 89 |
| 3 | 50.2 | 78.5 | 98.2 | >100 | >100 |
| 4 | 85.3 | 59.3 | 89.7 | 91.1 | 81.6 |
| 5 | 70.7 | 29.1 | >100 | 93.1 | 88.6 |
| 6 | 68.3 | 8.7 | 37.8 | 85.4 | 81.4 |
| 7 | 33.2 | 29.8 | 65.1 | 86.2 | 72 |
| 10 | 94.2 | >100 | 94.6 | >100 | >100 |
| 11 | 73.7 | 45.8 | 88.4 | >100 | >100 |
| 12 | 99.6 | 93.4 | 92.2 | >100 | >100 |
| 13 | 79 | 23.3 | 55.2 | 99.4 | 92.7 |
| 14 | 81.6 | 19.5 | 68.8 | 85.6 | 91.2 |
| 15 | 87.3 | 59.4 | 90.3 | >100 | 98.3 |
| 16 | 91.5 | 54.9 | 90.8 | >100 | 99.8 |
| 17 | 32.1 | 81.2 | 80.4 | 87.1 | 89 |
| 18 | 81.4 | 7.5 | 63.2 | 88.1 | 78.3 |
| 19 | 52.5 | 23.3 | 75.7 | 40.5 | 81.8 |
| 20 | 87.3 | 32.3 | 85.7 | 98.1 | 98.8 |
| 21 | 79.6 | 64.4 | 83.7 | 89.1 | 90.4 |
| 22 | 93.5 | 99 | >100 | >100 | >100 |
| 23 | 83.2 | 46.4 | 69.7 | 95.3 | 79.6 |
| 24 | 32.8 | 40.6 | 73.9 | 82.5 | 78.1 |
| 27 | 58.7 | 33.6 | 96.3 | 86.7 | 73.6 |
| 29 | 97.3 | 4.7 | 91.3 | 94.2 | >100 |
| 33 | 37.8 | 69.9 | >100 | >100 | 97.6 |
| 34 | >100 | 41.9 | 88.8 | 99.1 | 90.2 |
| 35 | 93.1 | 72.5 | 100 | >100 | >100 |
| 36 | 93.7 | 36.6 | 89.5 | >100 | 95.8 |
| 37 | 64.6 | 29.2 | 90.7 | >100 | 96.7 |
| 38 | 98.9 | 92.6 | >100 | >100 | >100 |
| 42 | 91.9 | 59.6 | >100 | >100 | 93.5 |
| 43 | 61.7 | 14.1 | 60.2 | 82.2 | 72.6 |
| 48 | >100 | >100 | >100 | >100 | >100 |
| 53 | >100 | 75.3 | >100 | >100 | 97.8 |
| 55 | 58.4 | 38.9 | 73.1 | 85.8 | 78 |

Experimental Example 4: Identification of Stability of Liver Microsome Due to Novel Compound The stability of liver microsomes due to the compounds prepared according to Examples 1 to 57 was confirmed. Specifically, four types of liver microsomes (human, dog, rat, and mouse, each 0.25 mg/mL), a 0.1 M phosphate buffer solution (pH 7.4), and each of the compounds at a concentration of 1 μM were mixed and pre-cultured at 37° C. for 5 minutes and further cultured at 37° C. for 30 minutes together with an NADPH generation system solution added thereto. Thereafter, the reaction was terminated by adding an acetonitrile solution containing an internal standard material (chloropropamide) and centrifuged for 5 minutes (14,000 rpm, 4° C.), and then a supernatant was injected into an LC-MS/MS system for analysis of substrate drugs to thereby evaluate metabolic stability due to 8 types of compounds.

The amount of the substrate remaining after the reaction was analyzed using the Shimadzu Nexera XR system and TSQ Vantage (Thermo). In an HPLC column, Kinetex XB-C18 (2.1 mm×100 mm, particle size of 2.6 μm; Phenomenex, USA) was used, and mobile phases were (A) distilled water containing 0.1% formic acid and (B) acetonitrile containing 0.1% formic acid. Analyst software (version 1.6.3) and Xcalibur (version 1.6.1) were used for data analysis. The calculated results are shown in Table 5 below.

TABLE 5

| Compound # | Human (%) | Dog (%) | Rat (%) | Mouse (%) |
|---|---|---|---|---|
| 2 | 27 | 2.5 | 88 | 63.4 |
| 3 | 57.4 | 6.4 | 44.4 | 10.1 |
| 4 | >100 | >100 | 94.5 | >100 |
| 5 | 98.1 | >100 | >100 | 92.9 |
| 6 | 94.2 | 95 | >100 | 87 |
| 7 | 96 | 95.7 | 89.7 | 93.3 |
| 10 | >100 | 98.1 | 92.7 | 92.6 |
| 11 | 96.1 | 63.1 | 82.8 | 63.9 |
| 12 | >100 | >100 | 94.9 | >100 |
| 13 | >100 | >100 | >100 | >100 |
| 14 | 98.3 | 73.3 | 87.1 | 59.6 |
| 15 | 74.2 | 97.1 | 92.5 | >100 |
| 16 | 98.9 | 95.7 | 89.1 | 81 |
| 17 | >100 | >100 | >100 | 95.7 |
| 18 | 85.1 | 93.8 | 70.8 | 71.3 |
| 19 | 99.7 | 80.4 | 69.7 | 58.7 |
| 20 | 98.1 | 95.6 | 73.3 | 73.1 |
| 21 | 73.9 | 72.1 | 79.8 | 71.8 |
| 22 | 80.6 | 92.2 | 91.6 | 63.1 |
| 23 | 83.1 | 86.1 | 77.7 | 72.4 |
| 24 | 88.2 | 88.1 | 86.8 | 84.1 |
| 29 | >100 | — | 96.4 | 88.9 |
| 33 | 93.2 | — | 85.5 | 78.7 |
| 34 | >100 | — | 57.5 | 86.6 |
| 35 | 98.7 | — | 86 | 87.1 |
| 36 | >100 | — | 86.4 | 89.4 |
| 37 | 84.9 | — | 58.5 | 75.7 |
| 38 | 95 | — | 91.8 | 81.6 |
| 42 | 81.7 | — | 78.7 | 63.4 |
| 43 | 81.5 | — | 86.2 | 58.6 |
| 48 | 96.7 | — | 96.3 | >100 |
| 53 | 84.6 | — | 82.1 | 83.5 |
| 55 | 85.5 | — | 91.8 | 87.7 |

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. The various embodiments disclosed herein are not intended to be limiting, with the true scope and spirit being indicated by the following claims. The present invention is to be limited only by the terms of the appended claims, along with the full scope of equivalents to which such claims are entitled.

The invention claimed is:

1. A compound represented by Formula 1 below or a pharmaceutically acceptable salt thereof:

[Formula 1]

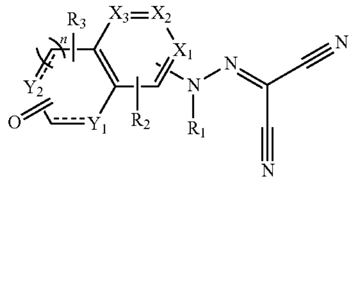

wherein, in Formula 1, $X_1$ to $X_3$ are each independently N or C(H);

$Y_1$ and $Y_2$ are each independently N($R_4$), C(H), O, or S, and at least one of $Y_1$ and $Y_2$ is N($R_4$);

n is 0 or 1;

┄┄ is ═══ or ─── forming an aromatic or non-aromatic fused-heterocyclic ring;

$R_1$ is hydrogen, $C_{1-6}$ alkyl, or $C_{1-6}$ alkylcarbonyl;

$R_2$ and $R_3$ are each independently hydrogen, $C_{1-6}$ alkyl, halogen, cyano, $C_{1-6}$ haloalkyl, $C_{1-6}$ alkoxy, $C_{1-6}$ haloalkoxy, $C_{1-6}$ alkylamino, di($C_{1-6}$ alkyl)amino, $C_{1-6}$ alkylaminocarbonyl, or di($C_{1-6}$ alkyl)aminocarbonyl; and $R_4$ is hydrogen, $C_{1-6}$ alkyl, $C_{1-6}$ alkoxy, $C_{1-6}$ alkoxy-$C_{0-6}$ alkyl, $C_{1-6}$ haloalkyl, $C_{3-6}$ cycloalkyl-$C_{0-6}$ alkyl, 5- or 6-membered heterocycle-$C_{0-6}$ alkyl, $C_{6-10}$ aryl, or 5- to 10-membered heteroaryl, wherein the 5- or 6-membered heterocycle, $C_{6-10}$ aryl, and 5- to 10-membered heteroaryl are unsubstituted or substituted with $C_{1-6}$ alkoxy or $C_{1-6}$ alkoxycarbonyl, with the exception if $Y_1$ and $Y_2$ are $NR_4$, $R_1$ to $R_4$ are H, $X_1$ to $X_3$ are CH, and n=0.

2. The compound or pharmaceutically acceptable salt thereof of claim 1, wherein $R_1$ is hydrogen, $C_{1-6}$ alkyl, or $C_{1-6}$ alkylcarbonyl;

$R_2$ is hydrogen, halogen, $C_{1-6}$ alkyl, or $C_{1-6}$ alkoxy;

$R_3$ is hydrogen or $C_{1-6}$ alkyl; and $R_4$ is hydrogen, $C_{1-6}$ alkyl, $C_{1-6}$ haloalkyl, $C_{3-6}$ cycloalkyl-$C_{0-6}$ alkyl, or $C_{6-10}$ aryl.

3. The compound or pharmaceutically acceptable salt thereof of claim 1, wherein $R_1$ is hydrogen, methyl, or acetyl;

$R_2$ is hydrogen, chloro, fluoro, methyl, or methoxy;

$R_3$ is hydrogen or methyl; and $R_4$ is hydrogen, methyl, ethyl, isopropyl, difluoromethyl, cyclopropyl, or phenyl.

4. The compound or pharmaceutically acceptable salt thereof of claim 1, wherein the compound is represented by Formula 2 below:

[Formula 2]

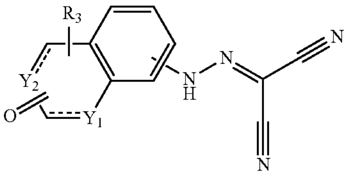

wherein, in Formula 2 above, one of $Y_1$ and $Y_2$ is CH, and the other is $NR_4$;

┄┄ in contact with CH is ═══ and ┄┄ in contact with $NR_4$ is ───;

$R_3$ is hydrogen or methyl; and $R_4$ is hydrogen, methyl, or isopropyl.

5. The compound or pharmaceutically acceptable salt thereof of claim 1, wherein the compound is represented by Formula 3 below:

[Formula 3]

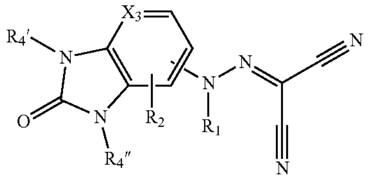

wherein, in Formula 3 above, $X_3$ is C(H) or N;

$R_1$ is hydrogen, methyl, or acetyl;

$R_2$ is hydrogen, chloro, fluoro, methyl, or methoxy; and $R_4$ and $R_{4''}$ are each independently hydrogen, methyl, ethyl, isopropyl, difluoromethyl, cyclopropyl, or phenyl.

6. The compound or pharmaceutically acceptable salt thereof of claim 1, wherein the compound is represented by Formula 4 below:

[Formula 4]

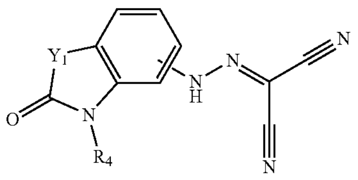

wherein, in Formula 4 above, $Y_1$ is S or O; and $R_4$ is hydrogen, methyl, isopropyl, or difluoromethyl.

7. The compound or pharmaceutically acceptable salt thereof of claim 1, wherein the compound is 1) (1-oxo-1,2-dihydroisoquinolin-7-yl)carbonohydrazonoyl dicyanide, 2) (2-methyl-1-oxo-1,2-dihydroisoquinolin-7-yl)carbonohydrazonoyl dicyanide, 3) (2-isopropyl-1-oxo-1,2-dihydroisoquinolin-7-yl)carbonohydrazonoyl dicyanide, 4) (1-oxo-1,2-dihydroisoquinolin-5-yl)carbonohydrazonoyl dicyanide, 5) (2-methyl-1-oxo-1,2-dihydroisoquinolin-5-yl)carbonohydrazonoyl dicyanide, 6) (2-isopropyl-1-oxo-1,2-dihydroisoquinolin-5-yl)carbonohydrazonoyl dicyanide, 7) (2,3-dimethyl-1-oxo-1,2-dihydroisoquinolin-5-yl)carbonohydrazonoyl dicyanide, 8) (2-oxo-1,2-dihydroquinolin-6-yl)carbonohydrazonoyl dicyanide, 9) (6-fluoro-1,3-dimethyl-2-oxo-2,3-dihydro-1H-benzo[d]imidazol-5-yl)carbonohydrazonoyl dicyanide, 10) (6-chloro-1,3-dimethyl-2-oxo-2,3-dihydro-1H-benzo[d]imidazol-5-yl)carbonohydrazonoyl dicyanide, 11) (7-chloro-1,3-dimethyl-2-oxo-2,3-dihydro-1H-benzo[d]imidazol-5-yl)carbonohydrazonoyl dicyanide, 12) (1,3-dimethyl-2-oxo-2,3-dihydro-1H-imidazo[4,5-b]pyridin-6-yl)carbonohydrazonoyl dicyanide, 13) (2-oxo-2,3-dihydrobenzo[d]thiazol-6-yl)carbonohydrazonoyl dicyanide, 14) (3-methyl-2-oxo-2,3-dihydrobenzo[d]thiazol-6-yl)carbonohydrazonoyl dicyanide, 15) (2-oxo-2,3-dihydrobenzo[d]oxazol-6-yl)carbonohydrazonoyl dicyanide, 16) (3-methyl-2-oxo-2,3-dihydrobenzo[d]oxazol-6-yl)carbonohydrazonoyl dicyanide,
17) (1-methyl-2-oxo-2,3-dihydro-1H-benzo[d]imidazol-5-yl)carbonohydrazonoyl dicyanide,
18) (3-isopropyl-2-oxo-2,3-dihydrobenzo[d]thiazol-6-yl)carbonohydrazonoyl dicyanide,
19) (3-(difluoromethyl)-2-oxo-2,3-dihydrobenzo[d]thiazol-6-yl)carbonohydrazonoyl dicyanide,
20) (3-isopropyl-2-oxo-2,3-dihydrobenzo[d]oxazol-6-yl)carbonohydrazonoyl dicyanide,
21) (3-(difluoromethyl)-2-oxo-2,3-dihydrobenzo[d]oxazol-6-yl)carbonohydrazonoyl dicyanide,
22) (1,3-dimethyl-2-oxo-2,3-dihydro-1H-benzo[d]imidazol-5-yl)carbonohydrazonoyl dicyanide,
23) (1,3-diisopropyl-2-oxo-2,3-dihydro-1H-benzo[d]imidazol-5-yl)carbonohydrazonoyl dicyanide,
24) (1,3-bis(difluoromethyl)-2-oxo-2,3-dihydro-1H-benzo[d]imidazol-5-yl)carbonohydrazonoyl dicyanide,
25) (1-methyl-2-oxo-1,2-dihydroquinolin-6-yl)carbonohydrazonoyl dicyanide,
26) (4-methyl-2-oxo-1,2-dihydroquinolin-6-yl)carbonohydrazonoyl dicyanide,
27) (1,4-dimethyl-2-oxo-1,2-dihydroquinolin-6-yl)carbonohydrazonoyl dicyanide,
28) (3-methyl-2-oxo-2,3-dihydrobenzo[d]oxazol-5-yl)carbonohydrazonoyl dicyanide,
29) (3-isopropyl-2-oxo-2,3-dihydrobenzo[d]oxazol-5-yl)carbonohydrazonoyl dicyanide,
30) (3-(difluoromethyl)-2-oxo-2,3-dihydrobenzo[d]oxazol-5-yl)carbonohydrazonoyl dicyanide,
31) (1,3,6-trimethyl-2-oxo-2,3-dihydro-1H-benzo[d]imidazol-5-yl)carbonohydrazonoyl dicyanide,
32) (6-methoxy-1,3-dimethyl-2-oxo-2,3-dihydro-1H-benzo[d]imidazol-5-yl)carbonohydrazonoyl dicyanide,
33) (7-methoxy-1,3-dimethyl-2-oxo-2,3-dihydro-1H-benzo[d]imidazol-5-yl)carbonohydrazonoyl dicyanide,
34) (1,3-diisopropyl-2-oxo-2,3-dihydro-1H-imidazo[4,5-b]pyridin-6-yl)carbonohydrazonoyl dicyanide,
35) (3-ethyl-1-methyl-2-oxo-2,3-dihydro-1H-benzo[d]imidazol-5-yl)carbonohydrazonoyl dicyanide,
36) (3-isopropyl-1-methyl-2-oxo-2,3-dihydro-1H-benzo[d]imidazol-5-yl)carbonohydrazonoyl dicyanide,
37) (3-(difluoromethyl)-1-methyl-2-oxo-2,3-dihydro-1H-benzo[d]imidazol-5-yl)carbonohydrazonoyl dicyanide,
38) (1-ethyl-3-methyl-2-oxo-2,3-dihydro-1H-benzo[d]imidazol-5-yl)carbonohydrazonoyl dicyanide,
39) (3-(difluoromethyl)-1-ethyl-2-oxo-2,3-dihydro-1H-benzo[d]imidazol-5-yl)carbonohydrazonoyl dicyanide,
40) (1-cyclopropyl-3-methyl-2-oxo-2,3-dihydro-1H-benzo[d]imidazol-5-yl)carbonohydrazonoyl dicyanide,
41) (1-cyclopropyl-3-ethyl-2-oxo-2,3-dihydro-1H-benzo[d]imidazol-5-yl)carbonohydrazonoyl dicyanide,
42) (1-cyclopropyl-3-isopropyl-2-oxo-2,3-dihydro-1H-benzo[d]imidazol-5-yl)carbonohydrazonoyl dicyanide,
43) (3-(difluoromethyl)-1-isopropyl-2-oxo-2,3-dihydro-1H-benzo[d]imidazol-5-yl)carbonohydrazonoyl dicyanide,
44) (1-ethyl-3-methyl-2-oxo-2,3-dihydro-1H-imidazo[4,5-b]pyridin-6-yl)carbonohydrazonoyl dicyanide,
45) (1-isopropyl-3-methyl-2-oxo-2,3-dihydro-1H-imidazo[4,5-b]pyridin-6-yl)carbonohydrazonoyl dicyanide,
46) (1-(difluoromethyl)-3-methyl-2-oxo-2,3-dihydro-1H-imidazo[4,5-b]pyridin-6-yl)carbonohydrazonoyl dicyanide,
47) (3-methyl-2-oxo-1-phenyl-2,3-dihydro-1H-imidazo[4,5-b]pyridin-6-yl)carbonohydrazonoyl dicyanide,
48) (3-ethyl-1-methyl-2-oxo-2,3-dihydro-1H-imidazo[4,5-b]pyridin-6-yl)carbonohydrazonoyl dicyanide,
49) (3-ethyl-1-isopropyl-2-oxo-2,3-dihydro-1H-imidazo[4,5-b]pyridin-6-yl)carbonohydrazonoyl dicyanide,
50) (1-(difluoromethyl)-3-ethyl-2-oxo-2,3-dihydro-1H-imidazo[4,5-b]pyridin-6-yl)carbonohydrazonoyl dicyanide,
51) (3-cyclopropyl-1-methyl-2-oxo-2,3-dihydro-1H-imidazo[4,5-b]pyridin-6-yl)carbonohydrazonoyl dicyanide,
52) (3-cyclopropyl-1-ethyl-2-oxo-2,3-dihydro-1H-imidazo[4,5-b]pyridin-6-yl)carbonohydrazonoyl dicyanide,
53) (3-cyclopropyl-1-isopropyl-2-oxo-2,3-dihydro-1H-imidazo[4,5-b]pyridin-6-yl)carbonohydrazonoyl dicyanide,
54) (3-isopropyl-1-methyl-2-oxo-2,3-dihydro-1H-imidazo[4,5-b]pyridin-6-yl)carbonohydrazonoyl dicyanide,
55) (1-ethyl-3-isopropyl-2-oxo-2,3-dihydro-1H-imidazo[4,5-b]pyridin-6-yl)carbonohydrazonoyl dicyanide,
56) (1,3-dimethyl-2-oxo-2,3-dihydro-1H-benzo[d]imidazol-5-yl)(methyl)carbonohydrazonoyl dicyanide, or
57) acetyl(1,3-dimethyl-2-oxo-2,3-dihydro-1H-benzo[d]imidazol-5-yl)carbonohydrazonoyl dicyanide.

8. A method of preparing the compound according to claim 1, the method comprising:

a first step of reacting a compound represented by Formula 5 below including a reactive amine group at one end with sodium nitrite and malononitrile in the presence of an acid to form an imine bond; and optionally, a second step of introducing an $R_1$ substituent into a product obtained in the previous step when $R_1$ is a substituent other than hydrogen:

[Formula 5]

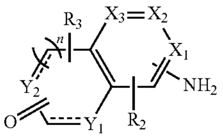

wherein, in Formula 5 above, $X_1$ to $X_3$, $Y_1$, $Y_2$, n, ------, $R_2$, and $R_3$ are as defined in claim 1, and when $Y_1$ and $Y_2$ are N(H), N(H) is protected by tert-butoxycarbonyl.

9. The method of claim 8, wherein when N(H) of $Y_1$ and $Y_2$ is protected by tert-butoxycarbonyl, the method further comprises a deprotection step after the reaction.

10. The method of claim 8, wherein the first step is performed by way of a series of processes comprising the steps of:

1-1) dissolving the compound of Formula 5 and sodium nitrite in a $C_{1-4}$ lower alcohol solvent and adding an aqueous acid solution thereto at a temperature of −5° C. to 5° C. to form a diazonium salt, 1-2) adding malononitrile to a reaction solution including the diazonium salt obtained in step 1-1) and performing a reaction at a temperature of 15° C. to 40° C., and 1-3) neutralizing the reaction solution of step 1-2) by adding an aqueous base solution thereto.

11. The method of claim 8, further comprising a step of reducing the nitro group of the compound represented by one of Formulae 5-a to 5-c into an amine group before the first step:

[Formula 5-a]

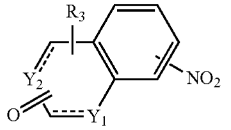

[Formula 5-b]

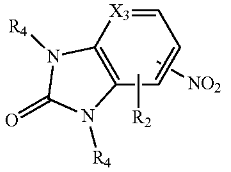

[Formula 5-c]

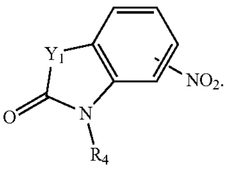

12. The method of claim 11, wherein the compound represented by Formula 5-a above is prepared by reacting a precursor of the compound, in which one of $Y_1$ and $Y_2$ is CH, and the other is O, with an amine-based compound $NH_2R_4$ in a state of being dissolved in an organic solvent to substitute the O site with $NR_4$.

13. The method of claim 12, wherein the precursor of the compound represented by Formula 5-a above, in which one of $Y_1$ and $Y_2$ is CH, and the other is O, is prepared, optionally, by cyclization between a nitrobenzoic acid derivative and N, N-dimethylformamide dimethylacetal or acetal acetone.

14. The method of claim 11, wherein the compound represented by Formula 5-b or 5-c above is prepared, optionally, by further performing a step of introducing an $R_4$ substituent via a reaction with a precursor compound including $R_4$ and a reactive halide.

15. The method of claim 11, wherein the compound represented by Formula 5-b above is prepared, optionally, by cyclization between unsubstituted or $R_2$-substituted 1,2-diaminenitrophenyl and carbonyldiimidazole (CDI).

16. A composition for inhibiting aggregation of tau protein comprising the compound according to claim 1 as an active ingredient.

17. A composition for inhibiting hyperphosphorylation of tau protein comprising the compound according to claim 1 as an active ingredient.

18. A pharmaceutical composition for treating a disease caused by aggregation or hyperphosphorylation of tau protein comprising the compound according to claim 1 as an active ingredient.

19. The pharmaceutical composition of claim 18, wherein the disease caused by aggregation or hyperphosphorylation of tau protein is selected from the group consisting of Alzheimer's disease, Parkinson's disease, vascular dementia, acute stroke, trauma, cerebrovascular disease, brain cord trauma, spinal cord trauma, peripheral neuropathy, retinopathy, glaucoma, and tauopathy.

20. The pharmaceutical composition of claim 19, wherein the tauopathy is selected from the group consisting of chronic traumatic encephalopathy (CTE), primary age-related tauopathy, progressive supranuclear palsy, corticobasal degeneration, Pick's disease, argyrophilic grain disease (AGD), frontotemporal dementia (FTD), parkinsonism linked to chromosome 17, Lytico-bodig disease (Parkinsonism-dementia complex of Guam), ganglioglioma, gangliocytoma, meningioangiomatosis, postencephalitic Parkinsonism, subacute sclerosing panencephalitis, lead encephalopathy, tuberous sclerosis, pantothenate kinase-associated neurodegeneration, lipofuscinosis, post-traumatic stress disorder, and traumatic brain injury.

* * * * *